US012351640B2

(12) United States Patent
Rehm et al.

(10) Patent No.: US 12,351,640 B2
(45) Date of Patent: Jul. 8, 2025

(54) CHIMERIC ANTIGEN RECEPTOR AND CAR-T CELLS THAT BIND BCMA

(71) Applicant: Max-Delbrück-Centrum für Molekulare Medizin in der Helmholtz-Gemeinschaft, Berlin (DE)

(72) Inventors: Armin Rehm, Berlin (DE); Uta Elisabeth Höpken, Berlin (DE); Julia Bluhm, Berlin (DE); Wolfgang Uckert, Berlin (DE); Elisa Kieback, Berlin (DE); Stephen Marino, Berlin (DE)

(73) Assignee: Max-Delbrück-Centrum für Molekulare Medizin in der Helmholtz-Gemeinschaft, Berlin (DE)

( * ) Notice: Subject to any disclaimer, the term of this patent is extended or adjusted under 35 U.S.C. 154(b) by 0 days.

(21) Appl. No.: 18/667,995

(22) Filed: May 17, 2024

(65) Prior Publication Data
US 2024/0382522 A1 Nov. 21, 2024

Related U.S. Application Data

(62) Division of application No. 16/307,854, filed as application No. PCT/EP2017/063862 on Jun. 7, 2017, now Pat. No. 12,048,718.

(30) Foreign Application Priority Data

Jun. 7, 2016 (EP) ..................... 16173401

(51) Int. Cl.
*C07K 16/28* (2006.01)
*A61K 35/17* (2025.01)
*A61K 39/00* (2006.01)
*A61K 40/11* (2025.01)
*A61K 40/22* (2025.01)
*A61K 40/31* (2025.01)
*A61K 40/41* (2025.01)
*A61K 40/42* (2025.01)
*A61K 47/65* (2017.01)
*C07K 14/705* (2006.01)
*C12N 5/0783* (2010.01)
*C12N 15/62* (2006.01)
*C12N 15/85* (2006.01)

(52) U.S. Cl.
CPC .......... *C07K 16/2878* (2013.01); *A61K 35/17* (2013.01); *A61K 40/11* (2025.01); *A61K 40/22* (2025.01); *A61K 40/31* (2025.01); *A61K 40/418* (2025.01); *A61K 40/4211* (2025.01); *A61K 40/4215* (2025.01); *A61K 47/65* (2017.08); *C07K 14/70596* (2013.01); *C12N 5/0636* (2013.01); *C12N 15/62* (2013.01); *C12N 15/85* (2013.01); *A61K 2039/505* (2013.01); *A61K 2239/31* (2023.05); *A61K 2239/38* (2023.05); *A61K 2239/48* (2023.05); *C07K 2317/24* (2013.01); *C07K 2317/33* (2013.01); *C07K 2317/34* (2013.01); *C07K 2317/622* (2013.01); *C07K 2317/73* (2013.01); *C07K 2319/03* (2013.01)

(58) Field of Classification Search
None
See application file for complete search history.

(56) References Cited

U.S. PATENT DOCUMENTS

| 10,144,782 B2 | 12/2018 | Oden et al. |
| 2007/0111270 A1 | 5/2007 | Zhang et al. |
| 2010/0099103 A1 | 4/2010 | Hsieh et al. |

FOREIGN PATENT DOCUMENTS

| WO | WO 2013/075027 A2 | 5/2013 | |
| WO | WO 2013/154760 A1 | 10/2013 | |
| WO | WO 2014/020056 A1 | 2/2014 | |
| WO | WO 2014/031687 A1 | 2/2014 | |
| WO | WO 2014/068079 A1 | 5/2014 | |
| WO | WO 2015/052538 A1 | 4/2015 | |
| WO | WO 2015/086548 A1 | 6/2015 | |
| WO | WO 2015/128509 A1 | 9/2015 | |
| WO | WO 2015/128653 A2 | 9/2015 | |
| WO | WO 2015/132604 A1 | 9/2015 | |
| WO | WO 2015/150327 A1 | 10/2015 | |
| WO | WO 2015/157399 A1 | 10/2015 | |
| WO | WO 2015/158671 A1 | 10/2015 | |
| WO | WO-2015166073 A1 * | 11/2015 | ....... A61K 39/39533 |
| WO | WO 2016/014535 A1 | 1/2016 | |
| WO | WO 2016/014565 A2 | 1/2016 | |
| WO | WO 2016/014789 A2 | 1/2016 | |

(Continued)

*Primary Examiner* — Amy E Juedes
*Assistant Examiner* — Brian Hartnett
(74) *Attorney, Agent, or Firm* — Knobbe Martens Olson & Bear LLP

(57) ABSTRACT

An isolated chimeric antigen receptor polypeptide (CAR), wherein the CAR comprises an extracellular antigen-binding domain, comprising an antibody or antibody fragment that binds a B Cell Maturation Antigen (BCMA) polypeptide. The CAR preferably binds an epitope comprising one or more amino acids of residues 13 to 32 of the N-terminus of human BCMA. Also disclosed is a nucleic acid molecule encoding the CAR of the invention, a genetically modified immune cell, preferably a T cell, expressing the CAR of the invention and the use of said cell in the treatment of a medical disorder associated with the presence of pathogenic B cells, such as a disease of plasma cells, memory B cells and/or mature B cells, in particular multiple myeloma, non-Hodgkin's lymphoma or autoantibody-dependent autoimmune diseases.

20 Claims, 18 Drawing Sheets
Specification includes a Sequence Listing.

(56) References Cited

FOREIGN PATENT DOCUMENTS

| WO | WO 2016/026742 A1 | 2/2016 |
| WO | WO 2016/033570 A1 | 3/2016 |
| WO | WO 2016/044811 A1 | 3/2016 |

* cited by examiner

Fig. 2
CAR IX.   CD28 Backbone
CAR X.
CAR XI. (w/o codon optimization)
CAR XV.   4-1BB Backbone
CAR XVI.
CAR XVII. (w/o codon optimization)

Fig. 3

| | Leader | scFv | Order | Linker | Hinge | Trans-membrane domain | Costimulatory domain | Activation domain |
|---|---|---|---|---|---|---|---|---|
| IX | Igκ | humanized | VH - VL | Whitlow | IgG1 | CD28 | CD28 | CD3ζ |
| X | Igκ | humanized | VL - VH | Whitlow | IgG1 | CD28 | CD28 | CD3ζ |
| XI | Igκ | Humanized (w/o codon opt.) | VH - VL | Whitlow | IgG1 | CD28 | CD28 | CD3ζ |
| XII | Igκ | humanized | VH - VL | Whitlow | IgG4 (Hi - CH2 - CH3) | CD28 | CD28 | CD3ζ |
| XIII | Igκ | humanized | VH - VL | Whitlow | IgG4 (Hi - CH3) | CD28 | CD28 | CD3ζ |
| XIV | Igκ | humanized | VH - VL | Whitlow | IgG4 (Hi) | CD28 | CD28 | CD3ζ |
| XV | Igκ | humanized | VL - VH | Whitlow | IgG1Δ | CD8α | 4-1BB | CD3ζ |
| XVI | Igκ | humanized | VL - VH | Whitlow | IgG1Δ | CD8α | 4-1BB | CD3ζ |
| XVII | Igκ | humanized | VL - VH | Whitlow | IgG1Δ | CD8α | 4-1BB | CD3ζ |

Fig. 4

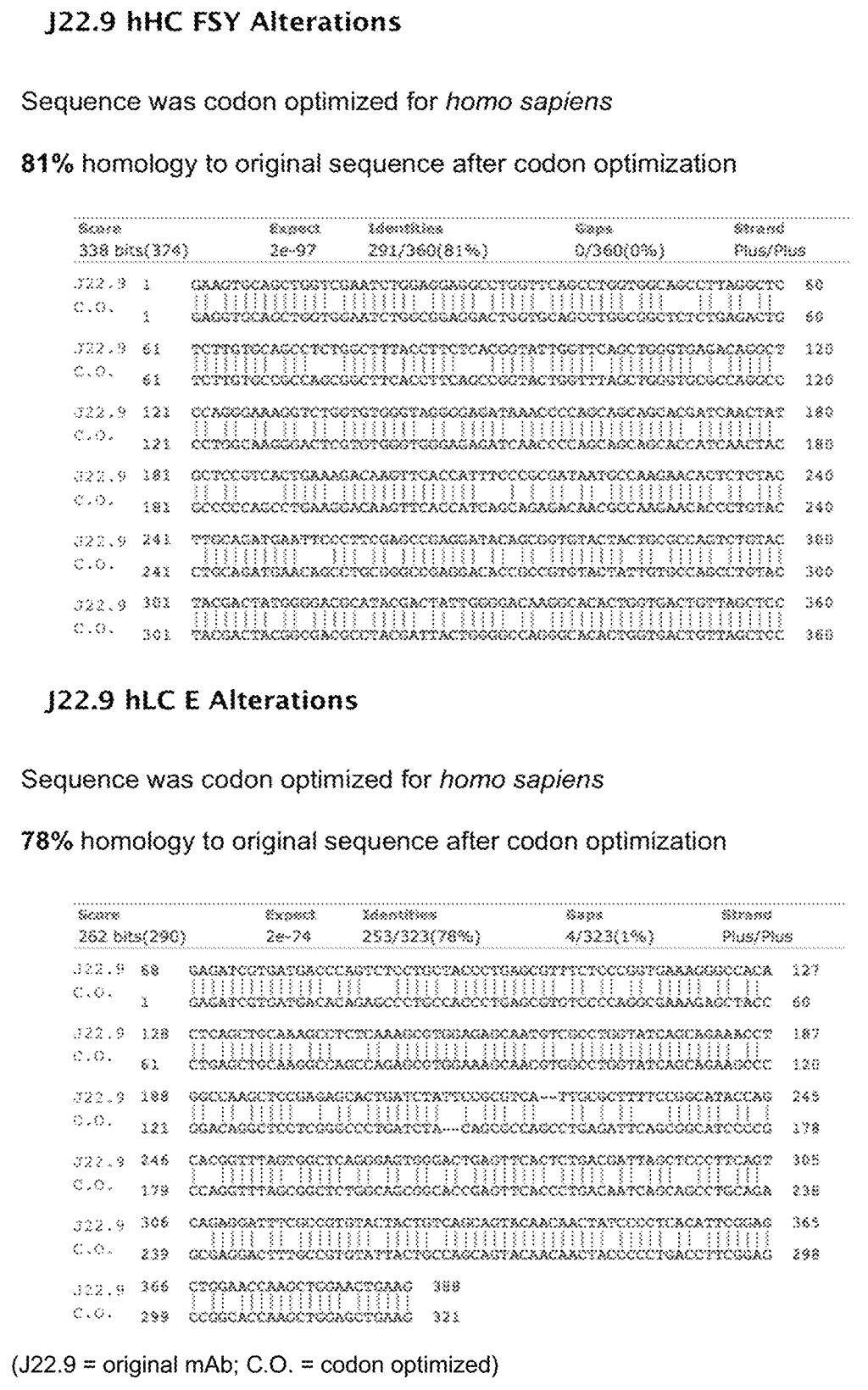

J22.9 hHC FSY Alterations

Sequence was codon optimized for *homo sapiens*

81% homology to original sequence after codon optimization

J22.9 hLC E Alterations

Sequence was codon optimized for *homo sapiens*

78% homology to original sequence after codon optimization (J22.9 = original mAb; C Fig. 11
Multiple Myeloma Cell Lines
Anti-BCMA Staining
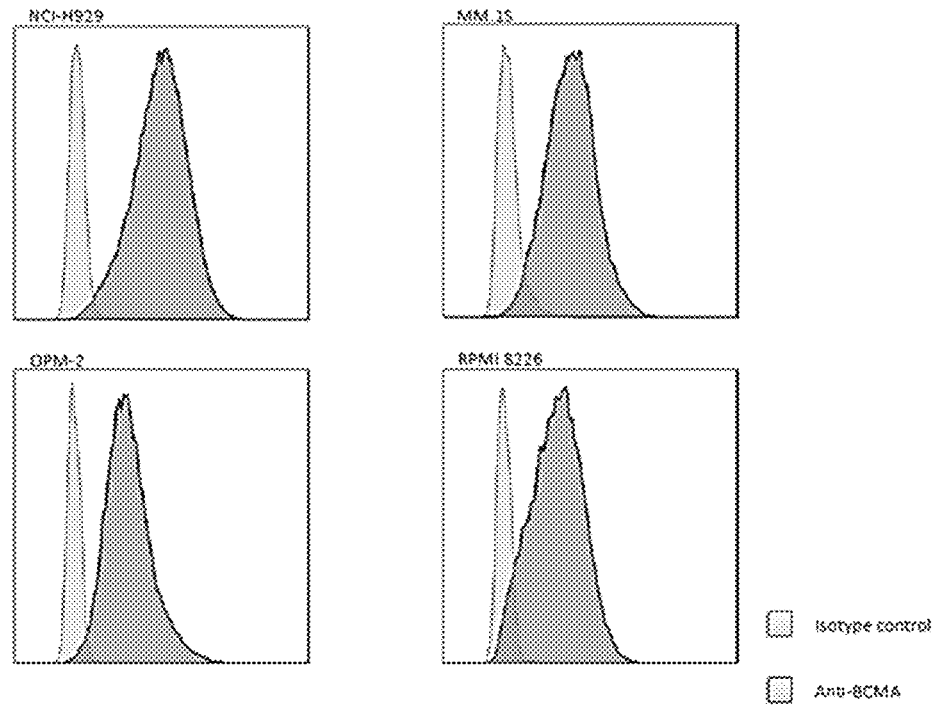
Multiple Myeloma Cell Lines
Anti-CD19 Staining
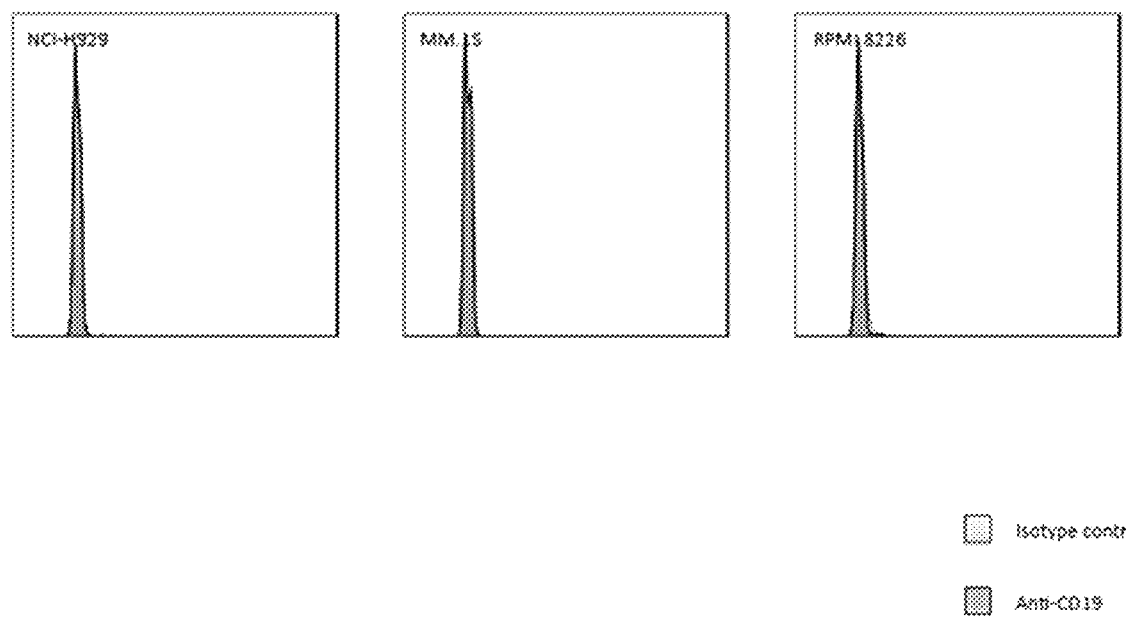

Fig. 11 (cont.)
B Cell Lymphoma Cell Lines
Anti-BCMA Staining
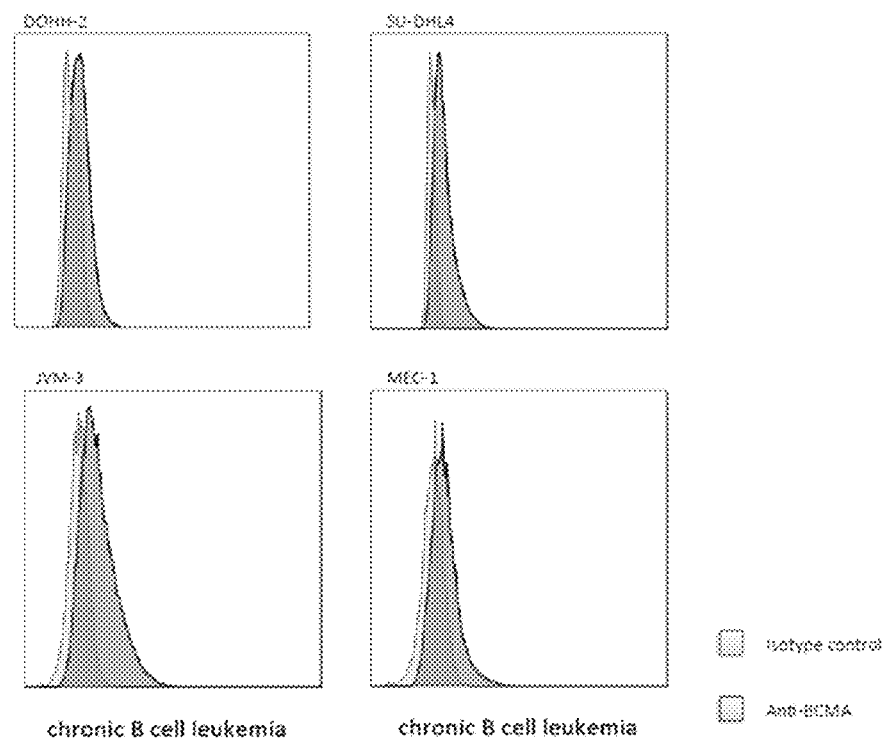
B Cell Lymphoma Cell Lines
Anti-CD19 Staining
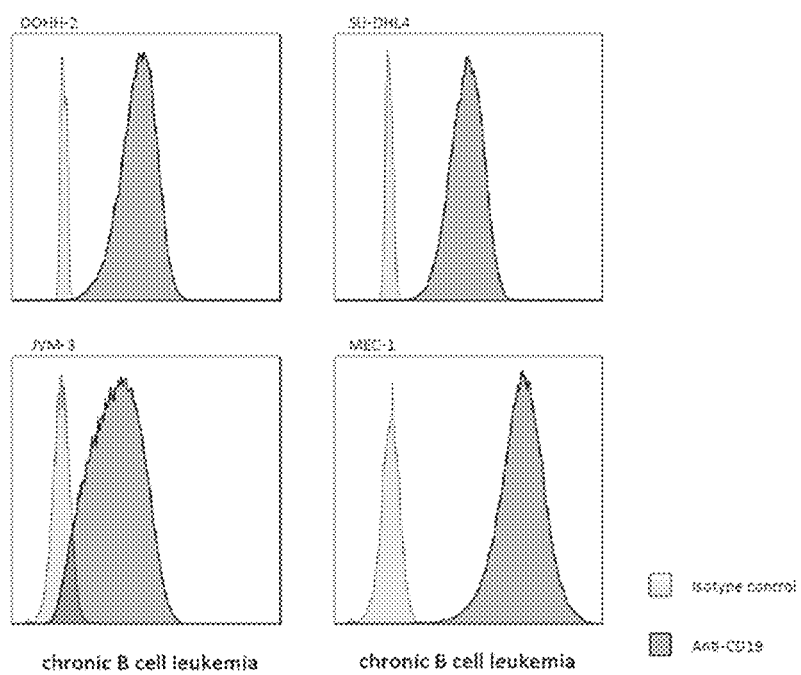

Fig. 11 (cont.)
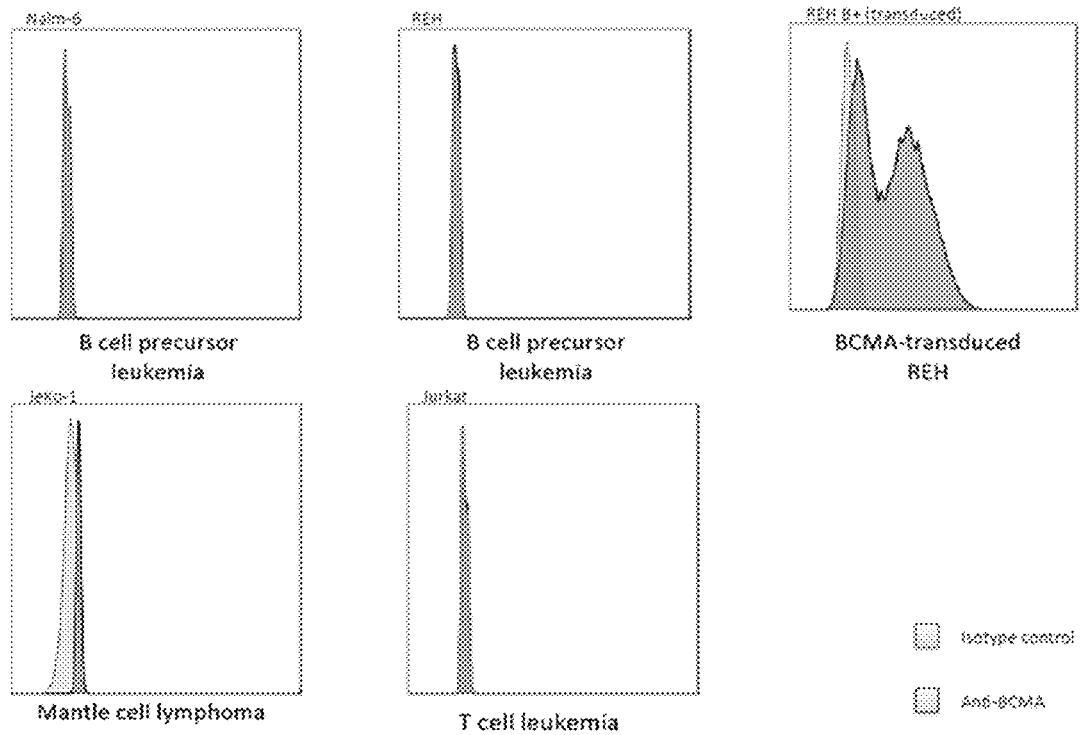
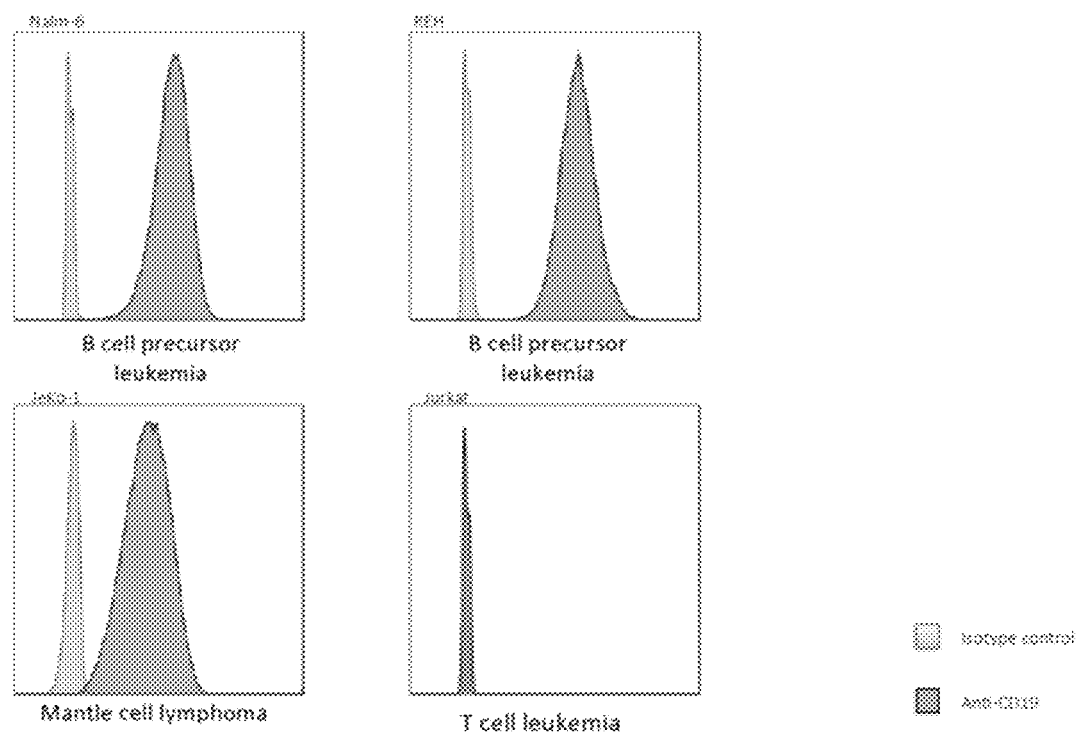

```
            1         10        20        30        40        50
HCg    XVQLXXSGGGLVQPGGSLXLSCAASGXXFXXYXXXWVRXAPGKGLXXXGX
HCm    QVQLQQSGGGLVQPGGSLKLSCAASGIDFSRYWMSWVRRAPGKGLEWIGE
HCpH   EVQLVESGGGLVQPGGSLRLSCAASGFTFDDYWMSWVRQAPGKGLEWVGE
hHC01  EVQLVESGGGLVQPGGSLRLSCAASGFTFSRYWMSWVRQAPGKGLVWVGE
hHC02  EVQLVESGGGLVQPGGSLRLSCAASGFTFSRYWXSWVRQAPGKGLVWVGE
hHC03  EVQLVESGGGLVQPGGSLRLSCAASGFTFSRYXMXWVRQAPGKGLVXVGX
hHC04  EVQLVESGGGLVQPGGSLRLSCAASGFTFSRYWISWVRQAPGKGLVWVGE
hHC05  EVQLVESGGGLVQPGGSLRLSCAASGFTFSRYWFSWVRQAPGKGLVWVGE
hHC06  EVQLVESGGGLVQPGGSLRLSCAASGFTFSRYWISWVRQAPGKGLVWVGE
hHC07  EVQLVESGGGLVQPGGSLRLSCAASGFTFSRYWFSWVRQAPGKGLVWVGE 51        60        70        80        90       100
HCg    INPXXSTINYAPSLKXXFXISRDNAKNTLYLQMXXXRSEDTAXYYCASXX
HCm    INPDSSTINYAPSLKDKFIISRDNAKNTLYLQMSKVRSEDTALYYCASLY
HCpH   INPDSSTINYAPSLKGRFTISRDNAKNTLYLQMNSLRAEDTAVYYCASLY
hHC01  INPDSSTINYAPSLKDKFTISRDNAKNTLYLQMNSLRAEDTAVYYCASLY
hHC02  INPXXSTINYAPSLKDKFTISRDNAKNTLYLQMNSLRAEDTAVYYCASLY
hHC03  INPDSSTINYAPSLKDKFTISRDNAKNTLYLQMNSLRAEDTAVYYCASXX
hHC04  INPNSSTINYAPSLKDKFTISRDNAKNTLYLQMNSLRAEDTAVYYCASLY
hHC05  INPNSSTINYAPSLKDKFTISRDNAKNTLYLQMNSLRAEDTAVYYCASLY
hHC06  INPSSSTINYAPSLKDKFTISRDNAKNTLYLQMNSLRAEDTAVYYCASLY
hHC07  INPSSSTINYAPSLKDKFTISRDNAKNTLYLQMNSLRAEDTAVYYCASLY 101       110
HCg    XDYGDXXDYWGQGTXVTVSS
HCm    YDYGDAMDYWGQGTSVTVSS
HCpH   YDYGDAMDYWGQGTLVTVSS
hHC01  YDYGDAMDYWGQGTLVTVSS
hHC02  XDYGDAXDYWGQGTLVTVSS
hHC03  XDYGDXMDYWGQGTLVTVSS
hHC04  YDYGDAYDYWGQGTLVTVSS
hHC05  YDYGDAYDYWGQGTLVTVSS
hHC06  YDYGDAYDYWGQGTLVTVSS
hHC07  YDYGDAYDYWGQGTLVTVSS
```

X: Variable amino acid according to humanized sequences
HCg: General heavy chain variable sequence
HCm: mouse heavy chain variable sequence
HCpH: partially humanized heavy chain variable sequence

```
            1         10        20        30        40        50
LCg    XIVMTQSXXXXXXSXGXXVSXXCKASQSVXXXVXWXQQKPXQXPKXLIXX
LCm    DIVMTQSQRFMTTSVGDRVSVTCKASQSVDSNVAWYQQKPRQSPKALIFS
LCpH   DIVMTQSPATLSVSVGDEVTLTCKASQSVDSNVAWYQQKPGQAPKLLIYS
hLC01  EIVMTQSPATLSVSPGERATLSCKASQSVDSNVAWYQQKPGQAPRALIYS
hLC02  EIVMTQSPATLSVSPGERATLSCKASQSVXXNVAWYQQKPGQAPRALIYS
hLC03  EIVMTQSPATLSVSPGERATLSCKASQSVDXXVXWXQQKPGQAPRALIXX
hLC04  EIVMTQSPATLSVSPGERATLSCKASQSVESNVAWYQQKPGQAPRALIYS 51        60        70        80        90        100
LCg    XXXRXSGXPARFXGSXXGTXFTLTISXLQSEDXAXYXCXQXNNXPXTFGA
LCm    ASLRFSGVPARFTGSGSGTDFTLTISNLQSEDLAEYFCQQYNNYPLTFGA
LCpH   DDLRFSGVPARFSGSGSGTDFTLTISSLQSEDFAVYYCQQYNNYPLTFGA
hLC01  ASLRFSGIPARFSGSGSGTEFTLTISSLQSEDFAVYYCQQYNNYPLTFGA
hLC02  ASLRFSGIPARFSGSGSGTEFTLTISSLQSEDFAVYYCQQYNNYPLTFGA
hLC03  AXXRXSGIPARFSGSXXGTEFTLTISSLQSEDFAVYYCXQXNNXPXTFGA
hLC04  ASLRFSGIPARFSGSGSGTEFTLTISSLQSEDFAVYYCQQYNNYPLTFGA

101
LCg    GTKLELKR
LCm    GTKLELKR
LCpH   GTKLELKR
hLC01  GTKLELKR
hLC02  GTKLELKR
hLC03  GTKLELKR
hLC04  GTKLELKR
```

X: Variable amino acid according to either mouse or humanized sequences
LCg: General heavy chain variable sequence
LCm: mouse heavy chain variable sequence
LCpH: partially humanized heavy chain variable sequence Fig. 16
A
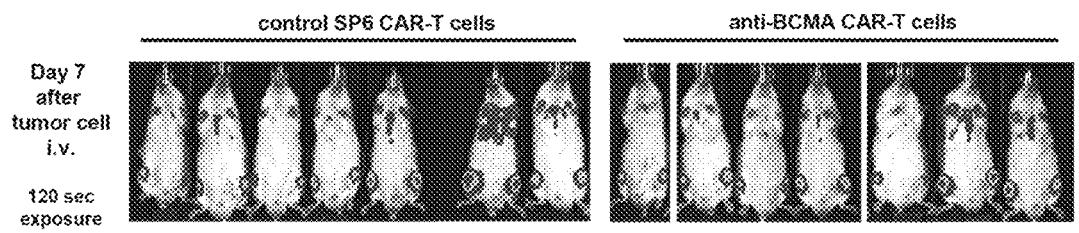
B
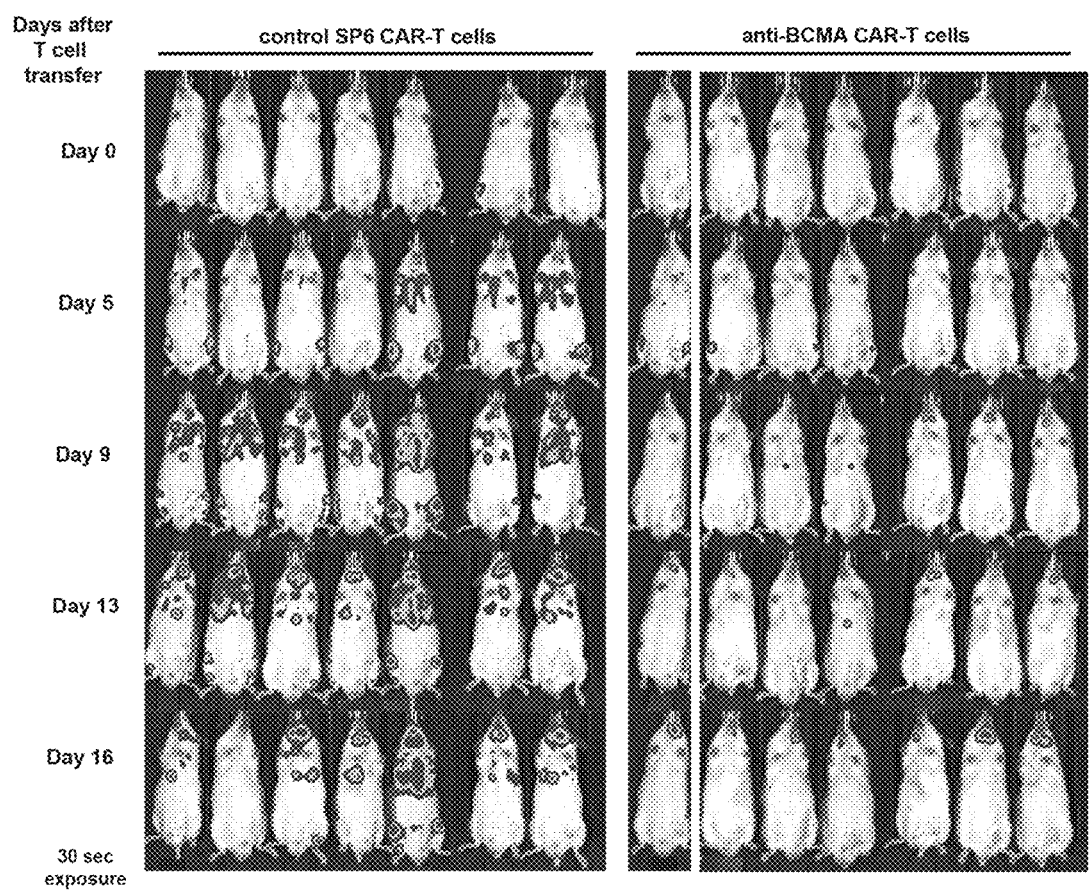
C
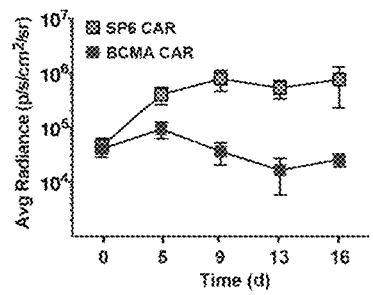

CHIMERIC ANTIGEN RECEPTOR AND CAR-T CELLS THAT BIND BCMA

The invention relates to an isolated chimeric antigen receptor polypeptide (CAR), wherein the CAR comprises an extracellular antigen-binding domain, comprising an antibody or antibody fragment that binds a B Cell Maturation Antigen (BCMA) polypeptide. The CAR preferably binds an epitope comprising one or more amino acids of residues 13 to 32 of the N-terminus of human BCMA. The invention further relates to a nucleic acid molecule encoding the CAR of the invention, a genetically modified immune cell, preferably a T cell, expressing the CAR of the invention and the use of said cell in the treatment of a medical disorder associated with the presence of pathogenic B cells, such as a disease of plasma cells, memory B cells and/or mature B cells, in particular multiple myeloma, non-Hodgkin's lymphoma or autoantibody-dependent autoimmune diseases.

REFERENCE TO SEQUENCE LISTING

A Sequence Listing submitted as an XML file via Patent Center is hereby incorporated by reference in accordance with 35 U.S.C. § 1.52 (e). The name of the XML file for the Sequence Listing is 59804597_1.XML, the date of creation of the XML text file is Jul. 8, 2024, and the size of the ASCII text file is 172,089 bytes.

BACKGROUND OF THE INVENTION

In cancer immunotherapy, adoptive transfer of T cells (ATT) genetically modified to recognize tumor-specific or tumor-associated antigens is a promising approach in order to eradicate tumor and tumor stem cells. Thus, in contrast to traditional chemo-, radiation- and surgical therapies, tumor recurrence can be potentially avoided. Moreover, novel pathway-selective drugs often allow for excellent tumor control, but the disease course usually switches to a chronic phase without definite tumor elimination.

The advent of genetically modified T cells that express CARs has proven a tremendous success in B cell lymphoma/leukemia treatment, despite the fact that patients were heavily pre-treated and had previously received several lines of chemotherapies, antibody therapies or even autologous/allogeneic bone marrow transplantations. Thus, ATT with CAR-T cells was used successfully as salvage therapy.

CARs are synthetic, engineered immunoglobulin-derived receptors that can recognize surface antigens in an MHC-independent fashion. Unlike TCRs, CARs have a broader range of affinities that can engage the target antigen without necessarily exhibiting cross-reactivity. The target antigens must be surface-deposited and can include tumor-associated proteins, carbohydrates or even glycolipids. Another advantage of CAR-T cells is their rapid generation by transduction of autologous T cells, which can be either of CD4+ or CD8+ origin. CARs can be produced "off-the-shelf" and their targets are typically broadly expressed (>90%) in a defined tumor entity, as shown for CD19+B-cell leukemias and lymphomas. It has been suggested that CAR T cells act as a "living drug" that could be maintained even after a single T cell infusion.

A strong medical demand exists for the chimeric antigen receptor (CAR)-T cell product described herein. Firstly, multiple myeloma is an incurable B cell non-Hodgkin lymphoma (B-NHL) which is derived from a malignantly transformed plasma cell clone. As a peculiarity, tumor cells localize predominantly to the bone marrow. This disease is the most frequent tumor of bone and bone marrow, has a 10 year survival rate of 50% among intensely treated younger patients, and is responsible for 2% of annual deaths from cancer. The incidence rate is 5/100,000, and the median age at diagnosis is 70 years, indicating that in many patients co-morbidities exist that preclude intense and prolonged chemotherapies. The standard of care is chemotherapy, either alone or in combination with autologous stem cell transplantation, immunomodulatory drugs, local irradiation, proteasome inhibitors, and for very few patients allogeneic stem cell transplantation is applicable. Despite intense treatments with the aformentioned modalities, the disease usually relapses and after multiple lines of therapies secondary resistance develops.

Secondly, the much larger group of classical B-NHL contain diverse entities of neoplasias derived from B lymphocytes that usually home to secondary lymphatic organs such as diffuse large B cell lymphoma (DLBCL), follicular lymphoma (FL), and a subgroup of chronic lymphocytic leukemia (CLL). While the total incidence rate of all NHL is about 10-12/100,000 (>85% of B cell origin), most of them are diseases of adults with a substantial increase in the elderly. The demographic development would predict that total numbers will increase due to aging of Western societies. Clinically, B-NHL are heterogenous and can be distinguished by an aggressive and indolent course. Substantial progress has been made over the last 15 years in the treatment of B-NHL, the standard of care is combined antibody/chemotherapy, either alone or in combination with autologous stem cell transplantation, immunomodulatory drugs, irradiation, proteasome inhibitors, signaling pathway inhibitors, and for very few patients allogeneic stem cell transplantation applies. Because in many B-NHL entities median age at diagnosis is >55-60 years, co-morbidities also exist that preclude intense and extended chemotherapies or even allogeneic bone marrow transplantations.

The advent of adoptive CAR-T cell therapies targeted at the broadly expressed CD19 antigen on lymphoma B cells has made it possible to overcome these limitations and currently, about 20 CD19 CAR-T cell studies are registered at the FDA for the treatment of B-NHL and B-ALL. Although major breakthroughs were already achieved in clinical trials on CLL in 2011 and on B-ALL in 2013, to the best knowledge of the inventors permission to use identical CD19 CAR-products in Germany has been granted only very recently by biomedical companies. In other EU countries (e.g. Austria), clinical trials using CD19 CAR T-cells are also under way. More importantly, in anti-CD19 antibody or CAR-T cell therapies directed against B-NHL resistance occurs due to antigen loss. Because treatment resistance is observed after multiple lines of chemo-/immunotherapy, alternative target structures are urgently warranted.

For the indication multiple myeloma, two anti BCMA-CAR products have been described previously and have entered phase I clinical studies. These studies do not prove anti-BCMA CAR applicability to B-NHL. Regarding B-NHL, anti-BCMA targeted therapies represent possible alternatives, in particular when anti-CD19 CARs have failed. Other immunotherapy strategies targeted at multiple myeloma and tested in clinical studies are anti-CD19 CARs, NY-ESO1 and MAGE-A1-directed, TCR-transduced T cells. In stark contrast to BCMA as tumor target, frequencies of eligible patients are far lower because these target antigens are expressed in less than 10% of the cases. Other targeted therapies include anti-CD38 and anti-SLAMF7 antibodies, conceptually these therapies are completely different because antibodies are not self-sustained, do not form memory and to our knowledge, are not yet proven to mediate sufficient tumor eradication.

In addition, the ability to specifically target plasma cells would be of great benefit for the treatment of autoimmune diseases. Mild forms of autoimmune disease are usually initially treated with nonsteroidal anti-inflammatory drugs (NSAID) or disease-modifying anti-rheumatic drugs (DMARD). More severe forms of Systemic Lupus Erythematosus (SLE), involving organ dysfunction due to active disease, usually are treated with steroids in conjunction with strong immunosuppressive agents such as cyclophosphamide, a cytotoxic agent that targets cycling cells.

Only recently Belimumab, an antibody targeting the cytokine BAFF, which is found at elevated levels in serum of patients with autoimmune diseases, received approval by the Food and Drug Administration (FDA) for its use in SLE. However, only newly formed B cells rely on BAFF for survival in humans, whereas memory B cells and plasma cells are less susceptible to selective BAFF inhibition (Jacobi et al. (2010) Arthritis Rheum 62:201-210). For rheumatoid arthritis (RA), TNF inhibitors were the first licensed biological agents, followed by Abatacept, Rituximab, and Tocilizumab and others: they suppress key inflammatory pathways involved in joint inflammation and destruction, which, however, comes at the price of an elevated infection risk due to relative immunosuppression (Chan et al. (2010) Nat Rev Immunol 10:301-316, Keyser (2011) Curr Rheumatol Rev 7:77-87).

Only recently, CAR-T cells were also discussed as a targeted approach to treat autoantibody-mediated diseases (Ellebrecht et al. (2016) Science 353:179-184). Long-lived, sessile plasma cells residing in survival niches in the bone marrow are often resistant to conventional immunosuppressive and cytotoxic drugs as well as to therapies targeting B cells and their activation. In particular, Rituximab appears unsuitable for such a treatment, as its target antigen CD20 is not expressed on plasma cells. This therapeutic challenge could be met by employing anti-BCMA CAR-T cell constructs, as BCMA is expressed on long-lived plasma cells.

At present, a number of other anti-BCMA CAR constructs have been described in the art. In 2013, the group of James N. Kochenderfer published the first anti-BCMA CAR-transduced T cell approach, a pre-clinical study using in vitro assays and mouse testing (Carpenter et al., 2013; Clin Cancer Res; 19 (8); 2048-2060). In June 2015, Bluebird Bio and Celgene announced their collaboration to focus on developing BCMA CAR-T cell therapies. Phase I clinical trial enrollment has started in January 2016 for multiple myeloma patients. In early 2016, Abramson Cancer Center of the University of Pennsylvania started participant recruitment for a Phase I study using anti-BCMA CAR-transduced T cells in the treatment of multiple myeloma patients (ClinicalTrials.gov Identifier: NCT02546167). CARs directed to BCMA have been described in WO 2016/014789, WO 2016/014565 and WO 2013/154760. WO 2015/128653 also discloses CAR sequences that bind BCMA, in which the portion of the CAR responsible for epitope recognition is a variant of the APRIL ligand, which shows improved binding to BCMA compared to wild-type APRIL. Alternative therapeutic strategies relate to an anti-CD38 CAR. BCMA-binding antibodies are disclosed in WO 2015/166073 and WO 2014/068079.

Although a number of potential alternative therapies are in development, a significant need remains for providing effective means for addressing medical disorders associated with the presence of pathogenic B cells, in particular multiple myeloma, non-Hodgkin's lymphoma or autoantibody-dependent autoimmune diseases.

SUMMARY OF THE INVENTION

In light of the prior art the technical problem underlying the invention was the provision of an agent suitable for treating diseases associated with pathogenic B cells.

This problem is solved by the features of the independent claims. Preferred embodiments of the present invention are provided by the dependent claims.

Therefore, the invention relates to an isolated chimeric antigen receptor polypeptide (CAR), wherein the CAR comprises:
  i. an extracellular antigen-binding domain, comprising an antibody or antibody fragment that binds a B Cell Maturation Antigen (BCMA) polypeptide,
  ii. a transmembrane domain, and
  iii. an intracellular domain,
  and wherein said CAR binds an epitope comprising one or more amino acids of residues 13 to 32 of the N-terminus of BCMA.

The present invention therefore relates to a genetically modified immune cell, preferably a T cell, expressing the CAR of the invention and the use of said cell in the treatment of a medical disorder associated with the presence of pathogenic B cells.

The present invention therefore provides a preferably autologous T cell suitable for transplantation comprising an anti-BCMA CAR for the treatment of distinct stages of mature B-NHLs and multiple myeloma. In preferred embodiments of the immunotherapy approach of the present invention, patient-derived T cells are transduced, preferably retrovirally, to express an artificial immune receptor as described herein, composed of an extracellular antibody-derived antigen recognition part, fused to a transmembrane section, and followed by intracellular signaling domains. The construct described herein confers transduced T cells with anti-tumor cytolytic capacity.

As shown for other clinical CAR-T cell transfers, the present invention is characterized in that the anti-BCMA CAR-T cells based on the CAR described herein have predictable, tolerable and manageable side effects. Preclinical testing of the BCMA CAR-T cells described herein shows selectivity for the tumor-associated antigen BCMA. T cells equipped with the anti-BCMA CAR have a high affinity and avidity and recognize and destroy multiple myeloma cells while sparing normal hematopoietic cells. In a preferred embodiment, the transfer of autologous T cells prevents the possibility of graft-versus-host-disease. Memory CAR-T cell formation, which is important for the prevention of a relapse, can potentially develop.

Due to the high affinity and avidity of the anti-BCMA CAR-T cell described herein, even low BCMA-expressing mature B-NHLs can be recognized, allowing for T cell activation and tumor cell killing.

In preferred embodiments such mature B-NHL entities include certain stages of FL (follicular lymphoma), DLBCL (diffuse large B cell lymphoma), mantle cell lymphoma (MCL), and CLL (chronic lymphocytic leukemia).

The antigen recognition part of the CAR described herein is preferably based upon a humanized antibody described in WO/2015/166073. The antibody described therein was used to construct a number of CAR constructs that retain the high affinity and specificity for BCMA.

The high affinity and specificity enable a reduction in off-target reactivity, providing an advantage over other BCMA CAR constructs. It was a surprising result that the high specificity and affinity of the original antibody could be maintained in the CAR as described herein to target B cells expressing even very low amounts of BCMA antigen.

The CAR of the present invention preferably binds an epitope comprising one or more amino acids of residues 13 to 32 of the N-terminus of BCMA. In other embodiments, binding to other epitopes of BCMA, in particular the N-terminus of BCMA is also possible.

The present invention also encompasses various signaling domains. The exchange of signaling domains meets the demands for either a strong and rapid effector phase (CD28 co-stimulatory domain), or a long-lasting relapse control as secured by a T cell memory population (4-1BB signaling domain). As demonstrated herein, the various signaling domains may be exchanged in multiple configuration, providing a CAR with flexibility with respect to its design without loss of the advantageous binding properties.

The anti-BCMA CAR-T cell product described herein is characterised by unique properties. Due to the low nanomolar affinity of the extracellular domain of the CAR-T cell construct, the anti-BCMA CAR as described herein has an unrivaled high affinity and confers extremely high specificity and avidity to T cells. These properties enable CAR-T cells to i) recognize, ii) be activated against, and iii) kill tumor target cells with high and, surprisingly, low BCMA surface expression.

The number of BCMA antigens expressed on the surfaces of tumor cells can be quantified by using an anti-BCMA antibody coupled to a fluorescent-dye in conjunction with Quantibrite beads (from Becton Dickenson). The preferred method applied to quantify BCMA antigens expressed on the surfaces of tumor cells is "fluorescence activated cell sorting/cell analysis" (FACS). Fluorescence intensity of beads correlates exactly with the numbers of fluorescent antibodies bound to cells, and this is a measure for the number of BCMA molecules on cells. Myeloma cell-associated fluorescence densities are typically at least 2-3 $\log_{10}$-fold higher compared to low fluorescent B-NHL cells, showing that BCMA antigen densities can also vary over a range of at least 2-3 $\log_{10}$-fold.

None of the competing anti-BCMA CARs has proven reactivity against B-NHL other than multiple myeloma cells or in very rare cases, Burkitt-lymphoma. Therefore, the anti-BCMA CAR exhibits reactivity against an unprecedented diversity of B-NHLs. These properties represent unexpected and surprising benefits with respect to CAR-T therapy. Typical expectations of a skilled person require a high number of target antigens to be expressed, in order to enable CAR-T targeting. The CAR-Ts employing the CARs of the invention show unprecedented activity against B cells with low expression levels of target antigen. In preferred embodiments, in combination with the MP71-vector and a gamma-retrovirus expression system, an unusually high transduction rate for human T cells can be achieved.

Preferred Embodiments Regarding the BCMA Epitope Bound by the CAR

The CAR of the present invention is directed preferably towards an epitope comprising one or more amino acids of residues 13 to 32 of the N-terminus of human BCMA. The amino acid sequence of residues 13 to 32 of CD269 are shown in SEQ ID No. 33. The N-terminus sequence of CD269 is provided in SEQ ID No. 32. The extracellular domain of CD269 is provided as SEQ ID No. 31.

An antigen comprising the extracellular domain of CD269 according to SEQ ID No. 31 was used in vaccination in order to generate the binding specificity of the mouse and chimeric antibody described herein and previously (WO/2014/068079) that has been modified for use in the CAR format in the present invention. Use of the entire CD269 protein, or fragments thereof comprising either a membrane-bound or intracellular domain, as an antigen during antibody generation could produce antibodies that bind concealed or intracellular domains of CD269, thereby rendering such agents unsuitable or disadvantageous for therapeutic application. The CAR of the present invention is therefore defined by its binding to the extracellular portion of CD269. The specific epitope within the extracellular domain also represents a preferred novel and unexpected characterising feature of the invention.

Fab fragments prepared from mouse or chimeric antibodies from the present CAR was derived were crystallized in complex with the purified BCMA extracellular domain and the complex structure solved. The structural analysis has revealed detailed information of the epitope of the binding region of the antibody/CAR of the present invention and its biological relevance. The binding of an epitope comprising one or more amino acids of residues 13 to 32 of BCMA of the extracellular domain by the antibody of the present invention is an advantageous property due to its high binding specificity and extracellular location. To the knowledge of the inventor, no CAR has been previously described that binds this region. In one embodiment the CAR of the present invention is characterised in that the CAR binds an epitope comprising one or more of amino acids 13, 15, 16, 17, 18, 19, 20, 22, 23, 26, 27 or 32 of CD269 (BCMA). In another embodiment the CAR of the present invention is characterised in that the antibody binds an epitope consisting of amino acids 13, 15, 16, 17, 18, 19, 20, 22, 23, 26, 27 and 32 of CD269 (BCMA). These residues represent the amino acids that interact directly with the antibody of the present invention, as identified by the crystal structure data provided herein. The numbering of these residues has been carried out with respect to SEQ ID No. 32, which provides the N-terminal sequence of human BCMA.

As disclosed previously, the affinity of the antibodies from which the CAR of the present invention was derived is surprisingly high and comparatively better than similar approaches attempted in the prior art. The CAR of the present invention is therefore defined by a high affinity not seen in other anti-BCMA CAR molecules. A Kd in the pM range (as shown below) is commonly accepted as an outstanding affinity not to be expected in common practice. In another aspect, the humanized antibody or antibody fragment, from which the CAR of the invention is derived, binds BCMA with high affinity, for example when measured by surface plasmon resonance, such as Biacore, the antibody binds to human BCMA with an affinity of 100 nM, 90, 80, 70, 60, 50, 40, 30 nM or less, or 20 nM or less, or an affinity of 15 nM or less, or an affinity of 5 nM or less, or an affinity of 1000 pM or less, or an affinity of 500 pM or less, or an affinity of 100 pM or less, or 80 pM or less, or for example about 50 pM. The CAR of the present invention therefore exhibits corresponding affinities.

In a further embodiment the antibody, from which the CAR of the invention was derived, binds to human CD269 when measured by surface plasmon resonance, such as Biacore, of between about 1 pM and about 100 nM, or between about 100 pM and about 50 nM, or between about 200 pM and about 20 nM. The CAR of the present invention therefore exhibits corresponding affinities.

In one embodiment the CAR and/or CAR-T of the present invention is characterised in that the CAR binds cells that express BCMA, wherein said BCMA is detectable on the cell surface, and wherein BCMA is present on the cell surface in 1-4 $\log_{10}$-fold, preferably 2-3 $\log_{10}$-fold, lower amounts compared to multiple myeloma cells, preferably compared to those multiple myeloma cell lines used in the examples demonstrated herein. Examples of such cells, without being limited thereto, are non-Hodgkin's lymphoma (B-NHL) cells, such as DOHH-2, SU-DHL4, JEKO-1, JVM-3 and/or MEC-1 cell lines.

Preferred Embodiments Regarding the CAR Sequences

In one embodiment the isolated chimeric antigen receptor polypeptide (CAR) of the invention is characterised in that the antigen-binding domain comprises a variable heavy chain (VH), said VH comprising:
- a heavy chain complementary determining region 1 (H-CDR1) with at least 80% sequence identity to SEQ ID NO 1 (GFTFSRYW),
- a heavy chain complementary determining region 2 (H-CDR2) with at least 80% sequence identity to SEQ ID NO 2 (INPSSSTI), and
- a heavy chain complementary determining region 3 (H-CDR3) with at least 80% sequence identity to SEQ ID NO 3 (ASLYYDYGDAYDY), and a variable light chain (VL), said VL comprising:
- a light chain complementary determining region 1 (L-CDR1) with at least 80% sequence identity to SEQ ID NO 4 (QSVESN),
- a light chain complementary determining region 2 (L-CDR2) with at least 80% sequence identity to SEQ ID NO 5 (SAS), and
- a light chain complementary determining region 3 (L-CDR3) with at least 80% sequence identity to SEQ ID NO 6 (QQYNNYPLT).

In one embodiment the isolated chimeric antigen receptor polypeptide (CAR) of the invention is characterised in that the antigen-binding domain comprises a variable heavy chain (VH), said VH comprising:
- a heavy chain complementary determining region 1 (H-CDR1) with at least 80% sequence identity to SEQ ID NO 25 (RYWFS),
- a heavy chain complementary determining region 2 (H-CDR2) with at least 80% sequence identity to SEQ ID NO 26 (EINPSSSTINYAPSLKDK), and
- a heavy chain complementary determining region 3 (H-CDR3) with at least 80% sequence identity to SEQ ID NO 27 (SLYYDYGDAYDYW), and a variable light chain (VL), said VL comprising:
- a light chain complementary determining region 1 (L-CDR1) with at least 80% sequence identity to SEQ ID NO 28 (KASQSVESNVA),
- a light chain complementary determining region 2 (L-CDR2) with at least 80% sequence identity to SEQ ID NO 29 (SASLRFS), and
- a light chain complementary determining region 3 (L-CDR3) with at least 80% sequence identity to SEQ ID NO 30 (QQYNNYPLTFG).

The CDR sequences recited above under SEQ ID NO 25-30 represent embodiments obtained using alternative parameters for defining the CDR regions, and encompassing for example additional flanking amino acids in comparison to SEQ ID NO 1-6.

The CDR sequences of SEQ ID NO 1-6 and 25-30 may also be defined such that a polypeptide sequence is encompassed by the invention with at least 70%, 75%, 80%, 85%, 90%, or at least 95% sequence identity to the specific sequences listed.

In one embodiment the isolated chimeric antigen receptor polypeptide (CAR) of the invention is characterised in that said CAR comprises a VH domain that comprises CDR sequences of: GFTFSRYW (H-CDR1; SEQ ID NO. 1);
- INPX$_2$X$_3$STI (H-CDR2; SEQ ID No. 7), wherein X$_2$X$_3$: SS, NS, TS, GS, KS, RS, SD, SN, DE; and
- ASLYX$_4$DYGDAX$_5$DY (H-CDR3; SEQ ID NO. 8), wherein X$_4$: Y, L, A, V, F, I, W, and/or X$_5$: Y, L, F, I, V, A, C, and a VL domain that comprises CDR sequences of:
- QSVX$_1$X$_2$N (L-CDR1; SEQ ID NO. 9), wherein X$_1$X$_2$: ES, SS, TS, QS, HS, DH;
- SAS (L-CDR2; SEQ ID NO 5); and
- QQYNNYPLTFG (L-CDR3; SEQ ID NO. 10).

In alternative embodiments the isolated chimeric antigen receptor polypeptide (CAR) of the invention comprises a VH domain that comprises CDR sequences of:
- RYWX$_1$S (H-CDR1; SEQ ID NO. 34), wherein X$_1$: I, F, L, V, Y, C, G, A, S, T);
- EINPX$_2$X$_3$STINYAPSLKDK (H-CDR2; SEQ ID No. 35), wherein X$_2$X$_3$: SS, NS, TS, GS, KS, RS, SD, SN, DE; and
- SLYX$_4$DYGDAX$_5$DYW (H-CDR3; SEQ ID NO. 36), wherein X$_4$: Y, L, A, V, F, I, W, and/or X$_5$: Y, L, F, I, V, A, C, and a VL domain that comprises CDR sequences of:
- KASQSVX$_1$X$_2$NVA (L-CDR1; SEQ ID NO. 37), wherein X$_1$X$_2$: ES, SS, TS, QS, HS, DH;
- SASLRFS (L-CDR2; SEQ ID NO 29); and
- QQYNNYPLTFG (L-CDR3; SEQ ID NO. 30).

The CDR sequences recited above under SEQ ID NO 34-37 represent embodiments obtained using alternative parameters for defining the CDR regions, and for example encompassing additional flanking amino acids in comparison to SEQ ID NO 1-6.

In one embodiment the isolated chimeric antigen receptor polypeptide (CAR) of the invention is characterised in that said CAR comprises the following sequences:

```
                                     (SEQ ID NO. 1)
H-CDR1: GFTFSRYW, (SEQ ID NO. 2)
H-CDR2: INPSSSTI, (SEQ ID NO. 3)
H-CDR3: ASLYYDYGDAYDY, (SEQ ID NO. 4)
L-CDR1: QSVESN, (SEQ ID NO. 5)
L-CDR2: SAS,
and (SEQ ID NO. 6)
L-CDR3: QQYNNYPLT.
```

In one embodiment the isolated chimeric antigen receptor polypeptide (CAR) of the invention comprises CDR sequences of:

H-CDR1: RYWFS, (SEQ ID NO. 25)

H-CDR2: EINPSSSTINYAPSLKDK, (SEQ ID NO. 26)

H-CDR3: SLYYDYGDAYDYW, (SEQ ID NO. 27)

L-CDR1: KASQSVESNVA, (SEQ ID NO. 28)

L-CDR2: SASLRFS, and (SEQ ID NO. 29)

L-CDR3: QQYNNYPLTFG, (SEQ ID NO. 30)

In one embodiment the isolated chimeric antigen receptor polypeptide (CAR) of the invention is characterised in that said CAR comprises a VH domain with at least 80% sequence identity to SEQ ID NO 11

(EVQLVESGGGLVQPGGSLRLSCAASGFTFSRYWFSWVRQAPGKGLVWVG

EINPSSSTINYAPSLKDKFTISRDNAKNTLYLQMNSLRAEDTAVYYCASL

YYDYGDAYDYWGQGTLVTVSS);

and a VL domain with at least 80% sequence identity to SEQ ID NO 12

(EIVMTQSPATLSVSPGERATLSCKASQSVESNVAWYQQKPGQAPRALIY

SASLRFSGIPARFSGSGSGTEFTLTISSLQSEDFAVYYCQQYNNYPLTFG

AGTKLELK).

SEQ ID NO 11 and 12 represent the "full length" VH and VL domains of the preferred CAR. Sequences with at least 70%, preferably 80%, 85%, 90% or at least 95% sequence identity to SEQ ID NO 11 and 12, in particular when such sequence variants exhibit the desired BCMA binding specificity (functionally analogous/equivalent), are encompassed by the scope of the present invention.

In one embodiment the isolated chimeric antigen receptor (CAR) polypeptide comprising the VH and VL sequences of SEQ ID NO 11 and 12, or sequences with at least 80% identity to SEQ ID NO 11 and 12, comprises at least W36, E50, L99, Y100, Y101 and A106 of SEQ ID NO 11, and at least S31, A34, S50, L53, Q89, Y91, Y94 and L96 of SEQ ID NO 12.

The amino acid residues listed above represent those that are known to interact directly with the target BCMA epitope. The invention is therefore related to CARs in which sequence variation in the VH and VL, within at least 70%, preferably 80%, 85%, 90% or at least 95% sequence identity to SEQ ID NO 11 and 12, occurs, but the VH and VL domains comprise at least those residues known to interact with the target epitope.

In one embodiment the isolated chimeric antigen receptor (CAR) polypeptide comprising the VH and VL sequences of SEQ ID NO 11 and 12, or sequences with at least 80% identity to SEQ ID NO 11 and 12, comprises at least the CDR sequences of SEQ ID NO 1, 7, 8, 9, 5 and 10, as described herein, preferably the CDR sequences of SEQ NO 1 to 6.

The invention is therefore related to CARs in which sequence variation in the VH and VL, within at least 70%, preferably 80%, 85%, 90% or at least 95% sequence identity to SEQ ID NO 11 and 12, occurs, but the VH and VL domains comprise at least the CDR sequences as described herein. The CDRs may represent any sequence named as a CDR herein, in particular those of SEQ ID NO 1-6 or SEQ ID NO 25-30.

In a preferred embodiment the isolated chimeric antigen receptor polypeptide (CAR) of the present invention is characterised in that when said CAR is expressed in a genetically modified immune cell, preferably a T lymphocyte, said immune cell binds BCMA on the surface of a non-Hodgkin's lymphoma (B-NHL) via said CAR and is activated, thereby inducing cytotoxic activity against said B-NHL.

In a preferred embodiment the isolated chimeric antigen receptor polypeptide (CAR) of the present invention is characterised in that the B cell lymphoma is a non-Hodgkin's lymphoma (B-NHL) cell, such as DOHH-2, SU-DHL4, JEKO-1, JVM-3 and/or MEC-1 cell lines.

The CAR of the present invention is characterised by the surprising property that even very low levels of BCMA on the surface of a cell may lead to CAR binding, T cell activation and cytotoxicity against the bound cell. This represents a significant advantage compared to CARs as commonly described. Typically, a CAR requires a large number of surface antigens in order to enable activation of the CAR and subsequent cytotoxic activity. The CAR of the present invention is therefore associated with unexpected benefits in light of CARs known in the art.

The derivatization of the mouse, chimeric and/or human antibody described previously, in order to generate the CAR as described herein, may in some embodiments provide this advantage. In some embodiments the features of the BCMA epitope preferably lead to this advantage. In other embodiments the high affinity and specificity of the VH and VL fragments described herein enable the sensitivity of the present CAR. It was however unexpected that this property would arise in combination with a CAR from the earlier description of the antibodies. It was entirely surprising that the particular sequences provided herein, preferably the CDR regions of the VL and VH regions involved in binding, exhibit the specific and strong binding sufficient to enable activation of a CAR-T cell against cells with minimal BCMA expression.

It was unexpected that the VH and VL fragments described herein could be arranged in multiple configurations in the CAR as described herein and still maintain high specificity and high affinity for the target epitope. As shown below and in FIG. 3, the CAR may be configured in the VH-VL or VL-VH configuration, with variation in the linker, hinge, transmembrane domain, co-stimulatory domain and/or activation domains, and still maintain its efficacy. This surprising feature of the invention enables greater flexibility in the design of CARs directed against BCMA, thereby enabling further modification and/or optimization of the CAR structure on the basis of the VH and VL domains described herein, if any further development should be necessary or desired.

Preferred Embodiments Regarding Humanized VH and VL Domains

As disclosed in detail herein and previously (WO/2015/166073), the sequence of the antibody J22.9-xi was humanized in order to provide a more compatible reagent for administration in human subjects. Various humanized sequence variants of J22.9-xi have been generated and tested for their binding affinity and specificity to both human and cynomolgus BCMA. In preferred embodiments the CAR of the present invention incorporates these humanized sequences. The results from binding assays conducted with the corresponding antibodies demonstrate that the humanized sequences maintain the desired binding properties of the chimeric reagent J22.9-xi. In the below sequences the underlined regions represent the CDRs or putative CDRs, depending on the method used for CDR determination.

Preferred Embodiments Regarding Humanized VH Variants

Additional information is provided below on the humanized VH and VL sequences preferably incorporate by the CAR of the present invention.
Chimeric Sequence:

```
HC mouse (SEQ ID No. 38):
QVQLQQSGGGLVQPGGSLKLSCAASGIDFSRYWMSWVRRAPGKGLEWIGE

INPDSSTINYAPSLKDKFIISRDNAKNTLYLQMSKVRSEDTALYYCASLY

YDYGDAMDYWGQGTSVTVSS
```

The HC mouse sequence represents the variable region of the heavy chain (VH) originally developed for the chimeric antibody J22.9-xi, which comprises VL and VH domains obtained from a mouse antibody, capable of binding an epitope of the extracellular domain of CD269 (BCMA), and the VL and VH domains are fused to human CL and CH domains, respectively. In some embodiments the CAR may incorporate the HC mouse sequence or CDRs thereof.
Partially Humanized Sequences:

```
HC partially humanized (SEQ ID No. 39):
EVQLVESGGGLVQPGGSLRLSCAASGFTFDDYWMSWVRQAPGKGLEWVGE

INPDSSTINYAPSLKGRFTISRDNAKNTLYLQMNSLRAEDTAVYYCASLY

YDYGDAMDYWGQGTLVTVSS
```

The HC partially humanized sequence represents a modified amino acid sequence (via amino acid substitutions) in comparison to the chimeric antibody disclosed herein, whereby the VL and VH binding regions have been modified with respect to their sequence to make them more suitable for administration in humans.
Humanized VH Sequence:

```
hHC01
                                         (SEQ ID No. 40)
EVQLVESGGGLVQPGGSLRLSCAASGFTFSRYWMSWVRQAPGKGLVWVGE

INPDSSTINYAPSLKDKFTISRDNAKNTLYLQMNSLRAEDTAVYYCASLY

YDYGDAMDYWGQGTLVTVSS
```

Humanized VH Sequence with Removal of Post Translational Modification Motifs:

```
hHC02
                                         (SEQ ID No. 41)
EVQLVESGGGLVQPGGSLRLSCAASGFTFSRYWX₁SWVRQAPGKGLVWVG

EINPX₂X₃STINYAPSLKDKFTISRDNAKNTLYLQMNSLRAEDTAVYYCA

SLYX₄DYGDAX₅DYWGQGTLVTVSS
```

Wherein:
$X_1$: I, F, L, V, Y, C, G, A, S, T, preferably I or F;
$X_2X_3$: SS, NS, TS, GS, KS, RS, SD, SN, DE, preferably SS;
$X_4$: Y, L, A, V, F, I, W, preferably Y; and/or
$X_5$: Y, L, F, I, V, A, C, preferably Y;
The "hHC01" and "hHC02" humanized sequences represent preferred amino acid sequences for the present CAR that comprise sequence changes in comparison to both the original chimeric sequence and the partially humanized sequences described herein.

The PTM mutations are intended to remove potentially detrimental post translational modification motifs from said proteins, whilst maintaining the advantageous binding properties. The positions 1, 5, 6, 19, 27, 28, 34, 39, 46, 48, 54, 69, 84, 85, 86, 88, 93, 107 and/or 115 of hHC01 and hHC02 are preferably mutated (substituted) in comparison to the original chimeric sequence. The importance of the substitution relates primarily to the resulting amino acid, not the originating amino acid. The change may therefore also be carried out from the corresponding amino acid of the original chimeric amino acid or other variant, such as the partially humanized sequences.

The following substitutions are preferred in some embodiments, and differ in comparison to the chimeric (SEQ ID No 38) sequence:
the amino acid M34 of the HC (VH) sequence is substituted with any amino acid, preferably I, L, F, V, Y, C, G, A, S, T;
the amino acid E46 of the HC (VH) sequence is substituted with V;
the amino acids D54 and S55 of the HC (VH) sequence is substituted with any amino acid combination, preferably SS, TS, GS, KS, RS, SD, SN, DE;
the amino acid Y101 of the HC (VH) sequence is substituted with any amino acid, preferably L, A, V, F, I, W; and/or
the amino acid M107 of the HC (VH) sequence is substituted with any amino acid, preferably L, Y, F, I, V, A, C.

Sequences that may be modified at those residues required for direct interaction with BCMA:

```
hHC03 - modified amino acids involved in
interaction with BCMA (SEQ ID No 42):
EVQLVESGGGLVQPGGSLRLSCAASGFTFSRYX₁MX₂WVRQAPGKGLVX₃

VGX₄INPDSSTINYAPSLKDKFTISRDNAKNTLYLQMNSLRAEDTAVYYC

ASX₅X₆X₇DYGDX₈MDYWGQGTLVTVSS
```

Wherein preferred amino acids are:
$X_1$: W, F, Y, preferred W;
$X_2$: S, T, N, Q, D, E, preferred S;
$X_3$: W, F, Y, preferred W;
$X_4$: E, Q, preferred E;
$X_5$: L, I, V, G, A, preferred L;
$X_6$: Y, X, preferred Y;
$X_7$: Y, F, L, I, V, M, preferred Y; and/or
$X_8$: A, G, V, preferred A.

The "hHC03" humanized sequence represents preferred amino acid sequences that comprise amino acid sequence changes in comparison to both the original chimeric sequence and the partially humanized sequence. These sequence changes are intended to reflect potential changes in the amino acids that bind the BCMA target, which may be substituted, whilst maintaining the advantageous binding properties. The importance of the substitution relates primarily to the resulting amino acid, not the originating amino acid. The change may therefore also be carried out from the corresponding amino acid of the original chimeric amino acid or other variant.

For example:
the amino acid W33 of the HC (VH) sequence is W, F, Y;
the amino acid S35 of the HC (VH) sequence is S, T, N, Q, D, E;
the amino acid W47 of the HC (VH) sequence is W, F, Y;
the amino acid E50 of the HC (VH) sequence is E, Q;
the amino acid L99 of the HC (VH) sequence is L, I, V, G, A;
the amino acid Y100 of the HC (VH) sequence is Y, X;
the amino acid Y101 of the HC (VH) sequence is Y, F, L, I, V, M; and/or
the amino acid A106 of the HC (VH) sequence is A, G, V.

In general, any change to a CDR region made during humanization may also be considered as a feature of a CDR sequence when considered independently of the framework sequence as a whole. Such modified CDR sequences may be considered defining features of the present invention, either within or independent of their context in the entire framework region described herein. For example, the CDR sequences identified by underline in the hHC01 to hHC03 may be considered a defining feature of the invention independently of the surrounding variable region sequence.

Specific examples of humanized HC (VH) sequences:

hHC04 (SEQ ID NO 43):
EVQLVESGGGLVQPGGSLRLSCAASGFTFS<u>RYWIS</u>WVRQAPGKGLVWVGE

<u>INPNSSTINYAPSLKDKF</u>TISRDNAKNTLYLQMNSLRAEDTAVYYCA<u>SLY

YDYGDAYDY</u>WGQGTLVTVSS hHC05 (SEQ ID NO 44):
EVQLVESGGGLVQPGGSLRLSCAASGFTFS<u>RYWFS</u>WVRQAPGKGLVWVGE

<u>INPNSSTINYAPSLKDKF</u>TISRDNAKNTLYLQMNSLRAEDTAVYYCA<u>SLY

YDYGDAYDY</u>WGQGTLVTVSS hHC06 (SEQ ID NO 45):
EVQLVESGGGLVQPGGSLRLSCAASGFTFS<u>RYWIS</u>WVRQAPGKGLVWVGE

<u>INPSSSTINYAPSLKDKF</u>TISRDNAKNTLYLQMNSLRAEDTAVYYCA<u>SLY

YDYGDAYDY</u>WGQGTLVTVSS hHC07 (SEQ ID NO 46):
EVQLVESGGGLVQPGGSLRLSCAASGFTFS<u>RYWFS</u>WVRQAPGKGLVWVGE

<u>INPSSSTINYAPSLKDKF</u>TISRDNAKNTLYLQMNSLRAEDTAVYYCA<u>SLY

YDYGDAYDY</u>WGQGTLVTVSS

In order to remove a potential post-translational modification site in the humanized J22.9, residue D54 of the heavy chain CDR2 was mutated to asparagine (N), creating a new potential modification site for N-linked glycosylation (e.g. hHC04, 05). The mutated heavy chain containing N54 can be glycosylated. The corresponding IgG, J22.9-FNY, nevertheless bound BCMA in FACS and ELISA, and was crystallized in complex with BCMA. It is surprising that such a large extension of the side chain would not disrupt binding to BCMA and it could be expected from these observations that multiple and various amino acid substitutions would be tolerated at this position, potentially also derivatizations other than sugars.

Alignments:
A CLUSTAL W (1.83) multiple sequence alignment of the various substituted positions within the HC sequence provides appropriate sequence comparisons in FIG. 13. The "General sequence" represents an HC sequence, whereby each X represents a potential amino acid change to any given amino acid. Preferred amino acid substitutions are those described above for each of the potentially mutated positions.

Preferred Embodiments Regarding Humanized VL Variants

Chimeric Sequence:

LC mouse (SEQ ID No. 47):
DIVMTQSQRFMTTSVGDRVSVTC<u>KASQSVDSNVA</u>WYQQKPRQSPKALIF <u>SASLRFS</u>GVPARFTGSGSGTDFTLTISNLQSEDLAEYFC<u>QQYNNYPLT</u>F

GAGTKLELKR

The LC mouse sequence represents the variable region of the light chain (VL) originally developed for the chimeric antibody J22.9-xi, which comprises VL and VH domains obtained from a mouse antibody, capable of binding an epitope of the extracellular domain of CD269 (BCMA). In some embodiments the mouse VL domain or CDRs thereof may be employed in the CAR of the present invention.

Partially Humanized Sequences:

LC partially humanized (SEQ ID NO 48):
DIVMTQSPATLSVSVGDEVTLTC<u>KASQSVDSNVA</u>WYQQKPGQAPKLLIY <u>SDDLRFS</u>GVPARFSGSGSGTDFTLTISSLQSEDFAVYYC<u>QQYNNYPLT</u>F

GAGTKLELKR

The LC partially humanized sequence represents a modified sequence (via amino acid substitutions) in comparison to the chimeric antibody, whereby the VL and VH binding regions have been modified with respect to their sequence to make them more suitable for administration in humans.

Humanized VL Sequence:

hLC01 (SEQ ID NO 49):
EIVMTQSPATLSVSPGERATLSC<u>KASQSVDSNVA</u>WYQQKPGQ**APRALIYS

ASLRFSGIPARFSGSGSGTEFTLTISSLQSEDFAVYY**C<u>QQYNNYPLT</u>FGA

GTKLELKR

Humanized VL Sequence with Removal of Post Translational Modification Motifs:

hLC02 (SEQ ID NO 50):
EIVMTQSPATLSVSPGERATLSC<u>KASQSVX$_1$X$_2$NVA</u>WYQQKPGQAPRALI

YSASLRFSGIPARFSGSGSGTEFTLTISSLQSEDFAVYYC<u>QQYNNYPLT</u>F

GAGTKLELKR

Wherein:
$X_1X_2$: ES, SS, TS, QS, HS, DH, preferably ES.

The "hLC01" and "hLC02" humanized sequences represent preferred amino acid sequences that comprise amino acid sequence changes in comparison to both the original chimeric sequence and the partially humanized sequences described herein.

The PTM mutations are intended to remove potentially detrimental post translational modification motifs from said proteins, whilst maintaining the advantageous binding properties.

The positions 1, 8, 9, 10, 13, 15, 17, 19, 20, 21, 22, 30, 41, 43, 45, 49, 58, 63, 70, 77, 83, 85 and/or 87 of hLC01 and hLC02 are preferably mutated (substituted) in comparison to the original chimeric sequence.) The importance of the substitution relates primarily to the resulting amino acid, not the originating amino acid. The change may therefore also be carried out from the corresponding amino acid of the original chimeric amino acid or other variant.

The following substitutions are preferred and differ from the chimeric and partially humanized sequences:

- the amino acid D1 of the LC (VL) sequence is substituted with E;
- the amino acid V15 of the LC (VL) sequence is substituted with P;
- the amino acid D17 of the LC (VL) sequence is substituted with E;
- the amino acid V19 of the LC (VL) sequence is substituted with A;
- the amino acid T22 of the LC (VL) sequence is substituted with S;
- the amino acids D30 and S31 of the LC (VL) sequence is substituted with any amino acid combination, preferably ES, SS, TS, QS, HS, DH;
- the amino acid V58 of the LC (VL) sequence is substituted with I; and/or
- the amino acid D70 of the LC (VL) sequence is substituted with E.

Sequences that may be modified in their CDR binding regions at those residues required for interaction with BCMA:

hLC03 - modified amino acids involved in interaction with BCMA (SEQ ID NO 51):
EIVMTQSPATLSVSPGERATLSCKASQSVD$X_1X_2$V$X_3$W$X_4$QQKPGQAPRA

LI$X_5X_6$A$X_7X_8$R$X_9$SGIPARFSGS$X_{10}X_{11}$GTEFTLTISSLQSEDFAVYY

C$X_{12}$Q$X_{13}$NN$X_{14}$P$X_{15}$TFGAGTKLELKR

Wherein preferred amino acids are:

$X_1$: S, H, T, N, D, Q;
$X_2$: N, E, Q;
$X_3$: A, G, V, S, T, L, I;
$X_4$: Y, F, L, I, V, A, G;
$X_5$: Y, F, L;
$X_6$: S, T;
$X_7$: S, T, D, N, H, E, Q;
$X_8$: L, V, I, M;
$X_9$: F, L, I, V, Y, M;
$X_{10}$: G, X;
$X_{11}$: S, X;
$X_{12}$: Q, V, L, I, M;
$X_{13}$: Y, F, L, I, Q;
$X_{14}$: Y, F, R, Q, K; and/or
$X_{15}$: L, I, V, F.

The "hLC03 humanized sequence" represents preferred amino acid sequences that comprise amino acid sequence changes in comparison to both the original chimeric sequence and the partially humanized sequence. These sequence changes are intended to reflect potential changes in the amino acids that bind the BCMA target, which may be substituted, whilst maintaining the advantageous binding properties. The importance of the substitution relates primarily to the resulting amino acid, not the originating amino acid. The change may therefore also be carried out from the corresponding amino acid of the original chimeric amino acid or other variant.

For example:

- the amino acid S31 of the LC (VL) sequence is S, H, T, N, D, Q;
- the amino acid N32 of the LC (VL) sequence is N, E, Q;
- the amino acid A34 of the LC (VL) sequence is A, G, V, S, T, L, I;
- the amino acid Y36 of the LC (VL) sequence is Y, F, L, I, V, A, G;
- the amino acid Y49 of the LC (VL) sequence is Y, F, L;
- the amino acid S50 of the LC (VL) sequence is S, T;
- the amino acid S52 of the LC (VL) sequence is S, T, D, N, H, E, Q;
- the amino acid L53 of the LC (VL) sequence is L, V, I, M;
- the amino acid F55 of the LC (VL) sequence is F, L, I, V, Y, M;
- the amino acid G66 of the LC (VL) sequence is G, X;
- the amino acid S67 of the LC (VL) sequence is S, X;
- the amino acid Q89 of the LC (VL) sequence is Q, V, L, I, M;
- the amino acid Y91 of the LC (VL) sequence is Y, F, L, I, Q;
- the amino acid Y94 of the LC (VL) sequence is Y, F, R, Q, K; and/or
- the amino acid L96 of the LC (VL) sequence is L, I, V, F.

In general, any change to a CDR region may also be considered as a feature of a CDR sequence when considered independently of the framework sequence as a whole. Such modified CDR sequences may be considered defining features of the sequences employed herein, either within or independent of their context in the entire framework region described herein. For example, the CDR sequences identified by underline in the hLC01 to hLC03 may—in their unmodified or substituted form—be considered a defining feature of the invention independently of the surrounding variable sequences.

Example of Humanized LC Sequence hLC04 (SEQ ID NO 52):
EIVMTQSPATLSVSPGERATLSCKASQSVESNVAWYQQKPGQAPRALIYS

ASLRFSGIPARFSGSGSGTEFTLTISSLQSEDFAVYYCQQYNNYPLTFGA

GTKLELKR

Alignments:

A CLUSTAL W (1.83) multiple sequence alignment of the various potentially amended sites within the LC sequence provides appropriate sequence comparisons in FIG. 14. The "General sequence" represents an LC sequence, whereby each X represents a potential amino acid change. Preferred amino acid substitutions are those described above for each of the potentially mutated positions.

The present invention therefore relates to the humanized sequences according to hHC01, hHC02, hHC03, hHC04, hHC05, hHC06, hHC07, hLC01, hLC02, hLC03 and/or hLC04, or any given combination thereof.

All possible combinations of potential modifications for any given potentially variant residue proposed herein (as identified by X in the "general" sequence) are encompassed by the present invention. By combining one or more of these various substitutions, humanized variants may be generated that exhibit the desired binding properties of the chimeric antibody originally developed and demonstrated herein. The antibodies or parts thereof described herein also encompass a sequence with at least 80%, preferably 90%, sequence identity to those humanized sequences disclosed explicitly or disclosed through a sequence formula.

The invention further relates to CAR as described herein comprising a VH domain, wherein said VH domain comprises a sequence according to $X_1$VQL$X_2$$X_3$SGGGLVQPGGSL$X_4$LSCAASG$X_5$$X_6$ F$X_7$$X_8$YW$Z_1$SWVR$X_9$APGKGLEW$X_{10}$GEINP$Z_2$ SSTINYAPSLK$X_{11}$$X_{12}$F$X_{13}$ISRDNAKNTLYL QM$X_{14}$$X_{15}$$X_{16}$R$X_{17}$EDTA$X_{18}$YYCASLYYDY GDA$Z_3$D YWGQGT$X_{19}$VTVSS (SEQ ID No. 53),
wherein X1: Q, E; X2: Q, V; X3: Q, E; X4: K, R; X5: I, F; X6: D, T; X7: S, D; X8: R, D; X9: R, Q; X10: I, V; X11: D, G; X12: K, R; X13: I, T; X14: S, N; X15: K, S; X16: V, L; X17: S, A; X18: L, V; X19: S, L;
and wherein at least one of $Z_1$: I, F, L, V, Y, C, G, A, S, T, preferably I or F; $Z_2$: S, N, T, G, K, R, D, preferably S and/or $Z_3$: Y, L, F, I, V, A, C, preferably Y;
and wherein said antibody or fragment thereof specifically binds an epitope of the extracellular domain of CD269 (BCMA).

This embodiment encompasses various humanized sequences for the CAR of the present invention, in particular the VH sequences thereof, all variants defined by the advantageous humanization carried out in the CDRs as described herein.

The invention further relates to an antibody or antibody fragment as described herein comprising a VL domain, wherein said VL domain comprises a sequence according to DIVMTQS$X_1$$X_2$$X_3$$X_4$$X_5$$X_6$SVGDX- V$X_8$$X_g$TCKASQSVESNVAWYQQKP$X_{10}$Q$X_{11}$PK$X_{12}$ LI$X_{13}$S$X_{14}$$X_{15}$LRFSGVPARF$X_{16}$GSGSGTDFTLTI S$X_{17}$LQSED$X_{18}$A$X_{19}$ Y$X_{20}$CQQYNNYPLTFGAGTKLELK R (SEQ ID No. 54), wherein X1: Q, P; X2: R, A; X3: F, T; X4: M, L; X5: T, S; X6: T, V; X7: R, E; X8: S, T; X9: V, L; X10: R, G; X11: S, A; X12: A, L; X13: F, Y; X14: A, D; X15: S, D; X16: T, S; X17: N, S; X18: L, F; X19: E, V; X20: F, Y;
and wherein said antibody or fragment thereof specifically binds an epitope of the extracellular domain of CD269 (BCMA).

This embodiment encompasses various humanized sequences for the CAR of the present invention, in particular the VL sequences thereof, all variants defined by the advantageous humanization carried out in the CDRs as described herein.

In one embodiment the isolated chimeric antigen receptor polypeptide (CAR) of the present invention is characterised in that the extracellular antigen-binding domain comprises a linker polypeptide positioned between the VH and VL domains, wherein said linker is preferably selected from a Whitlow (SEQ ID NO 13; GSTSGSGKPGSGEGSTKG) or Gly-Ser (SEQ ID NO 14; SSGGGGSGGGGSGGGGS) linker, or linkers with at least 80% sequence identity to SEQ ID NO 13 or 14.

In one embodiment the isolated chimeric antigen receptor polypeptide (CAR) of the present invention is characterised in that said CAR comprises a spacer polypeptide positioned between the extracellular antigen-binding domain and the transmembrane domain, wherein said spacer is preferably selected from:

IgG1-CD28 spacer (SEQ ID NO 15;
PAEPKSPDKTHTCPPCPAPPVAGPSVFLFPPKPKDTLMIARTPEVTCVVV
DVSHEDPEVKFNWYVDGVEVHNAKTKPREEQYNSTYRVVSVLTVLHQDWL
NGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDK
SRWQQGNVFSCSVMHEALHNHYTQKSLSLSPGKK), IgG1Δ-4-1BB spacer (SEQ ID NO 16;
PAEPKSPDKTHTCPPCPAPPVAGPSVFLFPPKPKDTLMIARTPEVTCVVV
DVSHEDPEVKFNWYVDGVEVHNAKTKPREEQYNSTYRVVSVLTVLHQDWL
NGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDK
SRWQQGNVFSCSVMHEALHNHYTQKSLSLSPGKK), IgG4 (Hi-CH2—CH3) spacer (SEQ ID NO 17;
ESKYGPPCPPCPAPEFEGGPSVFLFPPKPKDTLMISRTPEVTCVVVDVSQ
EDPEVQFNWYVDGVEVHNAKTKPREEQFNSTYRVVSVLTVLHQDWLNGKE
YKCKVSNKGLPSSIEKTISKAKGQPREPQVYTLPPSQEEMTKNQVSLTCL
VKGFYPSDIAVEWESNGQPENNYKTTPPVLDSDGSFFLYSRLTVDKSRWQ
EGNVFSCSVMHEALHNHYTQKSLSLSLGK), IgG4 (Hi-CH3) spacer (SEQ ID NO 18;
ESKYGPPCPPCPGQPREPQVYTLPPSQEEMTKNQVSLTCLVKGFYPSDIA
VEWESNGQPENNYKTTPPVLDSDGSFFLYSRLTVDKSRWQEGNVFSCSVM
HEALHNHYTQKSLSLSLGK), IgG4 (Hi) spacer (SEQ ID NO 19;
ESKYGPPCPPCP), or a spacer with at least 80% sequence identity to any one of SEQ ID NO 15 to 19; In one embodiment the isolated chimeric antigen receptor polypeptide (CAR) of the present invention is characterised in that the transmembrane domain is preferably selected from a CD8α domain (SEQ ID NO 20; IYIWAPLAGTCGVLLLSLVITLYC) or a CD28 domain (SEQ ID NO 21; FWVLVVVGGVLACYSLLVTVAFIIFWV), or transmembrane domains with at least 80% sequence identity to SEQ ID NO 20 or 21.

In one embodiment the isolated chimeric antigen receptor polypeptide (CAR) of the present invention is characterised in that the intracellular domain comprises a co-stimulatory domain, preferably selected from a 4-1BB co-stimulatory domain (SEQ ID NO 22; KRGRKKLLYIFKQPFMRPVQTTQEEDGCSCRFPEEEEGGCEL) or a CD28 co-stimulatory domain (SEQ ID NO 23; RSKRSRLLHSDYMNMTPRRPGPTRKHYQPYAPPRDFAAYRS), or a co-stimulatory domain with at least 80% sequence identity to SEQ ID NO 22 or 23; In one embodiment the isolated chimeric antigen receptor polypeptide (CAR) of the present invention is characterised in that said CAR comprises a signaling domain, wherein said signaling domain is preferably selected from a CD3zeta (CD28 or 4-1BB) signaling domain (SEQ ID NO 24; LRVKFSRSADAPAYQQGQGQNQLYNELNLGRREEYDVLDKRRGRDPEMGGKPRRKNPQEGLY NELQKDKMAEAYSEIGMKGERRRGKGHDGLYQGLSTATKDTYDALHMQALPPR), or a signaling domain with at least 80% sequence identity to SEQ ID NO 24.

In one embodiment the isolated chimeric antigen receptor (CAR) of the present invention is characterised in that said CAR comprises a tandem co-stimulatory domain, comprising a 4-1BB co-stimulatory domain (SEQ ID NO 22) and a CD28 co-stimulatory domain (SEQ ID NO 23), and a CD3zeta signalling/activation domain (SEQ ID NO 24).

In one embodiment the isolated chimeric antigen receptor polypeptide (CAR) of the present invention is characterised in that said CAR comprises a leader sequence, wherein said leader sequence is preferably selected from the IgK leader (SEQ ID NO 55; MDFQVQIFSFLLISASVIMSR) or the GMCSF leader (SEQ ID NO 56; MLLLVTSLLLCEL-PHPAFLLI), or a leader sequence with at least 80% sequence identity to SEQ ID NO 55 or 56.

A further aspect of the invention relates to an isolated nucleic acid molecule selected from the group consisting of:
a) a nucleic acid molecule comprising a nucleotide sequence
which encodes an isolated chimeric antigen receptor (CAR) polypeptide as described herein, and/or comprising a sequence or sequence fragment of SEQ ID No. 66 and/or 67, or SEQ ID NO 86 to 94, or
b) a nucleic acid molecule which is complementary to a nucleotide sequence in accordance with a);
c) a nucleic acid molecule comprising a nucleotide sequence having sufficient sequence identity to be functionally analogous/equivalent to a nucleotide sequence according to a) or b), comprising preferably a sequence identity to a nucleotide sequence according to a) or b) of at least 80%;
d) a nucleic acid molecule which, as a consequence of the genetic code, is degenerated into a nucleotide sequence according to a) through c); and
e) a nucleic acid molecule according to a nucleotide sequence of a) through d) which is modified by deletions, additions, substitutions, translocations, inversions and/or insertions and functionally analogous/equivalent to a nucleotide sequence according to a) through d).

Preferred amino acid sequences of the present invention:

| SEQ ID No. | Sequence | Description |
|---|---|---|
| 1 | GFTFSRYW | H-CDR1 |
| 2 | INPSSSTI | H-CDR2 |
| 3 | ASLYYDYGDAYDY | H-CDR3 |
| 4 | QSVESN | L-CDR1 |
| 5 | SASX<br>Wherein X is any amino acid, preferably L, or wherein the sequence is SAS, without definition of position X | L-CDR2 |
| 6 | QQYNNYPLT | L-CDR3 |
| 7 | INPX$_2$X$_3$STI<br>wherein X$_2$X$_3$: SS, NS, TS, GS, KS, RS, SD, SN, DE | H-CDR2 |
| 8 | ASLYX$_4$DYGDAX$_5$DY<br>wherein X$_4$: Y, L, A, V, F, I, W, and/or X$_5$: Y, L, F, I, V, A, C | H-CDR3 |
| 9 | QSVX$_1$X$_2$N<br>wherein X$_1$X$_2$: ES, SS, TS, QS, HS, DH | L-CDR1 |
| 10 | QQYNNYPLTFG | L-CDR3 |
| 11 | EVQLVESGGGLVQPGGSLRLSCAASGFTFSRYWFSWVRQAPGKGLV WVGEINPSSSTINYAPSLKDKFTISRDNAKNTLYLQMNSLRAEDTAVYY CASLYYDYGDAYDYWGQGTLVTVSS | VH domain |
| 12 | EIVMTQSPATLSVSPGERATLSCKASQSVESNVAWYQQKPGQAPRALI YSASLRFSGIPARFSGSGSGTEFTLTISSLQSEDFAVYYCQQYNNYPLT FGAGTKLELK | VL domain |
| 13 | GSTSGSGKPGSGEGSTKG | Whitlow linker |
| 14 | SSGGGGSGGGGSGGGGS | Gly-Ser linker |
| 15 | PAEPKSPDKTHTCPPCPAPPVAGPSVFLFPPKPKDTLMIARTPEVTCV VVDVSHEDPEVKFNWYVDGVEVHNAKTKPREEQYNSTYRVVSVLTVL HQDWLNGKEYKCKVSNKALPAPIEKTISKAKGQPREPQVYTLPPSRDE LTKNQVSLTCLVKGFYPSDIAVEWESNGQPENNYKTTPPVLDSDGSFF LYSKLTVDKSRWQQGNVFSCSVMHEALHNHYTQKSLSLSPGKK | IgG1-CD28 spacer |
| 16 | PAEPKSPDKTHTCPPCPAPPVAGPSVFLFPPKPKDTLMIARTPEVTCV VVDVSHEDPEVKFNWYVDGVEVHNAKTKPREEQYNSTYRVVSVLTVL HQDWLNGKEYKCKVSNKALPAPIEKTISKAKGQPREPQVYTLPPSRDE LTKNQVSLTCLVKGFYPSDIAVEWESNGQPENNYKTTPPVLDSDGSFF LYSKLTVDKSRWQQGNVFSCSVMHEALHNHYTQKSLSSLSPGKK | IgG1Δ-4-1BB spacer |

| SEQ ID No. | Sequence | Description |
|---|---|---|
| 17 | ESKYGPPCPPCPAPEFEGGPSVFLFPPKPKDTLMISRTPEVTCVVVDV SQEDPEVQFNWYVDGVEVHNAKTKPREEQFNSTYRVVSVLTVLHQD WLNGKEYKCKVSNKGLPSSIEKTISKAKGQPREPQVYTLPPSQEEMTK NQVSLTCLVKGFYPSDIAVEWESNGQPENNYKTTPPVLDSDGSFFLYS RLTVDKSRWQEGNVFSCSVMHEALHNHYTQKSLSLSLGK | IgG4 (Hi-CH2—CH3) spacer |
| 18 | ESKYGPPCPPCPGQPREPQVYTLPPSQEEMTKNQVSLTCLVKGFYPS DIAVEWESNGQPENNYKTTPPVLDSDGSFFLYSRLTVDKSRWQEGNV FSCSVMHEALHNHYTQKSLSLSLGK | IgG4 (Hi-CH3) spacer |
| 19 | ESKYGPPCPPCP | IgG4 (Hi) spacer |
| 20 | IYIWAPLAGTCGVLLLSLVITLYC | CD8α domain |
| 21 | FWVLVVVGGVLACYSLLVTVAFIIFWV | CD28 domain |
| 22 | KRGRKKLLYIFKQPFMRPVQTTQEEDGCSCRFPEEEEGGCEL | 4-1BB co-stimulatory domain |
| 23 | RSKRSRLLHSDYMNMTPRRPGPTRKHYQPYAPPRDFAAYRS | CD28 co-stimulatory domain |
| 24 | LRVKFSRSADAPAYQQGQNQLYNELNLGRREEYDVLDKRRGRDPEM GGKPRRKNPQEGLYNELQKDKMAEAYSEIGMKGERRRGKGHDGLYQ GLSTATKDTYDALHMQALPPR | CD3zeta (CD28 or 4-1BB) signaling domain |
| 25 | RYWFS | H-CDR1 |
| 26 | EINPSSSTINYAPSLKDK | H-CDR2 |
| 27 | SLYYDYGDAYDYW | H-CDR3 |
| 28 | KASQSVESNVA | L-CDR1 |
| 29 | SASLRFS | L-CDR2 |
| 30 | QQYNNYPLTFG | L-CDR3 |
| 31 | MAGQCSQNEYFDSLLHACIPCQLRCSSNTPPLTCQRYCNASVTNSVK GTNALE | BCMA extracellular domain |
| 32 | MLQMAGQCSQNEYFDSLLHACIPCQLRCSSNTPPLTCQRYCNASVTN SVKGTNALE | BCMA N-terminus sequence |
| 33 | YFDSLLHACIPCQLRCSSNT | BCMA antibody epitope—amino acids 13 to 32 of BCMA |
| 34 | RYW$X_1$S<br>Wherein:<br>$X_1$: I, F, L, V, Y. C, G, A, S, T, preferably I or F | H-CDR1 |
| 35 | EINP$X_2$$X_3$STINYAPSLKDK<br>Wherein:<br>$X_2X_3$: SS, NS, TS, GS, KS, RS, SD, SN, DE, preferably SS | H-CDR2 |
| 36 | SLY$X_4$DYGDA$X_5$DYW<br>Wherein:<br>$X_4$: Y, L, A, V, F, I, W, preferably Y; and/or<br>$X_5$: Y, L, F, I, V, A, C, preferably Y | H-CDR3 |

| SEQ ID No. | Sequence | Description |
|---|---|---|
| 37 | KASQSVX₁X₂NVA<br>Wherein:<br>X₁X₂: ES, SS, TS, QS, HS, DH, preferably ES | L-CDR1 |
| 38 | QVQLQQSGGGLVQPGGSLKLSCAASGIDFSRYWMSWVRRAPGKGLE<br>WIGEINPDSSTINYAPSLKDKFIISRDNAKNTLYLQMSKVRSEDTALYYC<br>ASLYYDYGDAMDYWGQGTSVTVSS | HC (VH) mouse |
| 39 | EVQLVESGGGLVQPGGSLRLSCAASGFTFDDYWMSWVRQAPGKGLE<br>WVGEINPDSSTINYAPSLKGRFTISRDNAKNTLYLQMNSLRAEDTAVYY<br>CASLYYDYGDAMDYWGQGTLVTVSS | HC partially humanized |
| 40 | EVQLVESGGGLVQPGGSLRLSCAASGFTFSRYWMSWVRQAPGKGLV<br>WVGEINPDSSTINYAPSLKDKFTISRDNAKNTLYLQMNSLRAEDTAVYY<br>CASLYYDYGDAMDYWGQGTLVTVSS | hHC01 |
| 41 | EVQLVESGGGLVQPGGSLRLSCAASGFTFSRYWX₁SWVRQAPGKGL<br>VWVGEINPX₂X₃STINYAPSLKDKFTISRDNAKNTLYLQMNSLRAEDTAV<br>YYCASLYX₄DYGDAX₅DYWGQGTLVTVSS<br>Wherein<br>X₁: I, F, L, V, Y. C, G, A, S, T, preferably I or F;<br>X₂X₃: SS, NS, TS, GS, KS, RS, SD, SN, DE, preferably SS;<br>X₄: Y, L, A, V, F, I, W, preferably Y; and/or<br>X₅: Y, L, F, I, V, A, C, preferably Y | hHC02 |
| 42 | EVQLVESGGGLVQPGGSLRLSCAASGFTFSRYX₁MX₂WVRQAPGKGL<br>VX₃VGX₄INPDSSTINYAPSLKDKFTISRDNAKNTLYLQMNSLRAEDTAV<br>YYCASX₅X₆X₇DYGDX₈MDYWGQGTLVTVSS<br>Wherein<br>X₁: W, F, Y, preferred W;<br>X₂: S, T, N, Q, D, E, preferred S;<br>X₃: W, F, Y, preferred W;<br>X₄: E, Q, preferred E;<br>X₅: L, I, V, G, A, preferred L;<br>X₆: Y, X, preferred Y;<br>X₇: Y, F, L, I, V, M, preferred Y; and/or<br>X₈: A, G, V, preferred A | hHC03 |
| 43 | EVQLVESGGGLVQPGGSLRLSCAASGFTFSRYWISWVRQAPGKGLV<br>WVGEINPNSSTINYAPSLKDKFTISRDNAKNTLYLQMNSLRAEDTAVYY<br>CASLYYDYGDAYDYWGQGTLVTVSS | hHC04 |
| 44 | EVQLVESGGGLVQPGGSLRLSCAASGFTFSRYWFSWVRQAPGKGLV<br>WVGEINPNSSTINYAPSLKDKFTISRDNAKNTLYLQMNSLRAEDTAVYY<br>CASLYYDYGDAYDYWGQGTLVTVSS | hHC05 |
| 45 | EVQLVESGGGLVQPGGSLRLSCAASGFTFSRYWISWVRQAPGKGLV<br>WVGEINPSSSTINYAPSLKDKFTISRDNAKNTLYLQMNSLRAEDTAVYY<br>CASLYYDYGDAYDYWGQGTLVTVSS | hHC06 |
| 46 | EVQLVESGGGLVQPGGSLRLSCAASGFTFSRYWFSWVRQAPGKGLV<br>WVGEINPSSSTINYAPSLKDKFTISRDNAKNTLYLQMNSLRAEDTAVYY<br>CASLYYDYGDAYDYWGQGTLVTVSS | hHC07 |
| 47 | DIVMTQSQRFMTTSVGDRVSVTCKASQSVDSNVAWYQQKPRQSPKA<br>LIFSASLRFSGVPARFTGSGSGTDFTLTISNLQSEDLAEYFCQQYNNYP<br>LTFGAGTKLELKR | LC (VL) mouse |
| 48 | DIVMTQSPATLSVSVGDEVTLTCKASQSVDSNVAWYQQKPGQAPKLLI<br>YSDDLRFSGVPARFSGSGSGTDFTLTISSLQSEDFAVYYCQQYNNYPL<br>TFGAGTKLELKR | LC partially humanized |
| 49 | EIVMTQSPATLSVSPGERATLSCKASQSVDSNVAWYQQKPGQAPRAL<br>IYSASLRFSGIPARFSGSGSGTEFTLTISSLQSEDFAVYYCQQYNNYPL<br>TFGAGTKLELKR | hLC01 |
| 50 | EIVMTQSPATLSVSPGERATLSCKASQSVX₁X₂NVAWYQQKPGQAPRA<br>LIYSASLRFSGIPARFSGSGSGTEFTLTISSLQSEDFAVYYCQQYNNYP<br>LTFGAGTKLELKR<br>Wherein:<br>X₁X₂: ES, SS, TS, QS, HS, DH, preferably ES. | hLC02 |
| 51 | EIVMTQSPATLSVSPGERATLSCKASQSVDX₁X₂VX₃WX₄QQKPGQAPR<br>ALIX₅X₆AX₇X₈RX₉SGIPARFSGSX₁₀X₁₁GTEFTLTISSLQSEDFAVYYCX₁₂<br>QX₁₃NNX₁₄PX₁₅TFGAGTKLELKR | hLC03 |

-continued

| SEQ ID No. | Sequence | Description |
|---|---|---|
| | Wherein:<br>$X_1$: S, H, T, N, D, Q;<br>$X_2$: N, E, Q;<br>$X_3$: A, G, V, S, T, L, I;<br>$X_4$: Y, F, L, I, V, A, G;<br>$X_5$: Y, F, L;<br>$X_6$: S, T;<br>$X_7$: S, T, D, N, H, E, Q;<br>$X_8$: L, V, I, M;<br>$X_9$: F, L, I, V, Y, M;<br>$X_{10}$: G, X;<br>$X_{11}$: S, X;<br>$X_{12}$: Q, V, L, I, M;<br>$X_{13}$: Y, F, L, I, Q;<br>$X_{14}$: Y, F, R, Q, K; and/or<br>$X_{15}$: L, I, V, F | |
| 52 | EIVMTQSPATLSVSPGERATLSCKASQSVESNVAWYQQKPGQAPRALI<br>YSASLRFSGIPARFSGSGSGTEFTLTISSLQSEDFAVYYCQQYNNYPLT<br>FGAGTKLELKR | hLC04 |
| 53 | $X_1$VQLX$_2$X$_3$SGGGLVQPGGSLX$_4$LSCAASGX$_5$X$_6$FX$_7$X$_8$YWZ$_1$SWVRX$_9$AP<br>GKGLEWX$_{10}$GEINPZ$_2$SSTINYAPSLKX$_{11}$X$_{12}$FX$_{13}$ISRDNAKNTLYLQMX$_{14}$<br>X$_{15}$X$_{16}$RX$_{17}$EDTAX$_{18}$YYCASLYYDYGDAZ$_3$DYWGQGTX$_{19}$VTVSS<br>wherein X1: Q, E; X2: Q, V; X3: Q, E; X4: K, R; X5: I, F; X6: D, T; X7: S,<br>D; X8: R, D; X9: R, Q; X10: I, V; X11: D, G; X12: K, R; X13: I, T; X14: S,<br>N; X15: K, S; X16: V, L; X17: S, A; X18: L, V; X19: S, L;<br>and wherein at least one of Z$_1$: I, F, L, V, Y. C, G, A, S, T, preferably I<br>or F; Z$_2$: S, N, T, G, K, R, D, preferably S and/or Z$_3$: Y, L, F, I, V, A, C,<br>preferably Y; | VH hum Gen |
| 54 | DIVMTQSX$_1$X$_2$X$_3$X$_4$X$_5$X$_6$SVGDX$_7$VX$_8$X$_9$TCKASQSVESNVAWYQQKPX$_{10}$<br>QX$_{11}$PKX$_{12}$LIX$_{13}$SX$_{14}$X$_{15}$LRFSGVPARFX$_{16}$GSGSGTDFTLTISX$_{17}$LQSED<br>X$_{18}$AX$_{19}$YX$_{20}$CQQYNNYPLTFGAGTKLELKR<br>wherein X1: Q, P; X2: R, A; X3: F, T; X4: M, L; X5: T, S; X6: T, V; X7: R,<br>E; X8: S, T; X9: V, L; X10: R, G; X11: S, A; X12: A, L; X13: F, Y; X14: A,<br>D; X15: S, D; X16: T, S; X17: N, S; X18: L, F; X19: E, V; X20: F, Y; | VL hum Gen |
| 55 | MDFQVQIFSFLLISASVIMSR | IgK leader |
| 56 | MLLLVTSLLLCELPHPAFLLI | GMCSF leader |
| 57 | MDFQVQIFSFLLISASVIMSREVQLVESGGGLVQPGGSLRLSCAASGF<br>TFSRYWFSWVRQAPGKGLVWVGEINPSSSTINYAPSLKDKFTISRDNA<br>KNTLYLQMNSLRAEDTAVYYCASLYYDYGDAYDYWGQGTLVTVSSGS<br>TSGSGKPGSGEGSTKGEIVMTQSPATLSVSPGERATLSCKASQSVES<br>NVAWYQQKPGQAPRALIYSASLRFSGIPARFSGSGSGTEFTLTISSLQS<br>EDFAVYYCQQYNNYPLTFGAGTKLELKPAEPKSPDKTHTCPPCPAPP<br>VAGPSVFLFPPKPKDTLMIARTPEVTCVVVDVSHEDPEVKFNWYVDGV<br>EVHNAKTKPREEQYNSTYRVVSVLTVLHQDWLNGKEYKCKVSNKALP<br>APIEKTISKAKGQPREPQVYTLPPSRDELTKNQVSLTCLVKGFYPSDIA<br>VEWESNGQPENNYKTTPPVLDSDGSFFLYSKLTVDKSRWQQGNVFS<br>CSVMHEALHNHYTQKSLSLSPGKKDPKFWVLVVVGGVLACYSLLVTV<br>AFIIFWVRSKRSRLLHSDYMNMTPRRPGPTRKHYQPYAPPRDFAAYR<br>SLRVKFSRSADAPAYQQGQNQLYNELNLGRREEYDVLDKRRGRDPE<br>MGGKPRRKNPQEGLYNELQKDKMAEAYSEIGMKGERRRGKGHDGLY<br>QGLSTATKDTYDALHMQALPPR | Construct IX<br>IX_MP71-<br>hBCMA-VH-<br>WL-<br>VL_IgG1_CD28_CD3z |
| 58 | MDFQVQIFSFLLISASVIMSREIVMTQSPATLSVSPGERATLSCKASQS<br>VESNVAWYQQKPGQAPRALIYSASLRFSGIPARFSGSGSGTEFTLTISS<br>LQSEDFAVYYCQQYNNYPLTFGAGTKLELKGSTSGSGKPGSGEGSTK<br>GEVQLVESGGGLVQPGGSLRLSCAASGFTFSRYWFSWVRQAPGKGL<br>VWVGEINPSSSTINYAPSLKDKFTISRDNAKNTLYLQMNSLRAEDTAVY<br>YCASLYYDYGDAYDYWGQGTLVTVSSPAEPKSPDKTHTCPPCPAPPV<br>AGPSVFLFPPKPKDTLMIARTPEVTCVVVDVSHEDPEVKFNWYVDGVE<br>VHNAKTKPREEQYNSTYRVVSVLTVLHQDWLNGKEYKCKVSNKALPA<br>PIEKTISKAKGQPREPQVYTLPPSRDELTKNQVSLTCLVKGFYPSDIAV<br>EWESNGQPENNYKTTPPVLDSDGSFFLYSKLTVDKSRWQQGNVFSC<br>SVMHEALHNHYTQKSLSLSPGKKDPKFWVLVVVGGVLACYSLLVTVA<br>FIIFWVRSKRSRLLHSDYMNMTPRRPGPTRKHYQPYAPPRDFAAYRSL<br>RVKFSRSADAPAYQQGQNQLYNELNLGRREEYDVLDKRRGRDPEMG<br>GKPRRKNPQEGLYNELQKDKMAEAYSEIGMKGERRRGKGHDGLYQG<br>LSTATKDTYDALHMQALPPR | Construct X<br>X_MP71-<br>hBCMA-VL-<br>WL-<br>VH_IgG1_CD28_CD3z |

-continued

| SEQ ID No. | Sequence | Description |
|---|---|---|
| 59 | MDFQVQIFSFLLISASVIMSREVQLVESGGGLVQPGGSLRLSCAASGF TFSRYWFSWVRQAPGKGLVWVGEINPSSSTINYAPSLKDKFTISRDNA KNTLYLQMNSLRAEDTAVYYCASLYYDYGDAYDYWGQGTLVTVSSGS TSGSGKPGSGEGSTKGEIVMTQSPATLSVSPGERATLSCKASQSVES NVAWYQQKPGQAPRALIYSASLRFSGIPARFSGSGSGTEFTLTISSLQS EDFAVYYCQQYNNYPLTFGAGTKLELKPAEPKSPDKTHTCPPCPAPP VAGPSVFLFPPKPKDTLMIARTPEVTCVVVDVSHEDPEVKFNWYVDGV EVHNAKTKPREEQYNSTYRVVSVLTVLHQDWLNGKEYKCKVSNKALP APIEKTISKAKGQPREPQVYTLPPSRDELTKNQVSLTCLVKGFYPSDIA VEWESNGQPENNYKTTPPVLDSDGSFFLYSKLTVDKSRWQQGNVFS CSVMHEALHNHYTQKSLSLSPGKKDPKFWVLVVVGGVLACYSLLVTV AFIIFWVRSKRSRLLHSDYMNMTPRRPGPTRKHYQPYAPPRDFAAYR SLRVKFSRSADAPAYQQGQNQLYNELNLGRREEYDVLDKRRGRDPE MGGKPRRKNPQEGLYNELQKDKMAEAYSEIGMKGERRRGKGHDGLY QGLSTATKDTYDALHMQALPPR | Construct XI XI_MP71- hBCMA-VH- WL- VL_IgG1_CD28_CD3z_no_opt |
| 60 | MDFQVQIFSFLLISASVIMSREVQLVESGGGLVQPGGSLRLSCAASGF TFSRYWFSWVRQAPGKGLVWVGEINPSSSTINYAPSLKDKFTISRDNA KNTLYLQMNSLRAEDTAVYYCASLYYDYGDAYDYWGQGTLVTVSSGS TSGSGKPGSGEGSTKGEIVMTQSPATLSVSPGERATLSCKASQSVES NVAWYQQKPGQAPRALIYSASLRFSGIPARFSGSGSGTEFTLTISSLQS EDFAVYYCQQYNNYPLTFGAGTKLELKESKYGPPCPPCPAPEFEGGP SVFLFPPKPKDTLMISRTPEVTCVVVDVSQEDPEVQFNWYVDGVEVH NAKTKPREEQFNSTYRVVSVLTVLHQDWLNGKEYKCKVSNKGLPSSIE KTISKAKGQPREPQVYTLPPSQEEMTKNQVSLTCLVKGFYPSDIAVEW ESNGQPENNYKTTPPVLDSDGSFFLYSRLTVDKSRWQEGNVFSCSVM HEALHNHYTQKSLSLSLGKFWVLVVVGGVLACYSLLVTVAFIIFWVRSK RSRLLHSDYMNMTPRRPGPTRKHYQPYAPPRDFAAYRSLRVKFSRSA DAPAYQQGQNQLYNELNLGRREEYDVLDKRRGRDPEMGGKPRRKNP QEGLYNELQKDKMAEAYSEIGMKGERRRGKGHDGLYQGLSTATKDTY DALHMQALPPR | Construct XII XII_new_cuts_MP71- hBCMA- VH-WL- VL_IgG4_CD28_CD3z |
| 61 | MDFQVQIFSFLLISASVIMSREVQLVESGGGLVQPGGSLRLSCAASGF TFSRYWFSWVRQAPGKGLVWVGEINPSSSTINYAPSLKDKFTISRDNA KNTLYLQMNSLRAEDTAVYYCASLYYDYGDAYDYWGQGTLVTVSSGS TSGSGKPGSGEGSTKGEIVMTQSPATLSVSPGERATLSCKASQSVES NVAWYQQKPGQAPRALIYSASLRFSGIPARFSGSGSGTEFTLTISSLQS EDFAVYYCQQYNNYPLTFGAGTKLELKESKYGPPCPPCPGQPREPQV YTLPPSQEEMTKNQVSLTCLVKGFYPSDIAVEWESNGQPENNYKTTP PVLDSDGSFFLYSRLTVDKSRWQEGNVFSCSVMHEALHNHYTQKSLS LSLGKFWVLVVVGGVLACYSLLVTVAFIIFWVRSKRSRLLHSDYMNMT PRRPGPTRKHYQPYAPPRDFAAYRSLRVKFSRSADAPAYQQGQNQL YNELNLGRREEYDVLDKRRGRDPEMGGKPRRKNPQEGLYNELQKDK MAEAYSEIGMKGERRRGKGHDGLYQGLSTATKDTYDALHMQALPPR | Construct XIII XIII_new_cuts_MP71- hBCMA-VH- WL- VL_IgG4_HI_CH3_CD28_CD3z |
| 62 | MDFQVQIFSFLLISASVIMSREVQLVESGGGLVQPGGSLRLSCAASGF TFSRYWFSWVRQAPGKGLVWVGEINPSSSTINYAPSLKDKFTISRDNA KNTLYLQMNSLRAEDTAVYYCASLYYDYGDAYDYWGQGTLVTVSSGS TSGSGKPGSGEGSTKGEIVMTQSPATLSVSPGERATLSCKASQSVES NVAWYQQKPGQAPRALIYSASLRFSGIPARFSGSGSGTEFTLTISSLQS EDFAVYYCQQYNNYPLTFGAGTKLELKESKYGPPCPPCPFWVLVVVG GVLACYSLLVTVAFIIFWVRSKRSRLLHSDYMNMTPRRPGPTRKHYQP YAPPRDFAAYRSLRVKFSRSADAPAYQQGQNQLYNELNLGRREEYDV LDKRRGRDPEMGGKPRRKNPQEGLYNELQKDKMAEAYSEIGMKGER RRGKGHDGLYQGLSTATKDTYDALHMQALPPR | Construct XIV XIV_new_cuts_MP71- hBCMA-VH- WL- VL_IgG4_HI_CD28_CD3z |
| 63 | MDFQVQIFSFLLISASVIMSREVQLVESGGGLVQPGGSLRLSCAASGF TFSRYWFSWVRQAPGKGLVWVGEINPSSSTINYAPSLKDKFTISRDNA KNTLYLQMNSLRAEDTAVYYCASLYYDYGDAYDYWGQGTLVTVSSGS TSGSGKPGSGEGSTKGEIVMTQSPATLSVSPGERATLSCKASQSVES NVAWYQQKPGQAPRALIYSASLRFSGIPARFSGSGSGTEFTLTISSLQS EDFAVYYCQQYNNYPLTFGAGTKLELKPAEPKSPDKTHTCPPCPAPP VAGPSVFLFPPKPKDTLMIARTPEVTCVVVDVSHEDPEVKFNWYVDGV EVHNAKTKPREEQYNSTYRVVSVLTVLHQDWLNGKEYKCKVSNKALP APIEKTISKAKGQPREPQVYTLPPSRDELTKNQVSLTCLVKGFYPSDIA VEWESNGQPENNYKTTPPVLDSDGSFFLYSKLTVDKSRWQQGNVFS CSVMHEALHNHYTQKSLSLSPGKKIYIWAPLAGTCGVLLLSLVITLYC KRGRKKLLYIFKQPFMRPVQTTQEEDGCSCRFPEEEEGGCELLRVKF SRSADAPAYQQGQNQLYNELNLGRREEYDVLDKRRGRDPEMGGKPR RKNPQEGLYNELQKDKMAEAYSEIGMKGERRRGKGHDGLYQGLSTA TKDTYDALHMQALPPR | Construct XV XV_MP71- hBCMA-VH- WL- VL_IgGdelta_CD8_4- 1BB_CD3z |
| 64 | MDFQVQIFSFLLISASVIMSREIVMTQSPATLSVSPGERATLSCKASQS VESNVAWYQQKPGQAPRALIYSASLRFSGIPARFSGSGSGTEFTLTISS LQSEDFAVYYCQQYNNYPLTFGAGTKLELKGSTSGSGKPGSGEGSTK | Construct XVI XVI_MP71- hBCMA-VL- |

| SEQ ID No. | Sequence | Description |
|---|---|---|
|  | GEVQLVESGGGLVQPGGSLRLSCAASGFTFSRYWFSWVRQAPGKGL<br>VWVGEINPSSSTINYAPSLKDKFTISRDNAKNTLYLQMNSLRAEDTAVY<br>YCASLYYDYGDAYDYWGQGTLVTVSSPAEPKSPDKTHTCPPCPAPPV<br>AGPSVFLFPPKPKDTLMIARTPEVTCVVVDVSHEDPEVKFNWYVDGVE<br>VHNAKTKPREEQYNSTYRVVSVLTVLHQDWLNGKEYKCKVSNKALPA<br>PIEKTISKAKGQPREPQVYTLPPSRDELTKNQVSLTCLVKGFYPSDIAV<br>EWESNGQPENNYKTTPPVLDSDGSFFLYSKLTVDKSRWQQGNVFSC<br>SVMHEALHNHYTQKSLSSLSPGKKIYIWAPLAGTCGVLLLSLVITLYCK<br>RGRKKLLYIFKQPFMRPVQTTQEEDGCSCRFPEEEEGGCELLRVKFS<br>RSADAPAYQQGQNQLYNELNLGRREEYDVLDKRRGRDPEMGGKPRR<br>KNPQEGLYNELQKDKMAEAYSEIGMKGERRRGKGHDGLYQGLSTAT<br>KDTYDALHMQALPPR | WL-<br>VH_IgGdelta_CD8_4-<br>1BB_CD3z |
| 65 | MDFQVQIFSFLLISASVIMSREVQLVESGGGLVQPGGSLRLSCAASGF<br>TFSRYWFSWVRQAPGKGLVWVGEINPSSSTINYAPSLKDKFTISRDNA<br>KNTLYLQMNSLRAEDTAVYYCASLYYDYGDAYDYWGQGTLVTVSSGS<br>TSGSGKPGSGEGSTKGEIVMTQSPATLSVSPGERATLSCKASQSVES<br>NVAWYQQKPGQAPRALIYSASLRFSGIPARFSGSGSGTEFTLTISSLQS<br>EDFAVYYCQQYNNYPLTFGAGTKLELKPAEPKSPDKTHTCPPCPAPP<br>VAGPSVFLFPPKPKDTLMIARTPEVTCVVVDVSHEDPEVKFNWYVDGV<br>EVHNAKTKPREEQYNSTYRVVSVLTVLHQDWLNGKEYKCKVSNKALP<br>APIEKTISKAKGQPREPQVYTLPPSRDELTKNQVSLTCLVKGFYPSDIA<br>VEWESNGQPENNYKTTPPVLDSDGSFFLYSKLTVDKSRWQQGNVFS<br>CSVMHEALHNHYTQKSLSSLSPGKKIYIWAPLAGTCGVLLLSLVITLYC<br>KRGRKKLLYIFKQPFMRPVQTTQEEDGCSCRFPEEEEGGCELLRVKF<br>SRSADAPAYQQGQNQLYNELNLGRREEYDVLDKRRGRDPEMGGKPR<br>RKNPQEGLYNELQKDKMAEAYSEIGMKGERRRGKGHDGLYQGLSTA<br>TKDTYDALHMQALPPR | Construct XVII<br>XVII_MP71-<br>hBCMA-VH-<br>WL-<br>VL_IgGdelta_CD8_4-<br>1BB_CD3z_no_opt |

Preferred nucleotide sequences:

| | | |
|---|---|---|
| 66 | gaggtgcagctggtggaatctggcggaggactggtgcagcctggcggctctctgagactgtcttgtgc<br>cgccagcggcttcaccttcagccggtactggtttagctgggtgcgccaggcccctggcaagggactcg<br>tgtgggtgggagagatcaaccccagcagcagcaccatcaactacgccccagcctgaaggacaa<br>gttcaccatcagcagagacaacgccaagaacaccctgtacctgcagatgaacagcctgcgggccg<br>aggcaccgccgtgtactattgtgccagcctgtactacgactacggcgacgcctacgattactgggc<br>cagggcacactggtgactgttagctcc | Codon<br>optimized VH |
| 67 | Gagatcgtgatgacacagagccctgccaccctgagcgtgtccccaggcgaaagagctaccctgag<br>ctgcaaggccagccagagcgtggaaagcaacgtggcctggtatcagcagaaacccggacaggct<br>cctcgggccctgatctacagcgccagcctgagattcagcggcatccccgccaggtttagcggctctgg<br>cagcggcaccgagttcaccctgacaatcagcagcctgcagagcgaggactttgccgtgtattactgc<br>cagcagtacaacaactacccccctgaccttcggagccggcaccaagctggagctgaag | Codon<br>optimized VL |
| 68 | gaagtgcagctggtcgaatctggaggaggcctggttcagcctggtggcagccttaggctctcttgtgca<br>gcctctggctttaccttctcacggtattggttcagctgggtgagacaggctccagggaaaggtctggtgt<br>gggtaggggagataaaccccagcagcagcacgatcaactatgctccgtcactgaaagacaagttc<br>accatttcccgcgataatgccaagaacactctctacttgcagatgaattcccttcgagccgaggataca<br>gcggtgtactactgcgcagtctgtactacgactatggggacgcatacgactattggggacaaggca<br>cactggtgactgttagctcc | VH without<br>Codon<br>Optimization -<br>mAb scFv |
| 69 | Gagatcgtgatgacccagtctcctgctaccctgagcgtttctcccggtgaaagggccacactcagctg<br>caaagcctctcaaagcgtgggagagcaatgtgcctggtatcagcagaaacctggccaagctccgag<br>agcactgatctattccgcgtcattgcgcttttccggcataccagcacggtttagtggctcagggagtggg<br>actgagttcactctgacgattagctcccttcagtcagaggatttcgccgtgtactactgtcagcagtacaa<br>caactatcccctcacattcggagctggaaccaagctggaactgaag | VL without<br>Codon<br>Optimization -<br>mAb scFv |
| 70 | atggatttccaggtgcagatcttcagcttcctgctgatctccgccagcgtgatcatgagccgc | IgK leader |
| 71 | atgcttctcctggtgacaagccttctgctctgtgagttaccacacccagcattcctcctgatc | GMCSF leader |
| 72 | ggcagcaccagcggctccggcaagcctggctctggcgagggcagcacaaaggga | Whitlow linker |
| 73 | tctagcggcggaggcggatctggcggggaggatctggggaggcggctct | Gly-Ser linker |
| 74 | Cctgccgagcctaagagccccgacaagacccacacctgtcccccttgtcctgccctccagtggctg<br>gccctagcgtgttcctgttccccccaaagccaaggtaccctgatgatcgcccggaccccgaagtc<br>acatgcgtggtggtggacgtgagccacgaagaccctgaggtcaagttcaactggtacgtggacggc<br>gtggaggtgcataatgccaagacaaagccgcggggaggagcagtacaacagcacgtaccgtgtggt<br>cagcgtcctcaccgtcctgcaccaggactggctgaatggcaaggagtacaagtgcaaggtctccaa<br>caaagccctcccagcccccatcgagaaaaccatctccaaagccaaagggcagccccgagaacc<br>acaggtgtacaccctgcccccatcccgggatgagctgaccaagaaccaggtcagcctgacctgcct | IgG1 - CD28<br>Backbone<br>spacer |

| | | |
|---|---|---|
| | ggtcaaaggcttctatcccagcgacatcgccgtggagtgggagagcaatgggcagccggagaaca<br>actacaagaccacgcctcccgtgctggactccgacggctccttcttcctctacagcaagctcaccgtgg<br>acaagagcaggtggcagcaggggaacgtcttctcatgctccgtgatgcatgaggctctgcacaacca<br>ctacacgcagaagagcctctccctgtctccgggtaaaaaa | |
| 75 | Cctgccgagcctaagagccccgacaagacccacacctgtcccccttgtcctgcccctccagtggctg<br>gccctagcgtgttcctgttccccccaaagcccaaggatacccctgatgatcgcccggaccccccgaagtc<br>acatgcgtggtggtggacgtgagccacgaagaccctgaggtcaagttcaactggtacgtggacggc<br>gtggaggtgcataatgccaagacaaagccgcgggaggagcagtacaacagcacgtaccgtgtggt<br>cagcgtcctcaccgtcctgcaccaggactggctgaatggcaaggagtacaagtgcaaggtctccaa<br>caaagcccctcccagcccccatcgagaaaaccatctctccaaagccaaagggcagccccgagaacc<br>acaggtgtaccaccctgcccccatcccgggatgagctgaccaagaaccaggtgtcctgacctgcctc<br>gtgaagggcttctaccctcgatatcgccgtggaatgggagagcaatggccagcccgagaacaac<br>tacaagaccaccccccctgtgctggacagcgacggctcattcttcctgtacagcaagctgacagtgga<br>caagagccggtggcagcaggggaacgtgttcagctgcagcgtgatgcacgaggctctgcacaacc<br>actacacccagaagtccctgagcagcctgagcccaggcaagaag | IgG1Δ-4-<br>1BB Backbone<br>spacer |
| 76 | Gagagcaagtacggccctccctgcccccttgccctgccccgagttcgagggcggaccccagcgtg<br>ttcctgttccccccaagcccaaggacaccctgatgatcagccggaccccgaggtgacctgcgtgg<br>tggtggacgtgagccaggaagatcccgaggtccagttcaattggtacgtggacggcgtgaagtgca<br>caacgccaagaccaagcccagagaggaacagttcaacagcacctaccgggtggtgtctgtgctga<br>ccgtgctgcaccaggactggctgaacggcaaagaatacaagtgcaaggtgtccaacaagggcctg<br>cccagcagcatcgaaaagaccatcagcaaggccaagggcagcctcgcgagcccaggtgtaca<br>ccctgcctcccttcccaggaagagatgaccaagaaccaggtgtccctgacctgcctggtgaagggctt<br>ctaccccagcgacatcgccgtggagtgggagagcaatggccagcctgagaacaactacaagacc<br>accccccgtgctggacagcgacggcagcttcttcctctacagccggctgaccgtggacaagagcc<br>ggtggcaggaaggcaacgtcttttagctgcagcgtgatgcacgaggccctgcacaaccactacaccc<br>agaaagagcctgagcctgtccctgggcaag | IgG4 (Hi-CH2—CH3)<br>spacer |
| 77 | Gagagcaagtacggccctccctgcccccttgccctggccagcctcgcgagcccaggtgtacacc<br>ctgcctcccctcccaggaagagatgaccaagaaccaggtgtccctgacctgcctggtgaagggcttct<br>accccagcgacatcgccgtggagtgggagagcaatggccagcctgagaacaactacaagacca<br>cccctcccgtgctggacagcgacggcagcttcttcctctacagccggctgaccgtggacaagagccg<br>gtggcaggaaggcaacgtcttttagctgcagcgtgatgcacgaggccctgcacaaccactacaccca<br>gaagagcctgagcctgtccctgggcaag | IgG4 (Hi-CH3)<br>spacer |
| 78 | Gagagcaagtacggccctccctgccccccttgccct | IgG4 (Hi)<br>spacer |
| 79 | Atctacatctgggcccctctggccggcacctgtggcgtgctgctgctgtctctcgtgatcacactgtactgc | CD8α<br>transmembrane<br>domain |
| 80 | Ttttgggtgctggtggtggttggtggagtcctggcttgctatagcttgctagtaacagtggcctttattattttc<br>tgggtg | CD28<br>transmembrane<br>domain |
| 81 | aagcggggcagaaagaagctgctgtacatcttcaagcagcccttcatgcggcccgtgcagaccacc<br>caggaagaggacggctgctcctgcagattccccgaggaagaagaaggcggctgcgagctg | 4-1BB Co-<br>stimulatory<br>domain |
| 82 | Aggagtaagaggagcaggctcctgcacagtgactacatgaacatgactccccgccgccccgggcc<br>caccccgcaagcattaccagcccctatgccccaccacgcgacttcgcagcctatcgctcc | CD28<br>(constructs IX-XI)<br>Co-<br>stimulatory<br>domain |
| 83 | Aggagtaagaggagcaggctcctgcacagtgactacatgaacatgactccccgtcgacccgggcc<br>caccccgcaagcattaccagcccctatgccccaccacgcgacttcgcagcctatcgctcc | CD28<br>(constructs XII-XIV)<br>(additional<br>cleavage site<br>for SalI added)<br>Co-stimulatory<br>domain |
| 84 | Ctgagagtgaagttcagcaggagcgcagacgcccccgcgtaccagcagggccagaaccagctct<br>ataacgagctcaatctaggacgaagagaggagtacgatgttttggacaagagacgtggccgggac<br>cctgagatggggggaaagccgagaaggaagaaccctcaggaaggcctgtacaatgaactgcaga<br>aagataagatggccgaggcctacagtgagattgggatgaaaggcgagcgccgggaggcaagg<br>ggcacgatggcctttaccagggtctcagtacagccaccaaggacacctacgacgcccttcacatgca<br>ggccctgccccctcgctga | CD3zeta<br>(CD28)<br>Signaling<br>domain |
| 85 | ctgcgcgtgaagttttctagaagcgccgacgcccctgcctaccagcagggccagaaccagctgtaca<br>acgagctgaacctgggcagacgagaagagtacgacgtgctggataagagggagaggccgggacc<br>ctgagatgggcggcaagcctagaagaaagaaccccaggaaggcctgtataacgaactgcagaa<br>agacaagatggccgaggcctacagcgagatcggaatgaagggcgagcggagaaggaggcaagg<br>gccacgatggactgtaccagggcctgagcaccgccaccaaggacacctatgacgccctgcacatg<br>caggctctgccccccaga | CD3zeta (4-<br>1BB) Signaling<br>domain |

-continued

| | | |
|---|---|---|
| 86 | atggatttccaggtgcagatcttcagcttcctgctgatctccgccagcgtgatcatgagccgcgaggtgc<br>agctggtggaatctggcggaggactggtgcagcctggcggctctctgagactgtcttgtgccgccagc<br>ggcttcaccttcagccggtactggtttagctgggtgcgccaggcccctggcaagggactcgtgtgggtg<br>ggagagatcaacccagcagcagcaccatcaactacgcccccagcctgaaggacaagttcaccat<br>cagcagagacaacgccaagaacaccctgtacctgcagatgaacagcctgcgggccgaggacac<br>cgccgtgtactattgtgccagcctgtactacgactacggcgacgcctacgattactggggccagggca<br>cactggtgactgttagctccggcagcaccagcggctccggcaagcctggctctggcgagggcagca<br>aaagggagagatcgtgatgacacagagccctgccacccctgagcgtgtcccaggcgaaagagct<br>accctgagctgcaaggccagccagagcgtggaaagcaacgtggcctggtatcagcagaagcccg<br>gacagcctcctcgggccctgatctacagcgccagcctgagattcagcggcatccccgccaggtttag<br>cggctctggcagcggcaccgagttcaccctgacaatcagcagcctgcagagcgaggactttgccgt<br>gtattactgccagcagtacaacaactacccccctgaccttcggagccggcaccaagctggagctgaa<br>gcctgccgagcctaagagccccgacaagacccacacctgtccccttgtcctgccctccagtggct<br>ggccctagcgtgttcctgttccccccaaagcccaaggataccctgatgatcgcccggaccccgaag<br>tcacatgcgtggtggtggacgtgagccacgaagacctgaggtcaagttcaactggtacgtggacgg<br>cgtggaggtgcataatgccaagacaaagccgcggaggagcagtacaacagcacgtaccgtgtg<br>gtcagcgtcctcaccgtcctgcaccaggactggctgaatggcaaggagtacaagtgcaaggtctcca<br>acaaagcccctccagccccatcgagaaaaccatctccaaagccaaagggcagccccgagaac<br>cacaggtgtacaccctgcccccatcccgggatgagctgaccaagaaccaggtcagcctgacctgcc<br>tggtcaaaggcttctatcccagcgacatcgccgtggagtgggagagcaatgggcagccgagaac<br>aactacaagaccacgcctccgtgctggactccgacggctccttcttcctctacagcaagctcaccgtg<br>gacaagagcaggtggcagcaggggaacgtcttctcatgctccgtgatgcatgaggctctgcacaacc<br>actacacgcagaagagcctctccctgtctccgggtaaaaaagatcccaaattttgggtgctggtggtg<br>gttggtggagtcctggcttgctatagcttgctagtaacagtggcctttattattttctgggtgaggagtaaga<br>ggagcaggctcctgcacagtgactacatgaacatgactccccgccgcccgggcccacccgcaag<br>cattaccagcctatgccccaccacgcgacttcgcagcctatcgctccctgagagtgaagttcagcag<br>gagcgcagacgcccccgcgtaccagcagggccagaaccagctctataacgagctcaatctaggac<br>gaagagaggagtacgatgtttttggacaagagacgtggccgggaccctgagatgggggaaagcc<br>gagaaggaagaaccctcaggaaggcctgtacaatgaactgcagaaagataagatggcggaggc<br>ctacagtgagattgggatgaaaggcgagcgccggaggggcaaggggcacgatggcctttaccagg<br>gtctcagtacagccaccaaggacacctacgacgcccttcacatgcaggccctgccccctcgctga | Construct IX<br>IX_MP71-<br>hBCMA-VH-<br>WL-<br>VL_IgG1_CD28_CD3z |
| 87 | atggatttccaggtgcagatcttcagcttcctgctgatctccgccagcgtgatcatgagccgcgagatcg<br>tgatgacacagagccctgccacccctgagcgtgtcccaggcgaaagagctaccctgagctgcaag<br>gccagccagagcgtggaaagcaacgtggcctggtatcagcagaagcccggacagcctcctcggg<br>ccctgatctacagcgccagcctgagattcagcggcatccccgccaggtttagcggctctggcagcgg<br>caccgagttcaccctgacaatcagcagcctgcagagcgaggactttgccgtgtattactgccagcagt<br>acaacaactacccccctgaccttcggagccggcaccaagctggagctgaagggcagcaccagcgg<br>ctccggcaagcctggctctggcgagggcagcacaaagggagagatcgtgcagctggtggaatctgcg<br>gaggactggtgcagcctggcggctctctgagactgtcttgtgccgccagcggcttcaccttcagccggt<br>actggtttagctgggtgcgccaggcccctggcaagggactcgtgtgggtgggagagatcaaccca<br>gcagcagcaccatcaactacgcccccagcctgaaggacaagttcaccatcagcagagacaacgc<br>caagaacaccctgtacctgcagatgaacagcctgcgggccgaggacaccgccgtgtactattgtgc<br>cagcctgtactacgactacggcgacgcctacgattactggggccagggcacactggtgactgttagct<br>cccctgccgagcctaagagccccgacaagacccacacctgtccccttgtcctgccctccagtggct<br>ggccctagcgtgttcctgttccccccaaagcccaaggataccctgatgatcgcccggaccccgaag<br>tcacatgcgtggtggtggacgtgagccacgaagacctgaggtcaagttcaactggtacgtggacgg<br>cgtggaggtgcataatgccaagacaaagccgcggaggagcagtacaacagcacgtaccgtgtg<br>gtcagcgtcctcaccgtcctgcaccaggactggctgaatggcaaggagtacaagtgcaaggtctcca<br>acaaagcccctccagccccatcgagaaaaccatctccaaagccaaagggcagccccgagaac<br>cacaggtgtacaccctgcccccatcccgggatgagctgaccaagaaccaggtcagcctgacctgcc<br>tggtcaaaggcttctatcccagcgacatcgccgtggagtgggagagcaatgggcagccgagaac<br>aactacaagaccacgcctccgtgctggactccgacggctccttcttcctctacagcaagctcaccgtg<br>gacaagagcaggtggcagcaggggaacgtcttctcatgctccgtgatgcatgaggctctgcacaacc<br>actacacgcagaagagcctctccctgtctccgggtaaaaaagatcccaaattttgggtgctggtggtg<br>gttggtggagtcctggcttgctatagcttgctagtaacagtggcctttattattttctgggtgaggagtaaga<br>ggagcaggctcctgcacagtgactacatgaacatgactccccgccgcccgggcccacccgcaag<br>cattaccagcctatgccccaccacgcgacttcgcagcctatcgctccctgagagtgaagttcagcag<br>gagcgcagacgcccccgcgtaccagcagggccagaaccagctctataacgagctcaatctaggac<br>gaagagaggagtacgatgtttttggacaagagacgtggccgggaccctgagatgggggaaagcc<br>gagaaggaagaaccctcaggaaggcctgtacaatgaactgcagaaagataagatggcggaggc<br>ctacagtgagattgggatgaaaggcgagcgccggaggggcaaggggcacgatggcctttaccagg<br>gtctcagtacagccaccaaggacacctacgacgcccttcacatgcaggccctgccccctcgctga | Construct X<br>X_MP71-<br>hBCMA-VL-<br>WL-<br>VH_IgG1_CD28_CD3z |
| 88 | atggatttccaggtgcagatcttcagcttcctgctgatctccgccagcgtgatcatgagccgcgaagtgc<br>agctggtcgaatctggaggaggcctggttcagcctggtggcagccttaggctctcttgtgcagcctctgg<br>cttaccttctcacggtattggttcagctgggtgagacaggtccagggaaaggtctggtgtgggtaggg<br>gagataaacccagcagcagcacgatcaactatgctccgtcactgaaagacaagttcacctttccc<br>gcgataatgccaagaacactctctacttgcagatgaattccctcgagccggcagatacagcggttgact<br>actgcgccagtctgtactacgactacggcgatacgactattggggacaagcacactggtgac<br>tgttagctccggcagcaccagcggctccggcaagcctggctctggcgagggcagcacaaagggag<br>agatcgtgatgacccagtctcctgctaccctgagcgtttctcccggtgaaagggccacactcagctgca<br>agcctctcaaagcgtggagagcaatgtcgcctggtatcagcagaaacctggccaagctccgagag<br>cactgatctattccgcgctcatttgcgctttccggcataccagcggttagtggctcagggagtgggact<br>gagttcactctgacgattagctcccttcagtcagaggattcgccgtgtactactgtcagcagtacaaca<br>actatcccctcacattcggagctgaaccaagctggaactgaagcctgccgagcctaagagcccg<br>acaagacccacacctgtccccttgtcctgccctccagtggctggccctagcgtgttcctgttccccc<br>aaagcccaaggataccctgatgatcgcccggaccccgaagtcacatgcgtggtggtggacgtgag<br>ccacgaagacctgaggtcaagttcaactggtacgtggacggcgtggaggtgcataatgccaagac | Construct XI<br>XI_MP71-<br>hBCMA-VH-<br>WL-<br>VL_IgG1_CD28_CD3z_no_opt |

-continued

| | | |
|---|---|---|
| | aaagccgcggggaggagcagtacaacagcacgtaccgtgtggtcagcgtcctcaccgtcctgcacc<br>aggactggctgaatggcaaggagtacaagtgcaaggtctccaacaaagcccTcccagccccatc<br>gagaaaaccatctccaaagccaaagggcagccccgagaaccacaggtgtacaccctgcccccat<br>cccgggatgagctgaccaagaaccaggtcagcctgacctgcctggtcaaaggcttctatcccagcg<br>acatcgccgtggagtgggagagcaatgggcagccggagaacaactacaagaccacgcctcccgt<br>gctggactccgacggctccttcttcctctacagcaagctcaccgtggacaagagcaggtggcagcag<br>gggaacgtcttctcatgctccgtgatgcatgaggctctgcacaaccactacacgcagaagagcctctc<br>cctgtctccgggtaaaaaagatcccaaattttgggtgctggtggtggttggtggagtcctggcttgctata<br>gcttgctagtaacagtggcctttattattttctgggtgaggagtaagaggagcaggctcctgcacagtga<br>ctacatgaacatgactccccgccgcccccgggcccacccgcaagcattaccagccctatgccccacc<br>acgcgacttcgcagcctatcgctccctgagagtgaagttcagcaggagcgcagacgcccccgcgta<br>ccagcagggccagaaccagctctataacgagctcaatctaggacaagagaggagtacgatgttttt<br>ggacaagagacgtggccgggaccctgagatgggggaaagccgagaaggaagaaccctcagg<br>aaggcctgtacaatgaactgcagaaagataagatggcggaggcctacagtgagattgggatgaaa<br>ggcgagcgccggaggggcaaggggcacgatggcctttaccagggtctcagtacagccaccaagg<br>acacctacgacgcccttcacatgcaggccctgccccctcgctga | |
| 89 | atggatttccaggtgcagatcttcagcttcctgctgatctccgccagcgtgatcatgagccgcgaggtgc<br>agctggtggaatctggcggaggactggtgcagcctggcggctctctgagactgtcttgtgccgccagc<br>ggcttcaccttcagccggtactggtttagctgggtgcgccaggcccctggcaagggactcgtgtgggtg<br>ggagagatcaaccccagcagcagcaccatcaactacgcccccagcctgaaggacaagttcaccat<br>cagcagagacaacgccaagaacaccctgtacctgcagatgaacagcctgcgggccgaggacac<br>cgccgtgtactattgtgccagcctgtactacgactacgcgacgcctacgattactggggcagggca<br>cactggtgactgttagctccggcagcaccagcggctccggcaagcctggctctggcgagggcagca<br>aaagggagagatcgtgatgacacagagccctgccaccctgagcgtgtcccaggcgaaagagct<br>accctgagctgcaaggccagccagagcgtggaaagcaacgtggcctggtatcagcagaagcccg<br>gacaggctcctcgggccctgatctacagcgccagcctgagattcagcggcatccccgccaggttttcc<br>ggatctggcagcggcaccgagttcaccctgacaatcagcagcctgcagagcgaggactttgccgtgt<br>attactgccagcagtacaacaactacccctgaccttcggagccggcaccaagctggagctgaagg<br>agagcaagtacggccctccctgccccccttgccctgccccgcctcgagggccgaacccagcgtgtt<br>cctgttcccccccaagccccaaggacacccTgatgatcagccggaccccgaggtgacctgcgtggt<br>ggtggacgtgagccaggaagatcccgaggtccagttcaattggtacgtggacggcgtggaagtgca<br>caacgccaagaccaagccagagaggaacagttcaacagcacctaccgggtggtgtctgtgctga<br>ccgtgctgcaccaggactggctgaacggcaaagaatacaagtgcaaggtgtccaacaaggcctg<br>cccagcagcatcgaaaagaccatcagcaaggccaagggccagccctccgcgagccccaggtgtaca<br>ccctgcctccctcccaggaagagatgaccaagaaccaggtgtccctgacctgcctggtgaagggctt<br>ctaccccagcgacatcgccgtggagtgggagagcaacggccagcctgagaacaactacaagacc<br>accctcccgtgctggacagcgacggcagcttcttcctctacagccggctgaccgtggacaagagcc<br>ggtggcaggaaggcaacgtcttagctgcagcgtgatgcacgaggccctgcacaaccactacccc<br>agaagagcctgagcctgtccctgggcaagttttgggtgctggtggtggttggtggagtcctggcttgctat<br>agcttgctagtaacagtggcctttattattttctgggtgaggagtaagaggagcaggctcctgcacagtg<br>actacatgaacatgactccccgtcgacccgggcccacccgcaagcattaccagccctatgccccac<br>cacgcgacttcgcagcctatcgctccctgagagtgaagttcagcaggagcgcagacgcccccgcgta<br>ccagcagggccagaaccagctctataacgagctcaatctaggacaagagaggagtacgatgtttt<br>tggacaagagacgtggccgggaccctgagatgggggaaagccgagaaggaagaaccctcagg<br>aaggcctgtacaatgaactgcagaaagataagatggcggaggcctacagtgagattgggatgaaa<br>ggcgagcgccggaggggcaaggggcacgatggcctttaccagggtctcagtacagccaccaagg<br>acacctacgacgcccttcacatgcaggccctgccccctcgctga | Construct XII<br>XII_new_cuts_MP71-<br>hBCMA-<br>VH-WL-<br>VL_IgG4_CD28_CD3z |
| 90 | atggatttccaggtgcagatcttcagcttcctgctgatctccgccagcgtgatcatgagccgcgaggtgc<br>agctggtggaatctggcggaggactggtgcagcctggcggctctctgagactgtcttgtgccgccagc<br>ggcttcaccttcagccggtactggtttagctgggtgcgccaggcccctggcaagggactcgtgtgggtg<br>ggagagatcaaccccagcagcagcaccatcaactacgcccccagcctgaaggacaagttcaccat<br>cagcagagacaacgccaagaacaccctgtacctgcagatgaacagcctgcgggccgaggacac<br>cgccgtgtactattgtgccagcctgtactacgactacgcgacgcctacgattactggggcagggca<br>cactggtgactgttagctccggcagcaccagcggctccggcaagcctggctctggcgagggcagca<br>aaagggagagatcgtgatgacacagagccctgccaccctgagcgtgtcccaggcgaaagagct<br>accctgagctgcaaggccagccagagcgtggaaagcaacgtggcctggtatcagcagaagcccg<br>gacaggctcctcgggccctgatctacagcgccagcctgagattcagcggcatccccgccaggttttcc<br>ggatctggcagcggcaccgagttcaccctgacaatcagcagcctgcagagcgaggactttgccgtgt<br>attactgccagcagtacaacaactacccctgaccttcggagccggcaccaagctggagctgaagg<br>agagcaagtacggccctccctgccccccttgccctggccagcctcgcgagccccaggtgtacaccct<br>gcctccctcccaggaagagatgaccaagaaccaggtgtccctgacctgcctggtgaagggcttctac<br>cccagcgacatcgccgtggagtgggagagcaacggccagcctgagaacaactacaagaccacc<br>cctcccgtgctggacagcgacggcagcttcttcctctacagccggctgaccgtggacaagagccggt<br>ggcaggaaggcaacgtcttTagctgcagcgtgatgcacgaggccctgcacaaccactacacccag<br>aagagcctgagcctgtccctgggcaagttttgggtgctggtggtggttggtggagtcctggcttgctatag<br>cttgctagtaacagtggcctttattattttctgggtgaggagtaagaggagcaggctcctgcacagtgact<br>acatgaacatgactccccgccgcccccgggcccacccgcaagcattaccagccctatgccccaccac<br>gcgacttcgcagcctatcgctccctgagagtgaagttcagcaggagcgcagacgcccccgcgtacc<br>agcagggccagaaccagctctataacgagctcaatctaggacaagagaggagtacgatgttttgg<br>acaagagacgtggccgggaccctgagatgggggaaagccgagaaggaagaaccctcaggaa<br>ggcctgtacaatgaactgcagaaagataagatggcggaggcctacagtgagattgggatgaaag<br>gcgagcgccggaggggcaaggggcacgatggcctttaccagggtctcagtacagccaccaaggac<br>acctacgacgcccttcacatgcaggccctgccccctcgctga | Construct XIII<br>XIII_new_cuts_MP71-<br>hBCMA-VH-<br>WL-<br>VL_IgG4_HI_CH3_CD28_CD3z |
| 91 | atggatttccaggtgcagatcttcagcttcctgctgatctccgccagcgtgatcatgagccgcgaggtgc<br>agctggtggaatctggcggaggactggtgcagcctggcggctctctgagactgtcttgtgccgccagc<br>ggcttcaccttcagccggtactggtttagctgggtgcgccaggcccctggcaagggactcgtgtgggtg | Construct XIV<br>XIV_new_cuts_MP71-<br>hBCMA-VH- |

-continued

| | | |
|---|---|---|
| | ggagagatcaacccccagcagcagcaccatcaactacgcccccagcctgaaggacaagttcaccat<br>cagcagagacaacgccaagaacaccctgtacctgcagatgaacagcctgcgggccgaggacac<br>cgccgtgtactattgtgccagcctgtactacgactacggcgacgcctacgattactggggccagggca<br>cactggtgactgttagctccggcagcaccagcggctccggcaagcctggctctggcgagggcagca<br>caaaggagagatcgtgatgacacagagccctgccaccctgagcgtgtcccaggcgaaagagct<br>accctgagctgcaaggccagccagagcgtggaaagcaacgtggcctggtatcagcagaagcccg<br>gacaggctcctcgggccctgatctacagcgccagcctgagattcagcggcatccccgccaggttttcc<br>ggatctggcagcggcaccgagttcaccctgacaatcagcagcctgcagagcgaggactttgccgtgt<br>attactgccagcagtacaacaactacccctgaccttcggagccggcaccaagctggagctgaagg<br>agagcaagtacggcccccctgccccccttgcccttttgggtgctggtggtggttggtggagtcctggct<br>tgctatagcttgctagtaacagtggcctttattattttctgggtgaggagtaagaggagcaggctcctgca<br>cagtgactacatgaacatgactccccgtcgacccgggcccacccgcaagcattaccagccctatgcc<br>ccaccacgcgacttcgcagcctatcgctccctgagagtgaagttcagcaggagcgcagacgccccc<br>gcgtaccagcagggccagaaccagctctataacgagctcaatctacgacgaagaggagtacg<br>atgttttggacaagagacgtggccgggaccctgagatggggggaaagccgagaaggaagaaccc<br>tcaggaaggcctgtacaatgaactgcagaaagataagatggcggaggcctacagtgagattgggat<br>gaaaggcgagcgccggaggggcaaggggcacgatggcctttaccagggtctcagtacagccacc<br>aaggacacctacgacgcccttcacatgcaggcctgcccctcgctga | WL-<br>VL_IgG4_HI_CD28_CD3z |
| 92 | atggatttccaggtgcagatcttcagcttcctgctgatctccgccagcgtgatcatgagccgcgaggtgc<br>agctggtggaatctggcggaggactggtgcagcctggcggctctctgagactgtcttgtgccgccagc<br>ggcttcaccttcagcggtactggtttagctgggtgcgccaggcccctggcaagggactcgtgtgggtg<br>ggagagatcaacccccagcagcagcaccatcaactacgcccccagcctgaaggacaagttccatt<br>cagcagagacaacgccaagaacaccctgtacctgcagatgaacagcctgcgggccgaggacac<br>cgccgtgtactattgtgccagcctgtactacgactacggcgacgcctacgattactggggccagggca<br>cactggtgactgttagctccggcagcaccagcggctccggcaagcctggctctggcgagggcagca<br>caaaggagagatcgtgatgacacagagccctgccaccctgagcgtgtcccaggcgaaagagct<br>accctgagctgcaaggccagccagagcgtggaaagcaacgtggcctggtatcagcagaagcccg<br>gacaggctcctcgggccctgatctacagcgccagcctgagattcagcggcatccccgccaggtttag<br>cggctctggcagcggcaccgagttcaccctgacaatcagcagcctgcagagcgaggactttgccgt<br>gtattactgccagcagtacaacaactacccctgaccttcggagccggcaccaagctggagctgaa<br>gcctgccgagcctaagagccccgacaagacccacacctgtccccttgtcctgcccctccagtggct<br>ggccctagcgtgttcctgttccccccaaagcccaaggataccctgatgatcgcccggacccccgaag<br>tcacatgcgtggtggtggacgtgagccacgaagacccctgaggtcaagttcaactggtacgtggacgg<br>cgtggaggtgcataatgccaagacaaagccgcgggaggagcagtacaacagcacgtaccgtgtg<br>gtcagcgtcctcaccgtcctgcaccaggactggctgaatggcaaggagtacaagtgcaaggtctcca<br>acaaagcctcccagccccatcgagaaaaccatctccaaagccaaagggcagccccgagaac<br>cacaggtgtacaccctgcccccatcccgggatgagctgaccaagaaccaggtgtcctgacctgcct<br>cgtgaagggcttctaccccctccgatatcgccgtgaatgggagagcaatggccagcccgagaacaa<br>ctacaagaccaccccccctgtgctggacagcgacggctcattcttcctgtacagcaagctgacagtgg<br>acaagagccggtggcagcagggcaacgtgttcagctgcagcgtgatgcacgaggctctgcacaac<br>cactacacccagaagtcccctgagcagcctgagcccaggcaagaagatctacatctggggccctctg<br>gccggcactgtggcgtgctgctgctgtctccgtgatcacactgtactgcaagcggggcagaaagaa<br>gctgctgtacatcttcaagcagccctttcatgcggcccgtgcagaccaccaggaagaggacggctgc<br>tcctgcagattcccgaggaagaagaaggcggctgcgagctgctgcgcgtgaagtttctagaagcg<br>ccgacgcccctgcctaccagcagggccagaaccagctgtacaacgagctgaacctgggcagacg<br>ggaagagtacgacgtgctggataagcggagaggccgggaccctgagatggggcggcaagcctaga<br>agaaagaaccccaggaaggcctgtataacgaactgcagaaagacaagatggccgaggcctac<br>agcgagatcggaatgaagggcgagcggagaagaggcaagggccacgatggactgtaccaggg<br>cctgagcaccgccaccaaggacacctatgacgccctgcacatgcaggctctgcccccaga | Construct XV<br>XV_MP71-<br>hBCMA-VH-<br>WL-<br>VL_IgGdelta_CD8_4-<br>1BB_CD3z |
| 93 | atggatttccaggtgcagatcttcagcttcctgctgatctccgccagcgtgatcatgagccgcgagatcg<br>tgatgacacagagccctgccaccctgagcgtgtcccaggcgaaagagctaccctgagctgcaag<br>gccagccagagcgtggaaagcaacgtggcctggtatcagcagaagcccgacaggctcctcggg<br>ccctgatctacagcgccagcctgagattcagcggcatccccgccaggtttagcggctctggcagcgg<br>caccgagttcaccctgacaatcagcagcctgcagagcgaggactttgccgtgtattactgccagcagt<br>acaacaactacccctgaccttcggagccggcaccaagctggagctgaagggcagcaccagcgg<br>ctccggcaagcctggctctggcgagggcagcacaaaggagaggtgcagctggtggaatctggcg<br>gaggactggtgcagcctggcggctctctgagactgtcttgtgccgccagcggcttcaccttcagccgt<br>actggtttagctgggtgcgccaggcccctggcaagggactcgtgtgggtgggagagatcaaccca<br>gcagcagcaccatcaactacgcccccagcctgaaggacaagttcaccatcagcagagacaacgc<br>caagaacaccctgtacctgcagatgaacagcctgcgggccgaggacaccgccgtgtactattgtgc<br>cagcctgtactacgactacggcgacgcctacgattactggggccagggcacactggtgactgttagct<br>ccctgccgagcctaagagccccgacaagacccacacctgtccccttgtcctgcccctccagtggct<br>ggccctagcgtgttcctgttccccccaaagcccaaggataccctgatgatcgcccggacccccgaag<br>tcacatgcgtggtggtggacgtgagccacgaagacccctgaggtcaagttcaactggtacgtggacgg<br>cgtggaggtgcataatgccaagacaaagccgcgggaggagcagtacaacagcacgtaccgtgtg<br>gtcagcgtcctcaccgtcctgcaccaggactggctgaatggcaaggagtacaagtgcaaggtctcca<br>acaaagcctcccagccccatcgagaaaaccatctccaaagccaaagggcagccccgagaac<br>cacaggtgtacaccctgcccccatcccgggatgagctgaccaagaaccaggtgtcctgacctgcct<br>cgtgaagggcttctaccccctccgatatcgccgtgaatgggagagcaatggccagcccgagaacaa<br>ctacaagaccaccccccctgtgctggacagcgacggctcattcttcctgtacagcaagctgacagtgg<br>acaagagccggtggcagcagggcaacgtgttcagctgcagcgtgatgcacgaggctctgcacaac<br>cactacacccagaagtcccctgagcagcctgagcccaggcaagaagatctacatctggggccctctg<br>gccggcacctgtggcgtgctgctgctgtctccgtgatcacactgtactgcaagcggggcagaaagaa<br>gctgctgtacatcttcaagcagccctttcatgcggcccgtgcagaccaccaggaagaggacggctgc<br>tcctgcagattcccgaggaagaagaaggcggctgcgagctgctgcgcgtgaagtttctagaagcg<br>ccgacgcccctgcctaccagcagggccagaaccagctgtacaacgagctgaacctgggcagacg<br>ggaagagtacgacgtgctggataagcggagaggccgggaccctgagatgggcggcaagcctaga | Construct XVI<br>XVI_MP71-<br>hBCMA-VL-<br>WL-<br>VH_IgGdelta_CD8_4-<br>1BB_CD3z |

-continued

| | | |
|---|---|---|
| | agaaagaaccccaggaaggcctgtataacgaactgcagaaagacaagatggccgaggcctac<br>agcgagatcggaatgaagggcgagcggagaagaggcaagggccacgatggactgtaccaggg<br>cctgagcaccgccaccaaggacacctatgacgccctgcacatgcaggctctgccccccaga | |
| 94 | atggatttccaggtgcagatcttcagcttcctgctgatctccgccagcgtgatcatgagccgcgaagtgc<br>agctggtcgaatctggaggaggcctggttcagcctggtggcagccttaggctctcttgtgcagcctctgg<br>ctttaccttctcacggtattggttcagctgggtgagacaggctccagggaaaggtctggtgtgggtaggg<br>gagataaacccccagcagcagcacgatcaactatgctccgtcactgaaagacaagttcaccatttcc<br>gcgataatgccaagaacactctctacttgcagatgaatttcccttcgagccgaggatacagccggtgtact<br>actgcgccagtctgtactacgactatggggacgcatacgactattggggacaaggcacactggtgac<br>tgttagctccggcagcaccagcggctccggcaagcctggctctggcgagggcagcacaaagggag<br>agatcgtgatgacccagtctcctgctaccctgagcgtttctcccggtgaaagggccacactcagctgca<br>aagcctctcaaagcgtggagagcaatgtcgcctggtatcagcagaaacctggccaagctccgagag<br>cactgatctattccgcgtcattgcgcttttccggcataccagcacggtttagtggctcagggagtgggact<br>gagttcactctgacgattagctcccttcagtcagaggatttcgccgtgtactactgtcagcagtacaaca<br>actatcccctcacattcggagctggaaccaagctggaactgaagcctgccgagcctaagagcccg<br>acaagacccacacctgtccccttgtcctgccctccagtggctggcctagcgtgttcctgttcccccc<br>aaagcccaaggataccctgatgatcgcccggaccccgaagtcacatgcgtggtggtggacgtgag<br>ccacgaagaccctgaggtcaagttcaactggtacgtggacggcgtggaggtgcataatgccaagac<br>aaagccgcgggaggagcagtacaacagcacgtaccgtgtggtcagcgtcctcaccgtcctgcacc<br>aggactggctgaatggcaaggagtacaagtgcaaggtctccaacaaagcccctcccagcccccatc<br>gagaaaaccatctccaaagccaaagggcagccccgagaaccacaggtgtacaccctgcccccat<br>cccgggatgagctgaccaagaaccaggtgtccctgacctgcctcgtgaagggcttctaccctccgat<br>atcgccgtggaatgggagagcaatggccagcccgagaacaactacaagaccacccccctgtgct<br>ggacagcgacggctcattcttcctgtacagcaagctgacagtggacaagagccggtggcagcagg<br>gcaacgtgttcagctgcagcgtgatgcacgaggctctgcacaaccactacacccagaagtccctga<br>gcagcctgagcccaggcaagaagatctacatctgggcccctctggccggcacctgtggcgtgctgct<br>gctgtctctcgtgatcacactgtactgcaagcggggcagaaagaagctgctgtacatcttcaagcagc<br>ccttcatgcggcccgtgcagaccacccaggaagaggacggctgctcctgcagattccccgaggaag<br>aagaaggcggctgcgagctgctgcgcgtgaagttttctagaaggccgacgcccctgcctaccagc<br>agggccagaaccagctgtacaacgagctgaacctgggcagacgggaagagtacgacgtgctgga<br>taagcggagaggccgggaccctgagatgggcggcaagcctagaagaaagaaccccaggaag<br>gcctgtataacgaactgcagaaagacaagatggccgaggcctacagcgagatcggaatgaaggg<br>cgagcggagaagaggcaagggccacgatggactgtaccagggcctgagcaccgccaccaagga<br>cacctatgacgccctgcacatgcaggctctgccccccaga | Construct XVII<br>XVII_MP71-<br>hBCMA-VH-<br>WL-<br>VL_IgGdelta_CD8_4-<br>1BB_CD3z_no_opt |

A further aspect of the invention relates to a vector comprising a nucleic acid molecule as described herein, preferably a viral vector, more preferably a gamma retroviral vector. A further aspect of the invention relates to a genetically modified immune cell comprising a nucleic acid molecule or vector as described herein, and/or expressing a CAR as described herein, wherein the immune cell is preferably selected from the group consisting of a T lymphocyte or an NK cell, more preferably cytotoxic T lymphocytes.

In a preferred embodiment the genetically modified immune cell comprising a nucleic acid molecule or vector as described herein, and/or expressing a CAR as described herein, is characterised in that it is CD4+ and/or CD8+ T cell, preferably a mixture of CD4+ and CD8+ T cells. These T cell populations, and preferably the composition comprising both CD4+ and CD8+ transformed cells, show particularly effective cytolytic activity against various malignant B cells, such as multiple myeloma and B-NHL, preferably against those cells and/or the associated medical conditions described herein.

A further aspect of the invention relates to an immune cell as described herein comprising a nucleic acid molecule or vector as described herein, and/or expressing a CAR as described herein, for use as a medicament in the treatment of a medical disorder associated with the presence of pathogenic B cells, such as a disease of plasma cells, memory B cells and/or mature B cells, in particular multiple myeloma or non-Hodgkin's lymphoma.

In one embodiment the medical use of the immune cell is characterised in that the medical disorder to be treated is multiple myeloma.

In one embodiment the medical use of the immune cell is characterised in that the medical disorder to be treated is non-Hodgkin's lymphoma.

In one embodiment the medical use of the immune cell is characterised in that the medical condition to be treated is associated with pathogenic mature B cells. To the knowledge of the inventors, no previous disclosure is apparent in the art that teaches that such mature B cells can be effectively targeted by a BCMA CAR-T, as described herein. Some of the tested tumor cell lines demonstrated in the examples below relate to mature B cells and are not necessarily of the memory type. In comparison, immature B cells would be those that give rise to acute lymphatic leukemia. The invention therefore also encompasses a method of treatment for the medical disorders disclosed herein, comprising the administration of a therapeutically effective amount of a CAR or a therapeutic agent comprising the CAR of the present invention to a subject in need of such treatment.

A further aspect of the invention relates to a pharmaceutical composition comprising the CAR or therapeutic agent comprising a CAR as described herein together with a pharmaceutically acceptable carrier.

DETAILED DESCRIPTION

Multiple myeloma, also referred to as plasmacytoma, is a currently incurable B cell lymphoma which is derived from a malignantly transformed plasma cell clone. This disease constitutes the most frequent tumor of bone and bone marrow, has a median life-expectancy of seven years and is responsible for 2% of annual deaths from cancer. The malignant transformation is believed to occur in germinal centers of secondary lymphoid organs at a developmental stage where B cells have completed VDJ-rearrangement and isotype switching. The median age at diagnosis is 70 years, indicating that in many patients co-morbidities exist that preclude intensive and prolonged chemo-or radiotherapies. Moreover, allogeneic bone marrow transplantations are usually excluded for this patient cohort. The disease is characterized clinically by osteolytic lesions, hypercalcemia, hematopoietic insufficiency, amyloid deposition, renal failure, exceessive antibody heavy and/or light chain production, hyperviscosity, infections, bleeding disorders. The standard of care is chemotherapy, either alone or in combination with autologous stem cell transplantation, immunomodulators such as immunomodulatory drugs (IMIDs), local irradiation, proteasome inhibitors, and for a few patients allogeneic stem cell transplantation applies. Despite intensive treatments with the aformentioned modalities, the disease usually relapses and after multiple lines of therapies primary and secondary resistances develop.

The adoptive chimeric antigen receptor (CAR)-T cell therapies described herein targeted at the B cell maturation antigen (BCMA) can overcome these limitations in multiple myeloma because BCMA is highly expressed in multiple myeloma tumor cells, but not in normal B cells or precursor B cells. Secondly, in anti-CD19 antibody or anti-CD19 CAR-T cell therapies directed against B cell non-Hodgkin's lymphoma (B-NHL) resistances occur due to antigen loss. Because treatment resistance occurs after multiple lines of chemo-/immunotherapy in these B-NHLs, alternative target structures are warranted. For mature B-NHL, BCMA is a suitable target and therefore, the anti-BCMA CAR-T cells with a high affinity can be employed therapeutically even in B-NHL as specified below.

BCMA CAR-T cell transfers are selective for the tumor-associated antigen BCMA, applicable and effective even for the elderly and after multidrug resistances have appeared. They have predictable, tolerable and manageable side effects. Autologous T cells equipped with the anti-BCMA CAR have a high affinity and avidity and recognize and destroy multiple myeloma cells while sparing normal hematopoietic cells such as T cells, B cells and their bone marrow precursors; all myeloid cells and NK cells are likewise spared. Due to autologous transfer of T cells a graft-versus-host-disease cannot occur. Memory T cell formation which is important for the prevention of a relapse can develop. Due to the high affinity and avidity of the anti-BCMA CAR-T cell, even low BCMA-expressing mature B cell NHL can be recognized, allowing for T cell activation and tumor cell killing. Such mature B-NHL entities include certain stages of follicular lymphoma, diffuse large B-cell lymphoma, mantle cell lymphoma, and chronic lymphocytic leukemia.

The anti-BCMA CAR-T cell described herein is in some embodiments applicable to multiple myeloma and B-NHL patients who are not eligible for other therapies. More specifically: i) patients with multidrug resistancies, ii) patients not eligible for allogeneic stem cell transplantation, iii) patients with co-morbidities that preclude further chemotherapies, iv) aged patients who do not tolerate chemotherapies, v) the CAR is applicable for salvage therapies even after progressive disease and multiple lines of other standard of care therapies have failed, vi) it is applicable even at very low antigen density on target tumor cells, where antibodies can fail, vii) a structure of the source antibody complexed with BCMA at near atomic resolution verifies its exquisite specificity, a biosafety feature not shown for other anti-BCMA CAR-T cells, and/or vii) it is applicable as a monotherapy which is not the case for antibodies.

For other anti-BCMA CAR-T cells described in the art their reactivity has only been shown for multiple myeloma cells and patients; in contrast, our anti-BCMA CAR has an unexpectedly high sensitivity even for low BCMA expressing B-NHL cell lines. Our anti-BCMA CAR confers extremely high avidity to T cells, necessary for anti-tumor efficacy. No other anti-BCMA CAR is reported to react against mature B-NHL, diffuse large B-cell lymphoma (DLBCL), defined stages of follicular lymphoma, mantle cell lymphoma, or chronic lymphocytic leukemia. The present invention demonstrates that our anti-BCMA CAR does not confer T cell-reactivity against physiological B cells, T cells, NK cells, endothelial cells, all myeloid cell lineages and their precursors. Thus, the present invention has an unprecedented low off-target reactivity on other hematopoietic tissues. In contrast to anti-CD38 CAR-T cells, our anti-BCMA CAR has no unwanted reactivity against myeloid cell precursors.

The amino acid sequence of the scFV fragment as described previously in WO/2015/166073 and in WO/2014/068079 has been modified i) in order to allow folding and expression in context of a transmembrane receptor structure; ii) the order of the light and heavy chain fragments has been inverted, iii) the linker sequence between heavy and light chains has been lengthened. Modifications enable sufficient surface expression on T cells and still maintain proper antigen binding.

Due to the low nanomolar affinity of the original FSY IgG, which is the antibody template for the scFv-part of the CAR-T cell construct, the invention is characterised in preferred embodiments in that the anti-BCMA CAR has an unexpectedly high affinity and confers extremely high specificity and avidity to T cells. High affinity and high avidity enable CAR-T cells to i) recognize, ii) be activated against, and iii) kill tumor target cells with high, intermediate and low BCMA surface expression. None of the aforementioned anti-BCMA CARs of the prior art have proven reactivity against B-NHL other than multiple myeloma cells. Therefore, the anti-BCMA CAR of the present invention is a specific and highly active reagent against an unprecedented diversity of B-NHLs with low levels/numbers of BCMA molecules. In combination with a retroviral vector, preferably the MP71-vector and a gamma-retrovirus expression system, an unusually high transduction rate for human T cells can be achieved.

Another distinct advantage of the present invention is the detailed knowledge of the BCMA epitope recognized by the scFv fragment of the CAR. So far, no other antibody-based invention or publication has identified a BCMA epitope. Thus, the anti-BCMA CAR as described herein exhibits a substantially higher biosafety profile and no known off-target reactivity in vivo and in vitro.

Additionally, the inventors have exchanged signaling components of our CAR construct in an easy three step cloning that allows for a modular composition of clinically applicable anti-BCMA CARs.

In an in vitro co-culture system, anti-BCMA CAR-T cells of the invention become activated upon exposure to BCMA-expressing human B-NHL and multiple myeloma tumor cell lines. These T cells then develop an effector phenotype with high level secretion of IFN-gamma, a phenotype that is predictive of a cytotoxic activity.

Pre-clinical assessment involves i) in vitro cytotoxicity testing against suitable B-NHL cell lines and primary myeloma cells from patients, ii) in vivo testing of anti-BCMA CAR activity against xenotransplanted B-NHLs and multiple myeloma cell lines.

In the human setting in vivo, myeloma patients with the following characteristics are assessed via clinical phase I study: i) patients with multidrug resistancies, ii) patients not eligible for allogeneic stem cell transplantation, iii) patients with co-morbidities that preclude further chemotherapies, iv) aged patients who do not tolerate chemotherapies, v) patients for salvage therapies after progressive disease has appeared, vi) patients where multiple lines of other standard of care therapies have failed, vii) patients with progressive disease after autologous stem cell transplantation, viii) patients with progressive disease after allogeneic stem cell transplantation, ix) as a bridging therapy before allogeneic stem cell transplantation. Moreover, in the human setting, B-NHL patients with diffuse large B-cell lymphoma, follicular lymphoma, chronic lymphocytic leukemia, and mantle cell lymphoma with the following characteristics are assessed in a clinical phase I study: i) patients with multidrug resistancies, ii) patients not eligible for allogeneic stem cell transplantation, iii) patients with co-morbidities that preclude further chemotherapies, iv) aged patients who do not tolerate chemotherapies, v) patients for salvage therapies after progressive disease has appeared and multiple lines of other standard of care therapies have failed, vi) patients with progressive disease after autologous stem cell transplantation, vii) patients with progressive disease after allogeneic stem cell transplantation, viii) as a bridging therapy before allogeneic stem cell transplantation, ix) patients exhibiting escape variants or mutants of CD19 and/or CD20 on tumor cells, such that current antibody therapies (anti CD20, Rituximab, anti CD19, elotuzumab, BITE CD19/CD3, Blinatumomab) or anti-CD19 CAR therapies have lost/down-regulated their target structures and become ineffective.

An additional and surprising aspect of the invention is an improved stability of the CAR as disclosed herein. The CAR polypeptide can readily be stored for extended periods under appropriate conditions without any loss of binding affinity.
Chimeric Antigen Receptors:

CARs are composed of an extracellular ectodomain derived from an antibody and an endodomain comprising signaling modules derived from T cell signaling proteins. In a preferred embodiment, the ectodomain preferably comprises variable regions from the heavy and light chains of an immunoglobulin configured as a single-chain variable fragment (scFv). The scFv is preferably attached to a hinge region that provides flexibility and transduces signals through an anchoring transmembrane moiety to an intracellular signaling domain. The transmembrane domains originate preferably from either CD8α or CD28. In the first generation of CARs the signaling domain consists of the zeta chain of the TCR complex. The term "generation" refers to the structure of the intracellular signaling domains. Second generation CARs are equipped with a single costimulatory domain originated from CD28 or 4-1BB. Third generation CARs already include two costimulatory domains, e.g. CD28, 4-1BB, ICOS or OX40, CD3 zeta. The present invention preferably relates to a second or third generation CAR.

In various embodiments, genetically engineered receptors that redirect cytotoxicity of immune effector cells toward B cells are provided. These genetically engineered receptors referred to herein as chimeric antigen receptors (CARs). CARs are molecules that combine antibody-based specificity for a desired antigen (e.g., BCMA) with a T cell receptor-activating intracellular domain to generate a chimeric protein that exhibits a specific anti-BCMA cellular immune activity. As used herein, the term, "chimeric," describes being composed of parts of different proteins or DNAs from different origins.

CARs contemplated herein, comprise an extracellular domain (also referred to as a binding domain or antigen-binding domain) that binds to BCMA, a transmembrane domain, and an intracellular domain, or intracellular signaling domain. Engagement of the anti-BCMA antigen binding domain of the CAR with BCMA on the surface of a target cell results in clustering of the CAR and delivers an activation stimulus to the CAR-containing cell. The main characteristic of CARs are their ability to redirect immune effector cell specificity, thereby triggering proliferation, cytokine production, phagocytosis or production of molecules that can mediate cell death of the target antigen expressing cell in a major histocompatibility (MHC) independent manner, exploiting the cell specific targeting abilities of monoclonal antibodies, soluble ligands or cell specific co-receptors.

In various embodiments, a CAR comprises an extracellular binding domain that comprises a humanized BCMA-specific binding domain; a transmembrane domain; one or more intracellular signaling domains. In particular embodiments, a CAR comprises an extracellular binding domain that comprises a humanized anti-BCMA antigen binding fragment thereof; one or more spacer domains; a transmembrane domain; one or more intracellular signaling domains.

The "extracellular antigen-binding domain" or "extracellular binding domain" are used interchangeably and provide a CAR with the ability to specifically bind to the target antigen of interest, BCMA. The binding domain may be derived either from a natural, synthetic, semi-synthetic, or recombinant source. Preferred are scFV domains.

"Specific binding" is to be understood as via one skilled in the art, whereby the skilled person is clearly aware of various experimental procedures that can be used to test binding and binding specificity. Methods for determining equilibrium association or equilibrium dissociation constants are known in the art. Some cross-reaction or background binding may be inevitable in many protein-protein interactions; this is not to detract from the "specificity" of the binding between CAR and epitope. "Specific binding" describes binding of an anti-BCMA antibody or antigen binding fragment thereof (or a CAR comprising the same) to BCMA at greater binding affinity than background binding. The term "directed against" is also applicable when considering the term "specificity" in understanding the interaction between antibody and epitope.

An "antigen (Ag)" refers to a compound, composition, or substance that can stimulate the production of antibodies or a T cell response in an animal. In particular embodiments, the target antigen is an epitope of a BCMA polypeptide. An "epitope" refers to the region of an antigen to which a binding agent binds. Epitopes can be formed both from contiguous amino acids or noncontiguous amino acids juxtaposed by tertiary folding of a protein. "Single-chain Fv" or "scFv" antibody fragments comprise the VH and VL domains of antibody, wherein these domains are present in a single polypeptide chain and in either orientation {e.g., VL-VH or VH-VL). Generally, the scFv polypeptide further comprises a polypeptide linker between the VH and VL domains which enables the scFv to form the desired structure for antigen binding. In preferred embodiments, a CAR contemplated herein comprises antigen-specific binding domain that is an scFv and may be a murine, human or humanized scFv. Single chain antibodies may be cloned form the V region genes of a hybridoma specific for a desired target. In particular embodiments, the antigen-specific binding domain that is a humanized scFv that binds a human BCMA polypeptide. An illustrative example of a variable heavy chain that is suitable for constructing anti-BCMA CARs contemplated herein include, but are not limited to the amino acid sequence set forth in SEQ ID NO:

11. An illustrative example of a variable light chain that is suitable for constructing anti-BCMA CARs contemplated herein include, but is not limited to, the amino acid sequence set forth in SEQ ID NO: 12.

Antibodies and Antibody Fragments:

The CAR comprises an extracellular antigen-binding domain, comprising an antibody or antibody fragment that binds a B Cell Maturation Antigen (BCMA) polypeptide. Antibodies or antibody fragments of the invention therefore include, but are not limited to polyclonal, monoclonal, bispecific, human, humanized or chimeric antibodies, single chain fragments (scFv), single variable fragments (ssFv), single domain antibodies (such as VHH fragments from nanobodies), Fab fragments, F(ab')$_2$ fragments, fragments produced by a Fab expression library, anti-idiotypic antibodies and epitope-binding fragments or combinations thereof of any of the above, provided that they retain similar binding properties of the CAR described herein, preferably comprising the corresponding CDRs, or VH and VL regions as described herein. Also mini-antibodies and multivalent antibodies such as diabodies, triabodies, tetravalent antibodies and peptabodies can be used in a method of the invention. The immunoglobulin molecules of the invention can be of any class (i.e. IgG, IgE, IgM, IgD and IgA) or subclass of immunoglobulin molecules. Thus, the term antibody, as used herein, also includes antibodies and antibody fragments comprised by the CAR of the invention, either produced by the modification of whole antibodies or synthesized de novo using recombinant DNA methodologies.

As used herein, an "antibody" generally refers to a protein consisting of one or more polypeptides substantially encoded by immunoglobulin genes or fragments of immunoglobulin genes. Where the term "antibody" is used, the term "antibody fragment" may also be considered to be referred to. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. The basic immunoglobulin (antibody) structural unit is known to comprise a tetramer or dimer. Each tetramer is composed of two identical pairs of polypeptide chains, each pair having one "light" (L) (about 25 kD) and one "heavy" (H) chain (about 50-70 kD). The N-terminus of each chain defines a variable region of about 100 to 110 or more amino acids, primarily responsible for antigen recognition. The terms "variable light chain" and "variable heavy chain" refer to these variable regions of the light and heavy chains respectively. Optionally, the antibody or the immunological portion of the antibody, can be chemically conjugated to, or expressed as, a fusion protein with other proteins.

The CARs of the invention are intended to bind against mammalian, in particular human, protein targets. The use of protein names may correspond to either mouse or human versions of a protein.

Affinities of binding domain polypeptides and CAR proteins according to the present disclosure can be readily determined using conventional techniques, e.g., by competitive ELISA (enzyme-linked immunosorbent assay), or by binding association, or displacement assays using labeled ligands, or using a surface-plasmon resonance device such as the Biacore. Humanized antibodies comprising one or more CDRs of antibodies of the invention or one or more CDRs derived from said antibodies can be made using any methods known in the art. For example, four general steps may be used to humanize a monoclonal antibody. These are: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody. See, for example, U.S. Pat. Nos. 4,816,567; 5,807,715; 5,866,692; 6,331,415; 5,530,101; 5,693,761; 5,693,762; 5,585,089; 6,180,370; 5,225,539; 6,548,640.

The term humanized antibody means that at least a portion of the framework regions, and optionally a portion of CDR regions or other regions involved in binding, of an immunoglobulin is derived from or adjusted to human immunoglobulin sequences. The humanized, chimeric or partially humanized versions of the mouse monoclonal antibodies can, for example, be made by means of recombinant DNA technology, departing from the mouse and/or human genomic DNA sequences coding for H and L chains or from cDNA clones coding for H and L chains. Humanized forms of mouse antibodies can be generated by linking the CDR regions of non-human antibodies to human constant regions by recombinant DNA techniques (Queen et al., 1989; WO 90/07861). Alternatively the monoclonal antibodies used in the method of the invention may be human monoclonal antibodies. Human antibodies can be obtained, for example, using phage-display methods (WO 91/17271; WO 92/01047).

As used herein, humanized antibodies refer also to forms of non-human (e.g. murine, camel, llama, shark) antibodies that are specific chimeric immunoglobulins, immunoglobulin chains, or fragments thereof (such as Fv, Fab, Fab', F(ab')$_2$ or other antigen-binding subsequences of antibodies) that contain minimal sequence derived from non-human immunoglobulin.

As used herein, human or humanized antibody or antibody fragment means an antibody having an amino acid sequence corresponding to that of an antibody produced by a human and/or has been made using any of the techniques for making human antibodies known in the art or disclosed herein. Human antibodies or fragments thereof can be selected by competitive binding experiments, or otherwise, to have the same epitope specificity as a particular mouse antibody. The humanized antibodies of the present invention surprisingly share the useful functional properties of the mouse antibodies to a large extent. Human polyclonal antibodies can also be provided in the form of serum from humans immunized with an immunogenic agent. Optionally, such polyclonal antibodies can be concentrated by affinity purification using amyloid fibrillar and/or non-fibrillar polypeptides or fragments thereof as an affinity reagent. Monoclonal antibodies can be obtained from serum according to the technique described in WO 99/60846.

Variable Regions and CDRs

A variable region of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are a number of techniques available for determining CDRs, such as an approach based on cross-species sequence variability (i.e., Kabat et al. Sequences of Proteins of Immunological Interest, (5th ed., 1991, National Institutes of Health, Bethesda Md.)); and an approach based on crystallographic studies of antigen-antibody complexes (Al-lazikani et al. (1997) J. Molec. Biol. 273:927-948). Alternative approaches include the IMGT international ImMunoGene Tics information system, (Marie-Paule Lefranc). The Kabat definition is based on sequence variability and is the most commonly used method. The Chothia definition is based on the location of the structural loop regions, wherein the AbM definition is a compromise between the two used by Oxford Molecular's AbM antibody modelling software (refer www.bioinf.org.uk: Dr. Andrew C. R. Martin's Group). As used herein, a CDR may refer to CDRs defined by one or more approach, or by a combination of these approaches.

In some embodiments, the invention provides an antibody or fragment thereof incorporated into a CAR, wherein said antibody or fragment thereof comprises at least one CDR, at least two, at least three, or more CDRs that are substantially identical to at least one CDR, at least two, at least three, or more CDRs of the antibody of the invention. Other embodiments include antibodies which have at least two, three, four, five, or six CDR(s) that are substantially identical to at least two, three, four, five or six CDRs of the antibodies of the invention or derived from the antibodies of the invention. In some embodiments, the at least one, two, three, four, five, or six CDR(s) are at least about 70%, 75%, 85%, 86%, 87%, 88%, 89%, 90%, 95%, 96%, 97%, 98%, or 99% identical to at least one, two or three CDRs of the antibody of the invention. It is understood that, for purposes of this invention, binding specificity and/or overall activity is generally retained, although the extent of activity may vary compared to said antibody (may be greater or lesser).

Additional Components of the CAR

In certain embodiments, the CARs contemplated herein may comprise linker residues between the various domains, added for appropriate spacing and conformation of the molecule, for example a linker comprising an amino acid sequence that connects the VH and VL domains and provides a spacer function compatible with interaction of the two sub-binding domains so that the resulting polypeptide retains a specific binding affinity to the same target molecule as an antibody that comprises the same light and heavy chain variable regions. CARs contemplated herein, may comprise one, two, three, four, or five or more linkers. In particular embodiments, the length of a linker is about 1 to about 25 amino acids, about 5 to about 20 amino acids, or about 10 to about 20 amino acids, or any intervening length of amino acids.

Illustrative examples of linkers include glycine polymers; glycine-serine polymers; glycine-alanine polymers; alanine-serine polymers; and other flexible linkers known in the art, such as the Whitlow linker. Glycine and glycine-serine polymers are relatively unstructured, and therefore may be able to serve as a neutral tether between domains of fusion proteins such as the CARs described herein.

In particular embodiments, the binding domain of the CAR is followed by one or more "spacers" or "spacer polypeptides," which refers to the region that moves the antigen binding domain away from the effector cell surface to enable proper cell/cell contact, antigen binding and activation. In certain embodiments, a spacer domain is a portion of an immunoglobulin, including, but not limited to, one or more heavy chain constant regions, e.g., CH2 and CH3. The spacer domain can include the amino acid sequence of a naturally occurring immunoglobulin hinge region or an altered immunoglobulin hinge region. In one embodiment, the spacer domain comprises the CH2 and CH3 domains of IgG1 or IgG4.

The binding domain of the CAR may in some embodiments be followed by one or more "hinge domains," which play a role in positioning the antigen binding domain away from the effector cell surface to enable proper cell/cell contact, antigen binding and activation. A CAR may comprise one or more hinge domains between the binding domain and the transmembrane domain (TM). The hinge domain may be derived either from a natural, synthetic, semi-synthetic, or recombinant source. The hinge domain can include the amino acid sequence of a naturally occurring immunoglobulin hinge region or an altered immunoglobulin hinge region. Illustrative hinge domains suitable for use in the CARs described herein include the hinge region derived from the extracellular regions of type 1 membrane proteins such as CD8 alpha, CD4, CD28, PD1, CD 152, and CD7, which may be wild-type hinge regions from these molecules or may be altered. In another embodiment, the hinge domain comprises a PD1, CD 152, or CD8 alpha hinge region.

The "transmembrane domain" is the portion of the CAR that fuses the extracellular binding portion and intracellular signaling domain and anchors the CAR to the plasma membrane of the immune effector cell. The TM domain may be derived either from a natural, synthetic, semi-synthetic, or recombinant source. The TM domain may be derived from the alpha, beta or zeta chain of the T-cell receptor, CD38, CD3Z, CD4, CD5, CD8 alpha, CD9, CD 16, CD22, CD27, CD28, CD33, CD37, CD45, CD64, CD80, CD86, CD 134, CD 137, CD 152, CD 154, and PD1. In one embodiment, the CARs contemplated herein comprise a TM domain derived from CD8 alpha or CD28.

In particular embodiments, CARs contemplated herein comprise an intracellular signaling domain. An "intracellular signaling domain," refers to the part of a CAR that participates in transducing the message of effective anti-BCMA CAR binding to a human BCMA polypeptide into the interior of the immune effector cell to elicit effector cell function, e.g., activation, cytokine production, proliferation and cytotoxic activity, including the release of cytotoxic factors to the CAR-bound target cell, or other cellular responses elicited with antigen binding to the extracellular CAR domain. The term "effector function" refers to a specialized function of an immune effector cell. Effector function of the T cell, for example, may be cytolytic activity or help or activity including the secretion of a cytokine. Thus, the term "intracellular signaling domain" refers to the portion of a protein which transduces the effector function signal and that directs the cell to perform a specialized function.

CARs contemplated herein comprise one or more co-stimulatory signaling domains to enhance the efficacy, expansion and/or memory formation of T cells expressing CAR receptors. As used herein, the term, "co-stimulatory signaling domain" refers to an intracellular signaling domain of a co-stimulatory molecule. Co-stimulatory molecules are cell surface molecules other than antigen receptors or Fc receptors that provide a second signal required for efficient activation and function of T lymphocytes upon binding to antigen.

Polypeptides

"Peptide" "polypeptide", "polypeptide fragment" and "protein" are used interchangeably, unless specified to the contrary, and according to conventional meaning, i.e., as a sequence of amino acids. Polypeptides are not limited to a specific length, e.g., they may comprise a full length protein sequence or a fragment of a full length protein, and may include post-translational modifications of the polypeptide, for example, glycosylations, acetylations, phosphorylations and the like, as well as other modifications known in the art, both naturally occurring and non-naturally occurring.

In various embodiments, the CAR polypeptides contemplated herein comprise a signal (or leader) sequence at the N-terminal end of the protein, which co-translationally or post-translationally directs transfer of the protein. Polypeptides can be prepared using any of a variety of well-known recombinant and/or synthetic techniques. Polypeptides contemplated herein specifically encompass the CARs of the present disclosure, or sequences that have deletions from, additions to, and/or substitutions of one or more amino acid of a CAR as disclosed herein.

An "isolated peptide" or an "isolated polypeptide" and the like, as used herein, refer to in vitro isolation and/or purification of a peptide or polypeptide molecule from a cellular environment, and from association with other components of the cell, i.e., it is not significantly associated with in vivo substances. Similarly, an "isolated cell" refers to a cell that has been obtained from an in vivo tissue or organ and is substantially free of extracellular matrix.

Nucleic Acids

As used herein, the terms "polynucleotide" or "nucleic acid molecule" refers to messenger RNA (mRNA), RNA, genomic RNA (gRNA), plus strand RNA (RNA(+)), minus strand RNA (RNA(−)), genomic DNA (gDNA), complementary DNA (cDNA) or recombinant DNA. Polynucleotides include single and double stranded polynucleotides. Preferably, polynucleotides of the invention include polynucleotides or variants having at least about 50%, 55%, 60%, 65%, 70%, 75%, 80%, 85%, 90%, 95%, 96%, 97%, 98%, 99% or 100%) sequence identity to any of the reference sequences described herein, typically where the variant maintains at least one biological activity of the reference sequence. In various illustrative embodiments, the present invention contemplates, in part, polynucleotides comprising expression vectors, viral vectors, and transfer plasmids, and compositions, and cells comprising the same.

Polynucleotides can be prepared, manipulated and/or expressed using any of a variety of well-established techniques known and available in the art. In order to express a desired polypeptide, a nucleotide sequence encoding the polypeptide, can be inserted into appropriate vector. Examples of vectors are plasmid, autonomously replicating sequences, and transposable elements. Additional exemplary vectors include, without limitation, plasmids, phagemids, cosmids, artificial chromosomes such as yeast artificial chromosome (YAC), bacterial artificial chromosome (BAC), or PI-derived artificial chromosome (PAC), bacteriophages such as lambda phage or MI 3 phage, and animal viruses. Examples of categories of animal viruses useful as vectors include, without limitation, retrovirus (including lentivirus), adenovirus, adeno-associated virus, herpesvirus {e.g., herpes simplex virus), poxvirus, baculovirus, papillomavirus, and papovavirus {e.g., SV40). Examples of expression vectors are pClneo vectors (Promega) for expression in mammalian cells; pLenti4/V5-DEST™, pLenti6/V5-DEST™, and pLenti6.2/V5-GW/lacZ (Invitrogen) for lentivirus-mediated gene transfer and expression in mammalian cells. In particular embodiments, the coding sequences of the chimeric proteins disclosed herein can be ligated into such expression vectors for the expression of the chimeric protein in mammalian cells. The "control elements" or "regulatory sequences" present in an expression vector are those non-translated regions of the vector—origin of replication, selection cassettes, promoters, enhancers, translation initiation signals (Shine Dalgarno sequence or Kozak sequence) introns, a polyadenylation sequence, 5' and 3' untranslated regions-which interact with host cellular proteins to carry out transcription and translation. Such elements may vary in their strength and specificity. Depending on the vector system and host utilized, any number of suitable transcription and translation elements, including ubiquitous promoters and inducible promoters may be used.

Vectors

In particular embodiments, a cell {e.g., an immune effector cell, such as a T cell) is transduced with a retroviral vector, e.g., a lentiviral vector, encoding a CAR. For example, an immune effector cell is transduced with a vector encoding a CAR that comprises a humanized anti-BCMA antibody or antigen binding fragment that binds a BCMA polypeptide, with a transmembrane and intracellular signaling domain, such that these transduced cells can elicit a CAR-mediated cytotoxic response.

Retroviruses are a common tool for gene delivery. In particular embodiments, a retrovirus is used to deliver a polynucleotide encoding a chimeric antigen receptor (CAR) to a cell. As used herein, the term "retrovirus" refers to an RNA virus that reverse transcribes its genomic RNA into a linear double-stranded DNA copy and subsequently covalently integrates its genomic DNA into a host genome. Once the virus is integrated into the host genome, it is referred to as a "provirus." The provirus serves as a template for RNA polymerase II and directs the expression of RNA molecules which encode the structural proteins and enzymes needed to produce new viral particles.

Illustrative retroviruses suitable for use in particular embodiments, include, but are not limited to: Moloney murine leukemia virus (M-MuLV), Moloney murine sarcoma virus (MOMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV)) and lenti virus.

As used herein, the term "lentivirus" refers to a group (or genus) of complex retroviruses. Illustrative lentiviruses include, but are not limited to: HIV (human immunodeficiency virus; including HIV type 1, and HIV type 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV). In one embodiment, HIV based vector backbones (i.e., HIV cis-acting sequence elements) are preferred. In particular embodiments, a lentivirus is used to deliver a polynucleotide comprising a CAR to a cell.

The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA. Useful vectors include, for example, plasmids (e.g., DNA plasmids or RNA plasmids), transposons, cosmids, bacterial artificial chromosomes, and viral vectors. Useful viral vectors include, e.g., replication defective retroviruses and lentiviruses.

As will be evident to one of skill in the art, the term "viral vector" is widely used to refer either to a nucleic acid molecule (e.g., a transfer plasmid) that includes virus-derived nucleic acid elements that typically facilitate transfer of the nucleic acid molecule or integration into the genome of a cell or to a viral particle that mediates nucleic acid transfer. Viral particles will typically include various viral components and sometimes also host cell components in addition to nucleic acid(s).

The term viral vector may refer either to a virus or viral particle capable of transferring a nucleic acid into a cell or to the transferred nucleic acid itself. Viral vectors and transfer plasmids contain structural and/or functional genetic elements that are primarily derived from a virus. The term "retroviral vector" refers to a viral vector or plasmid containing structural and functional genetic elements, or portions thereof, that are primarily derived from a retrovirus. In a preferred embodiment the invention therefore relates to a method for transfecting cells with an expression vector encoding a CAR. For example, in some embodiments, the vector comprises additional sequences, such as sequences that facilitate expression of the CAR, such a promoter, enhancer, poly-A signal, and/or one or more introns. In preferred embodiments, the CAR-coding sequence is flanked by transposon sequences, such that the presence of a transposase allows the coding sequence to integrate into the genome of the transfected cell.

In some embodiments, the genetically transformed cells are further transfected with a transposase that facilitates integration of a CAR coding sequence into the genome of the transfected cells. In some embodiments the transposase is provided as DNA expression vector. However, in preferred embodiments, the transposase is provided as an expressible RNA or a protein such that long-term expression of the transposase does not occur in the transgenic cells. For example, in some embodiments, the transposase is provided as an mRNA (e.g., an mRNA comprising a cap and poly-A tail). Any transposase system may be used in accordance with the embodiments of the present invention. However, in some embodiments, the transposase is salmonid-type Tel-like transposase (SB). For example, the transposase can be the so called "Sleeping beauty" transposase, see e.g., U.S. Pat. No. 6,489,458, incorporated herein by reference. In some embodiments, the transposase is an engineered enzyme with increased enzymatic activity. Some specific examples of transposases include, without limitation, SB 10, SB 11 or SB 100X transposase (see, e.g., Mates et al, 2009, Nat Genet. 41 (6): 753-61, or U.S. Pat. No. 9,228,180, herein incorporated by reference). For example, a method can involve electroporation of cells with an mRNA encoding an SB 10, SB 11 or SB 100X transposase.

Sequence Variants:

Sequence variants of the claimed nucleic acids, proteins, antibodies, antibody fragments and/or CARs, for example those defined by % sequence identity, that maintain similar binding properties of the invention are also included in the scope of the invention. Such variants, which show alternative sequences, but maintain essentially the same binding properties, such as target specificity, as the specific sequences provided are known as functional analogues, or as functionally analogous. Sequence identity relates to the percentage of identical nucleotides or amino acids when carrying out a sequence alignment.

The recitation "sequence identity" as used herein refers to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 70%, 75%, 80%, 85%, 90%, 95%, 96%, 97%, 98%, 99% or 100% sequence identity to any of the reference sequences described herein, typically where the polypeptide variant maintains at least one biological activity of the reference polypeptide. It will be appreciated by those of ordinary skill in the art that, as a result of the degeneracy of the genetic code, there are many nucleotide sequences that encode a polypeptide as described herein. Some of these polynucleotides bear minimal homology or sequence identity to the nucleotide sequence of any native gene. Nonetheless, polynucleotides that vary due to differences in codon usage are specifically contemplated by the present invention. Deletions, substitutions and other changes in sequence that fall under the described sequence identity are also encompassed in the invention.

Protein sequence modifications, which may occur through substitutions, are also included within the scope of the invention. Substitutions as defined herein are modifications made to the amino acid sequence of the protein, whereby one or more amino acids are replaced with the same number of (different) amino acids, producing a protein which contains a different amino acid sequence than the primary protein. Substitutions may be carried out that preferably do not significantly alter the function of the protein. Like additions, substitutions may be natural or artificial. It is well known in the art that amino acid substitutions may be made without significantly altering the protein's function. This is particularly true when the modification relates to a "conservative" amino acid substitution, which is the substitution of one amino acid for another of similar properties. Such "conserved" amino acids can be natural or synthetic amino acids which because of size, charge, polarity and conformation can be substituted without significantly affecting the structure and function of the protein. Frequently, many amino acids may be substituted by conservative amino acids without deleteriously affecting the protein's function.

In general, the non-polar amino acids Gly, Ala, Val, Ile and Leu; the non-polar aromatic amino acids Phe, Trp and Tyr; the neutral polar amino acids Ser, Thr, Cys, Gln, Asn and Met; the positively charged amino acids Lys, Arg and His; the negatively charged amino acids Asp and Glu, represent groups of conservative amino acids. This list is not exhaustive. For example, it is well known that Ala, Gly, Ser and sometimes Cys can substitute for each other even though they belong to different groups.

Substitution variants have at least one amino acid residue in the antibody molecule removed and a different residue inserted in its place. The sites of greatest interest for substitutional mutagenesis include the hypervariable regions, but FR alterations are also contemplated. If such substitutions result in a change in biological activity, then more substantial changes, denominated "exemplary substitutions" in the table immediately below, or as further described below in reference to amino acid classes, may be introduced and the products screened. Potential Amino Acid Substitutions:

| Original residue | Preferred conservative substitutions | Examples of exemplary substitutions |
|---|---|---|
| Ala (A) | Val | Val; Leu; Ile |
| Asg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn, Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain.

Conservative amino acid substitutions are not limited to naturally occurring amino acids, but also include synthetic amino acids. Commonly used synthetic amino acids are omega amino acids of various chain lengths and cyclohexyl alanine which are neutral non-polar analogs; citrulline and methionine sulfoxide which are neutral non-polar analogs, phenylglycine which is an aromatic neutral analog; cysteic acid which is a negatively charged analog and ornithine which is a positively charged amino acid analog. Like the naturally occurring amino acids, this list is not exhaustive, but merely exemplary of the substitutions that are well known in the art.

Genetically Modified Cells and Immune Cells

The present invention contemplates, in particular embodiments, cells genetically modified to express the CARs contemplated herein, for use in the treatment of B cell related conditions. As used herein, the term "genetically engineered" or "genetically modified" refers to the addition of extra genetic material in the form of DNA or RNA into the total genetic material in a cell. The terms, "genetically modified cells," "modified cells," and, "redirected cells," are used interchangeably. As used herein, the term "gene therapy" refers to the introduction of extra genetic material in the form of DNA or RNA into the total genetic material in a cell that restores, corrects, or modifies expression of a gene, or for the purpose of expressing a therapeutic polypeptide, e.g., a CAR. In particular embodiments, the CARs contemplated herein are introduced and expressed in immune effector cells so as to redirect their specificity to a target antigen of interest, e.g., a BCMA polypeptide.

An "immune cell" or "immune effector cell" is any cell of the immune system that has one or more effector functions (e.g., cytotoxic cell killing activity, secretion of cytokines, induction of ADCC and/or CDC).

Immune effector cells of the invention can be autologous/ autogeneic ("self") or non-autologous ("non-self," e.g., allogeneic, syngeneic or xenogeneic). "Autologous," as used herein, refers to cells from the same subject, and represent a preferred embodiment of the invention.

"Allogeneic," as used herein, refers to cells of the same species that differ genetically to the cell in comparison. "Syngeneic," as used herein, refers to cells of a different subject that are genetically identical to the cell in comparison. "Xenogeneic," as used herein, refers to cells of a different species to the cell in comparison. In preferred embodiments, the cells of the invention are autologous or allogeneic.

Illustrative immune effector cells used with the CARs contemplated herein include T lymphocytes. The terms "T cell" or "T lymphocyte" are art-recognized and are intended to include thymocytes, immature T lymphocytes, mature T lymphocytes, resting T lymphocytes, cytokine-induced killer cells (CIK cells) or activated T lymphocytes. Cytokine-induced killer (CIK) cells are typically CD3- and CD56-positive, non-major histocompatibility complex (MHC)-restricted, natural killer (NK)-like T lymphocytes. A T cell can be a T helper (Th) cell, for example a T helper 1 (Th1) or a T helper 2 (Th2) cell. The T cell can be a helper T cell (HTL; CD4+ T cell) CD4+ T cell, a cytotoxic T cell (CTL; CD8+ T cell), CD4+CD8+ T cell, CD4 CD8 T cell, or any other subset of T cells. Other illustrative populations of T cells suitable for use in particular embodiments include naive T cells and memory T cells.

For example, when reintroduced back to patients after autologous cell transplantation, the T cells modified with the CAR of the invention as described herein may recognize and kill tumor cells. CIK cells may have enhanced cytotoxic activity compared to other T cells, and therefore represent a preferred embodiment of an immune cell of the present invention.

As would be understood by the skilled person, other cells may also be used as immune effector cells with the CARs as described herein. In particular, immune effector cells also include NK cells, NKT cells, neutrophils, and macrophages. Immune effector cells also include progenitors of effector cells wherein such progenitor cells can be induced to differentiate into an immune effector cells in vivo or in vitro.

The present invention provides methods for making the immune effector cells which express the CAR contemplated herein. In one embodiment, the method comprises transfecting or transducing immune effector cells isolated from an individual such that the immune effector cells express one or more CAR as described herein. In certain embodiments, the immune effector cells are isolated from an individual and genetically modified without further manipulation in vitro. Such cells can then be directly re-administered into the individual. In further embodiments, the immune effector cells are first activated and stimulated to proliferate in vitro prior to being genetically modified to express a CAR. In this regard, the immune effector cells may be cultured before and/or after being genetically modified (i.e., transduced or transfected to express a CAR contemplated herein).

In particular embodiments, prior to in vitro manipulation or genetic modification of the immune effector cells described herein, the source of cells is obtained from a subject. In particular embodiments, the CAR-modified immune effector cells comprise T cells. T cells can be obtained from a number of sources including, but not limited to, peripheral blood mononuclear cells, bone marrow, lymph nodes tissue, cord blood, thymus issue, tissue from a site of infection, ascites, pleural effusion, spleen tissue, and tumors. In certain embodiments, T cells can be obtained from a unit of blood collected from a subject using any number of techniques known to the skilled person, such as sedimentation, e.g., FICOLL™ separation, antibody-conjugated bead-based methods such as MACS™ separation (Miltenyi). In one embodiment, cells from the circulating blood of an individual are obtained by apheresis. The apheresis product typically contains lymphocytes, including T cells, monocytes, granulocyte, B cells, other nucleated white blood cells, red blood cells, and platelets. In one embodiment, the cells collected by apheresis may be washed to remove the plasma fraction and to place the cells in an appropriate buffer or media for subsequent processing. The cells can be washed with PBS or with another suitable solution that lacks calcium, magnesium, and most, if not all other, divalent cations. As would be appreciated by those of ordinary skill in the art, a washing step may be accomplished by methods known to those in the art, such as by using a semiautomated flow-through centrifuge. For example, the Cobe 2991 cell processor, the Baxter CytoMate, or the like. After washing, the cells may be resuspended in a variety of biocompatible buffers or other saline solution with or without buffer. In certain embodiments, the undesirable components of the apheresis sample may be removed in the cell directly resuspended culture media.

In certain embodiments, T cells are isolated from peripheral blood mononuclear cells (PBMCs) by lysing the red blood cells and depleting the monocytes, for example, by centrifugation through a PERCOLL™ gradient. A specific subpopulation of T cells can be further isolated by positive or negative selection techniques. One method for use herein is cell sorting and/or selection via negative magnetic immunoadherence or flow cytometry that uses a cocktail of monoclonal antibodies directed to cell surface markers present on the cells negatively selected.

PBMC may be directly genetically modified to express CARs using methods contemplated herein. In certain embodiments, after isolation of PBMC, T lymphocytes are further isolated and in certain embodiments, both cytotoxic and helper T lymphocytes can be sorted into naive, memory, and effector T cell subpopulations either before or after genetic modification and/or expansion. CD8+ cells can be obtained by using standard methods. In some embodiments, CD8+ cells are further sorted into naive, central memory, and effector cells by identifying cell surface antigens that are associated with each of those types of CD8+ cells.

The immune effector cells, such as T cells, can be genetically modified following isolation using known methods, or the immune effector cells can be activated and expanded (or differentiated in the case of progenitors) in vitro prior to being genetically modified. In a particular embodiment, the immune effector cells, such as T cells, are genetically modified with the chimeric antigen receptors contemplated herein {e.g., transduced with a viral vector comprising a nucleic acid encoding a CAR) and then are activated and expanded in vitro. In various embodiments, T cells can be activated and expanded before or after genetic modification to express a CAR, using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

In a further embodiment, a mixture of, e.g., one, two, three, four, five or more, different expression vectors can be used in genetically modifying a donor population of immune effector cells wherein each vector encodes a different chimeric antigen receptor protein as contemplated herein. The resulting modified immune effector cells forms a mixed population of modified cells, with a proportion of the modified cells expressing more than one different CAR proteins.

In one embodiment, the invention provides a method of storing genetically modified murine, human or humanized CAR protein expressing immune effector cells which target a BCMA protein, comprising cryopreserving the immune effector cells such that the cells remain viable upon thawing. A fraction of the immune effector cells expressing the CAR proteins can be cryopreserved by methods known in the art to provide a permanent source of such cells for the future treatment of patients afflicted with the B cell related condition. When needed, the cryopreserved transformed immune effector cells can be thawed, grown and expanded for more such cells.

Compositions and Formulations

The compositions contemplated herein may comprise one or more polypeptides, polynucleotides, vectors comprising same, genetically modified immune effector cells, etc., as contemplated herein. Compositions include, but are not limited to pharmaceutical compositions. A "pharmaceutical composition" refers to a composition formulated in pharmaceutically-acceptable or physiologically-acceptable solutions for administration to a cell or an animal, either alone, or in combination with one or more other modalities of therapy. It will also be understood that, if desired, the compositions of the invention may be administered in combination with other agents as well, such as, e.g., cytokines, growth factors, hormones, small molecules, chemotherapeutics, pro-drugs, drugs, antibodies, or other various pharmaceutically-active agents. There is virtually no limit to other components that may also be included in the compositions, provided that the additional agents do not adversely affect the ability of the composition to deliver the intended therapy.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, or emulsifier which has been approved by the United States Food and Drug Administration as being acceptable for use in humans or domestic animals. Exemplary pharmaceutically acceptable carriers include, but are not limited to, to sugars, such as lactose, glucose and sucrose; starches, such as corn starch and potato starch; cellulose, and its derivatives, such as sodium carboxymethyl cellulose, ethyl cellulose and cellulose acetate; tragacanth; malt; gelatin; talc; cocoa butter, waxes, animal and vegetable fats, paraffins, silicones, bentonites, silicic acid, zinc oxide; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and any other compatible substances employed in pharmaceutical formulations.

In particular embodiments, compositions of the present invention comprise an amount of CAR-expressing immune effector cells contemplated herein. As used herein, the term "amount" refers to "an amount effective" or "an effective amount" of a genetically modified therapeutic cell, e.g., T cell, to achieve a beneficial or desired prophylactic or therapeutic result, including clinical results.

A "prophylactically effective amount" refers to an amount of a genetically modified therapeutic cell effective to achieve the desired prophylactic result. Typically but not necessarily, since a prophylactic dose is used in subjects prior to or at an earlier stage of disease, the prophylactically effective amount is less than the therapeutically effective amount. The term prophylactic does not necessarily refer to a complete prohibition or prevention of a particular medical disorder. The tem prophylactic also refers to the reduction of risk of a certain medical disorder occurring or worsening in its symptoms.

A "therapeutically effective amount" of a genetically modified therapeutic cell may vary according to factors such as the disease state, age, sex, and weight of the individual, and the ability of the stem and progenitor cells to elicit a desired response in the individual. A therapeutically effective amount is also one in which any toxic or detrimental effects of the virus or transduced therapeutic cells are outweighed by the therapeutically beneficial effects. The term "therapeutically effective amount" includes an amount that is effective to "treat" a subject {e.g., a patient). When a therapeutic amount is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^2$ to $10^{10}$ cells/kg body weight, preferably $10^5$ to $10^6$ cells/kg body weight, including all integer values within those ranges. The number of cells will depend upon the ultimate use for which the composition is intended as will the type of cells included therein. For uses provided herein, the cells are generally in a volume of a liter or less, can be 500 mLs or less, even 250 mLs or 100 mLs or less. Hence the density of the desired cells is typically greater than $10^6$ cells/ml and generally is greater than $10^7$ cells/ml, generally $10^8$ cells/ml or greater. The clinically relevant number of immune cells can be apportioned into multiple infusions that cumulatively equal or exceed $10^5$, $10^6$, $10^7$, $10^8$, $10^9$, $10^{10}$, $10^{11}$, or $10^{12}$ cells. In some aspects of the present invention, particularly since all the infused cells will be redirected to a particular target antigen, lower numbers of cells may be administered. CAR expressing cell compositions may be administered multiple times at dosages within these ranges. The cells may be allogeneic, syngeneic, xenogeneic, or autologous to the patient undergoing therapy.

Generally, compositions comprising the cells activated and expanded as described herein may be utilized in the treatment and prevention of diseases that arise in individuals who are immunocompromised. In particular, compositions comprising the CAR-modified T cells contemplated herein are used in the treatment of B cell malignancies. The CAR-modified T cells of the present invention may be administered either alone, or as a pharmaceutical composition in combination with carriers, diluents, excipients, and/or with other components such as IL-2 or other cytokines or cell populations. In particular embodiments, pharmaceutical compositions contemplated herein comprise an amount of genetically modified T cells, in combination with one or more pharmaceutically or physiologically acceptable carriers, diluents or excipients.

Pharmaceutical compositions of the present invention comprising a CAR-expressing immune effector cell population, such as T cells, may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for parenteral administration, e.g., intravascular (intravenous or intraarterial), intraperitoneal or intramuscular administration.

The liquid pharmaceutical compositions, whether they be solutions, suspensions or other like form, may include one or more of the following: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. An injectable pharmaceutical composition is preferably sterile.

In a particular embodiment, compositions contemplated herein comprise an effective amount of CAR-expressing immune effector cells, alone or in combination with one or more therapeutic agents. Thus, the CAR-expressing immune effector cell compositions may be administered alone or in combination with other known cancer treatments, such as radiation therapy, chemotherapy, transplantation, immunotherapy, hormone therapy, photodynamic therapy, etc. The compositions may also be administered in combination with antibiotics. Such therapeutic agents may be accepted in the art as a standard treatment for a particular disease state as described herein, such as a particular cancer. Exemplary therapeutic agents contemplated include cytokines, growth factors, steroids, NSAIDs, DMARDs, anti-inflammatories, chemotherapeutics, radiotherapeutics, therapeutic antibodies, or other active and ancillary agents.

Therapeutic Methods

The genetically modified immune effector cells contemplated herein provide improved methods of adoptive immunotherapy for use in the treatment of B cell related conditions that include, but are not limited to immunoregulatory conditions and hematological malignancies. In particular embodiments, compositions comprising immune effector cells comprising the CARs contemplated herein are used in the treatment of conditions associated with abnormal B cell activity, otherwise termed as a "medical disorder associated with the presence of pathogenic B cells".

As use herein, "medical disorder associated with the presence of pathogenic B cells" or "B cell malignancy" refers to a medical condition, such as cancer, that forms in B cells. In particular embodiments, compositions comprising CAR-modified T cells contemplated herein are used in the treatment of hematologic malignancies, including but not limited to B cell malignancies such as, for example, multiple myeloma (MM) and non-Hodgkin's lymphoma (NHL).

In another aspect of the present invention there is provided a CAR and CAR-T according to the invention as herein described for use in the treatment of a B-cell mediated or plasma cell mediated disease or antibody mediated disease or disorder selected from Multiple Myeloma (MM), chronic lymphocytic leukemia (CLL), Non-secretory multiple myeloma, Smoldering multiple myeloma, Monoclonal gammopathy of undetermined significance (MGUS), Solitary plasmacytoma (Bone, extramedullary), Lymphoplasmacytic lymphoma (LPL), Waldenstrom's Macroglobulinemia, Plasma cell leukemia, Primary Amyloidosis (AL), Heavy chain disease, Systemic lupus erythematosus (SLE), POEMS syndrome/osteosclerotic myeloma, Type I and II cryoglobulinemia, Light chain deposition disease, Goodpasture's syndrome, Idiopathic thrombocytopenia purpura (ITP), Acute glomerulonephritis, Pemphigus and Pemphigoid disorders, and Epidermolysis bullosa acquisita; or any Non-Hodgkin's Lymphoma B-cell leukemia or Hodgkin's lymphoma (HL) with BCMA expression or any diseases in which patients develop neutralising antibodies to recombinant protein replacement therapy wherein said method comprises the step of administering to said patient a therapeutically effective amount of the CAR or CAR-T as described herein.

Multiple myeloma is a B cell malignancy of mature plasma cell morphology characterized by the neoplastic transformation of a single clone of these types of cells. These plasma cells proliferate in BM and may invade adjacent bone and sometimes the blood. Variant forms of multiple myeloma include overt multiple myeloma, smoldering multiple myeloma, plasma cell leukemia, non-secretory myeloma, IgD myeloma, osteosclerotic myeloma, solitary plasmacytoma of bone, and extramedullary Plasmacytoma.

Non-Hodgkin lymphoma encompasses a large group of cancers of lymphocytes (white blood cells). Non-Hodgkin lymphomas can occur at any age and are often marked by lymph nodes that are larger than normal, fever, and weight loss. Non-Hodgkin lymphomas can also present on extranodal sites, such as the central nervous system, mucosal tissues including lung, intestine, colon and gut. There are many different types of non-Hodgkin lymphoma. For example, non-Hodgkin's lymphoma can be divided into aggressive (fast-growing) and indolent (slow-growing) types. Although non-Hodgkin lymphomas can be derived from B cells and T-cells, as used herein, the term "non-Hodgkin lymphoma" and "B cell non-Hodgkin lymphoma" are used interchangeably. B cell non-Hodgkin lymphomas (NHL) include Burkitt lymphoma, chronic lymphocytic leukemia/small lymphocytic lymphoma (CLL/SLL), diffuse large B cell lymphoma, follicular lymphoma, immunoblastic large cell lymphoma, precursor B-lymphoblastic lymphoma, and mantle cell lymphoma. Lymphomas that occur after bone marrow or stem cell transplantation are usually B cell non-Hodgkin lymphomas.

Chronic lymphocytic leukemia (CLL) is an indolent (slow-growing) cancer that causes a slow increase in immature white blood cells called B lymphocytes, or B cells. Cancer cells spread through the blood and bone marrow, and can also affect the lymph nodes or other organs such as the liver and spleen. CLL eventually causes the bone marrow to fail. A different presentation of the disease is called small lymphocytic lymphoma and localizes mostly to secondary lymphoid organs, e.g. lymph nodes and spleen.

In one embodiment of the invention the CAR or immune cell expressing said CAR is intended for use in the treatment of an autoimmune disease, preferably an auto-antibody-dependent autoimmune disease, preferably an autoimmune disease with an inflammatory component, whereby the autoimmune disease is preferably selected from Takayasu Arteritis, Giant-cell arteritis, familial Mediterranean fever, Kawasaki disease, Polyarteritis nodosa, cutaneous Polyarteritis nodosa, Hepatitis-associated arteritis, Behcet's syndrome, Wegener's granulomatosis, ANCA-vasculitides, Churg-Strauss syndrome, microscopic polyangiitis, Vasculitis of connective tissue diseases, Henoch-Schönlein purpura, Cryoglobulinemic vasculitis, Cutaneous leukocytoclastic angiitis, Tropical aortitis, Sarcoidosis, Cogan's syndrome, Wiskott-Aldrich Syndrome, Lepromatous arteritis, Primary angiitis of the CNS, Thromboangiitis obliterans, Paraneoplastic arthritis, Urticaria, Dego's disease, Myelodysplastic syndrome, Erythema elevatum diutinum, Hyperimmunoglobulin D, Allergic Rhinitis, Asthma bronchiale, chronic obstructive pulmonary disease, periodontitis, Rheumatoid Arthritis, atherosclerosis, Amyloidosis, Morbus Chron, Colitis ulcerosa, Autoimmune Myositis, Diabetes mellitus, Guillain-Barre Syndrome, histiocytosis, Osteoarthritis, atopic dermatitis, periodontitis, chronic rhinosinusitis, Psoriasis, psoriatic arthritis, Microscopic colitis, Pulmonary fibrosis, glomerulonephritis, Whipple's disease, Still's disease, erythema nodosum, otitis, cryoglobulinemia, Sjogren's syndrome, Lupus erythematosus, preferably systemic lupus erythematosus (SLE), aplastic anemia, Osteomyelofibrosis, chronic inflammatory demyelinating polyneuropathy, Kimura's disease, systemic sclerosis, chronic periaortitis, chronic prostatitis, idiopathic pulmonary fibrosis, chronic granulomatous disease, Idiopathic achalasia, bleomycin-induced lung inflammation, cytarabine-induced lung inflammation, Autoimmunthrombocytopenia, Autoimmunneutropenia, Autoimmunhemolytic anemia, Autoimmunlymphocytopenia, Chagas' disease, chronic autoimmune thyroiditis, autoimmune hepatitis, Hashimoto's Thyroiditis, atropic thyroiditis, Graves disase, Autoimmune polyglandular syndrome, Autoimmune Addison Syndrome, *Pemphigus vulgaris, Pemphigus foliaceus*, Dermatitis herpetiformis, Autoimmune alopecia, Vitiligo, Antiphospholipid syndrome, Myasthenia gravis, Stiff-man syndrome, Goodpasture's syndrome, Sympathetic ophthalmia, Folliculitis, Sharp syndrome and/or Evans syndrome, in particular hay fever, periodontitis, atherosclerosis, rheumatoid arthritis, most preferably SLE.

Systemic lupus erythematosus (SLE), also known as lupus, is an autoimmune disease in which the body's immune system attacks healthy tissue in various parts of the body. Symptoms vary between people and may be mild to severe. Common symptoms include painful and swollen joints, fever, chest pain, hair loss, mouth ulcers, swollen lymph nodes, feeling tired, and a red rash which is most commonly on the face.

As used herein, the terms "individual" and "subject" are often used interchangeably and refer to any animal that exhibits a symptom of a disease, disorder, or condition that can be treated with the gene therapy vectors, cell-based therapeutics, and methods disclosed elsewhere herein. In preferred embodiments, a subject includes any animal that exhibits symptoms of a disease, disorder, or condition of the hematopoietic system, e.g., a B cell malignancy, that can be treated with the gene therapy vectors, cell-based therapeutics, and methods disclosed elsewhere herein. Suitable subjects include laboratory animals (such as mouse, rat, rabbit, or guinea pig), farm animals, and domestic animals or pets (such as a cat or dog). Non-human primates and, preferably, human patients, are included. Typical subjects include human patients that have a B cell malignancy, have been diagnosed with a B cell malignancy, or are at risk or having a B cell malignancy.

As used herein "treatment" or "treating," includes any beneficial or desirable effect on the symptoms or pathology of a disease or pathological condition, and may include even minimal reductions in one or more measurable markers of the disease or condition being treated.

Treatment can involve optionally either the reduction or amelioration of symptoms of the disease or condition, or the delaying of the progression of the disease or condition. "Treatment" does not necessarily indicate complete eradication or cure of the disease or condition, or associated symptoms thereof.

As used herein, "prevent," and similar words such as "prevented," "preventing" or "prophylactic" etc., indicate an approach for preventing, inhibiting, or reducing the likelihood of the occurrence or recurrence of, a disease or condition. It also refers to delaying the onset or recurrence of a disease or condition or delaying the occurrence or recurrence of the symptoms of a disease or condition. As used herein, "prevention" and similar words also includes reducing the intensity, effect, symptoms and/or burden of a disease or condition prior to onset or recurrence of the disease or condition.

In one embodiment, a method of treating a B cell related condition in a subject in need thereof comprises administering an effective amount, e.g., therapeutically effective amount of a composition comprising genetically modified immune effector cells contemplated herein. The quantity and frequency of administration will be determined by such factors as the condition of the patient, and the type and severity of the patient's disease, although appropriate dosages may be determined by clinical trials.

The administration of the compositions contemplated herein may be carried out in any convenient manner, including by aerosol inhalation, injection, ingestion, transfusion, implantation or transplantation. In a preferred embodiment, compositions are administered parenterally. The phrases "parenteral administration" and "administered parenterally" as used herein refers to modes of administration other than enteral and topical administration, usually by injection, and includes, without limitation, intravascular, intravenous, intramuscular, intraarterial, intrathecal, intracapsular, intraorbital, intratumoral, intracardiac, intradermal, intraperitoneal, transtracheal, subcutaneous, subcuticular, intraarticular, subcapsular, subarachnoid, intraspinal and intrasternal injection and infusion. In one embodiment, the compositions contemplated herein are administered to a subject by direct injection into a tumor, lymph node, or site of infection.

BRIEF DESCRIPTION OF THE DRAWINGS

The invention is demonstrated by way of the example by the examples and figures disclosed herein. The figures provided herein represent particular embodiments of the invention and are not intended to limit the scope of the invention. The figures are to be considered as providing a further description of possible and potentially preferred embodiments that enhance the technical support of one or more non-limiting embodiments.

FIG. 2: Schematic representation of preferred CAR constructs IX, X; XI, XV, XVI, XVII.

FIG. 3: List of preferred constructs and potential combinations of the various structural elements of the CARs as described herein.

FIG. 4: Sequence comparisons between the mAb binding regions and the preferred humanized sequences employed in the present CAR.

FIG. 13: Sequence alignment of preferred humanized sequences of the HC compared to J22.9-xi.

FIG. 14: Sequence alignment of preferred humanized sequences of the LC compared to J22.9-xi.

FIG. 16: BCMA redirected CAR-T cells are effective against B-NHL tumors in a xenografted NSG mouse model. (A) Engraftment of mantle cell lymphomas in a xenografted NSG mouse model. Mice were challenged by i.v. transplantation of 6×10$^5$ JeKo-1 cells. At day 7 after tumor inoculation, tumor cell growth was visualized by IVIS imaging. IVIS exposure, 120 sec. (B) To follow treatment efficacy and to scale down bioluminescence intensity for better presentation, mice as in (A) were again imaged for 30 sec at day 0. Subsequent IVIS-exposures after CAR-T cell transfer, control SP6 CAR-T cells (n=7) and BCMA CAR-T cells (n=7), were done for 30 sec to allow better comparisons between day 0 and day 16 which has the highest intensity. (C) Mean values of bioluminescence signal intensities obtained from regions of interests covering the entire body of each mouse are plotted for each group at each time point.

EXAMPLES

The invention is demonstrated by way of the examples disclosed herein. The examples provide technical support for and a more detailed description of potentially preferred, non-limiting embodiments of the invention. In order to demonstrate the functionality of the CAR described herein, the inventors have performed the following experiments:

- co-cultures of CAR-transduced human T cells with different target cell lines show specific T cell activation by distinct BCMA+ MM and NHL cell lines; readout was release of IFN-gamma as effector cytokine from T cells;
- cytotoxicity assays reveal selective killing of BCMA+ cell lines; essentially no killing was seen in BCMA-negative cell lines or primary cells, e.g. HUVECs (endothelial origin), HEK293 (kidney), peripheral blood B cells, peripheral blood total leukocytes, T- and B-ALL, colon carcinoma.
- CD107a staining of co-cultured CAR-T cells with multiple myeloma cells, detection of degranulating CD8+ T cells upon antigen-specific (BCMA) stimulation by flow cytometry.
- In vivo experiments relate to using a xenotransplantation NSG mouse model to generate data on i) functionality, ii) off-target reactivity, iii) T cell memory, and iv) biosafety of adoptively transferred CAR-T cells against B-NHL and myeloma cell lines. For B-NHL the cytolytic capacity of anti-BCMA CAR-T cells is compared with an established anti-CD19 CAR-T cell product.

Example 1: Cloning and Plasmid Preparation

Figure 1:
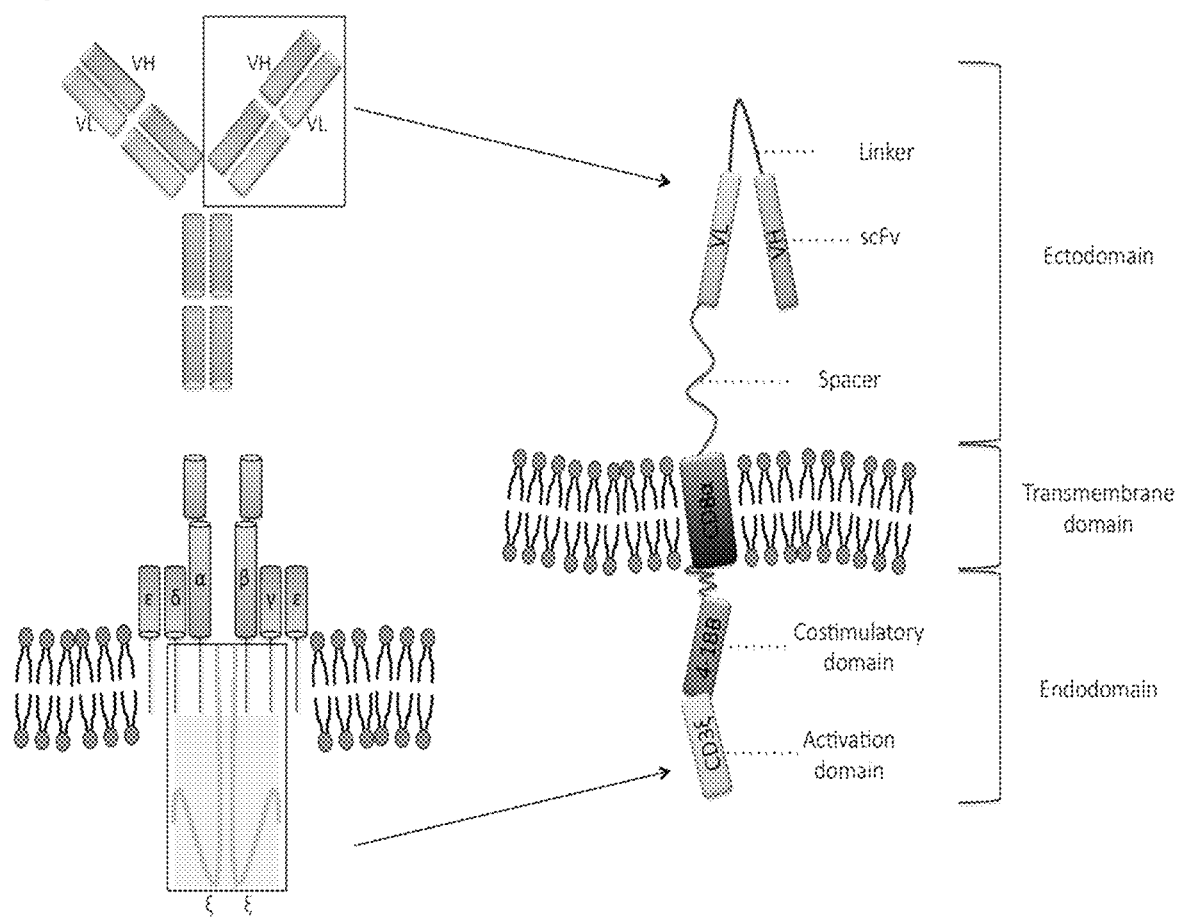
FIG. 1: Schematic representation of preferred CAR structures.
Figure 5:
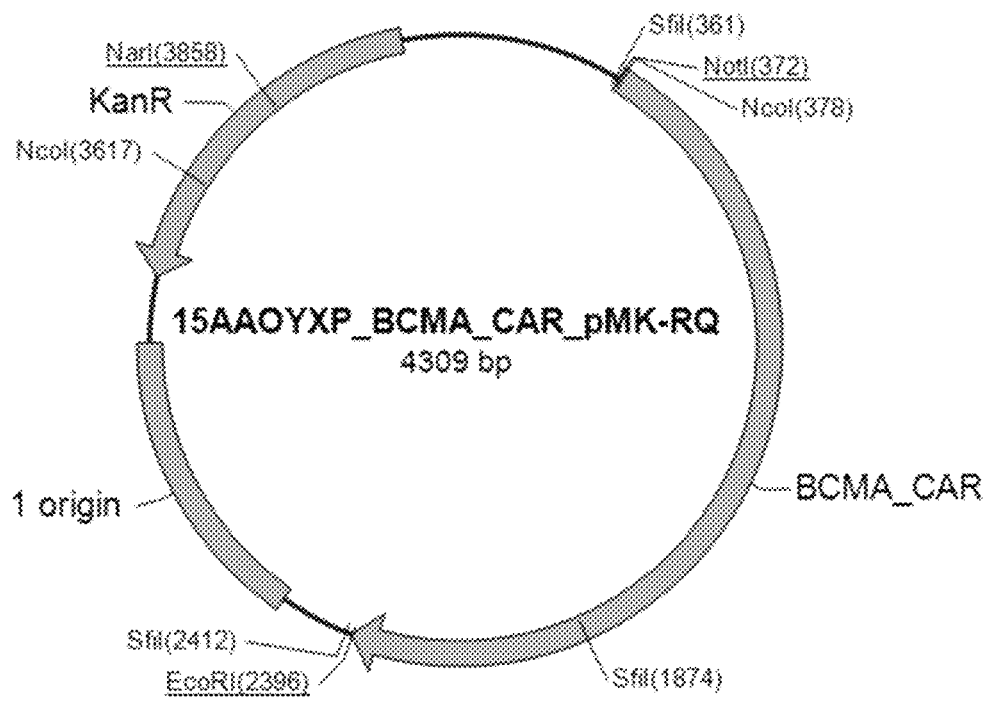
FIG. 5: GeneArt™ Plasmid with the BCMA-CAR Sequence.
Figure 6:
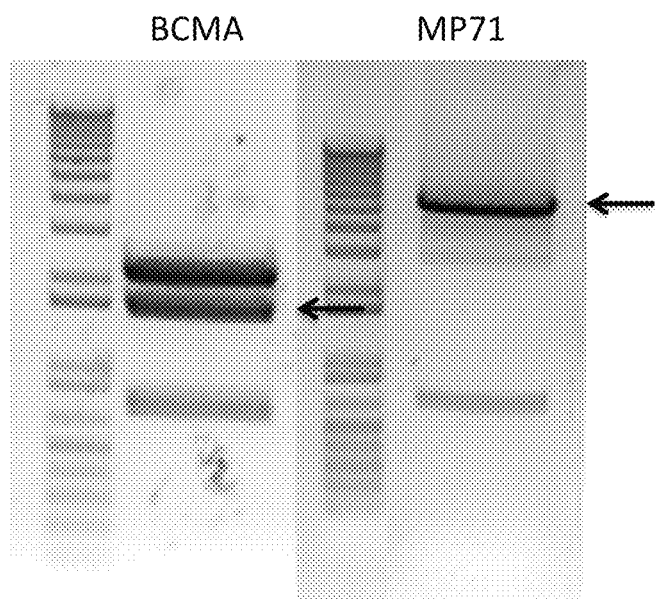
FIG. 6: Gel electrophoresis of the construct and vectors after restriction.

CAR sequences were synthesized using GeneArt™ (Gene Synthesis Service). Restriction digestion of the CAR construct was carried out using NotI and EcoRI (FIG. 5). The retroviral vector MP71 was also digested with NotI and EcoRI, and subsequently dephosphorylated. The CAR and vector were separated using gel electrophoresis (FIG. 6.) and the fragments were purified. The CAR construct was subsequently ligated into the vector (50 ng) at a ratio of 3:1. Transformation of the ligation mixture into MACH-1 was carried out (FIG. 3.). A control digest was conducted and the Mini-Preparation was sequenced. The constructs were subsequently re-transformed into MACH-1. A maxi-Preparation of the MP71-BCMA-CAR plasmid was produced.

MP71 is a single (+)-strand-RNA-Virus. Reverse-Transcriptase converts the retroviral RNA-Genome into a DNA copy. The DNA integrates as a provirus at a random position into the target genome. Through cell division the virus reproduces stably as a provirus.

Example 2: Transfection and Transduction

Day 0: Seeding HekT (293T)- or GalV-cells for virus production in 6 well plates
Day 1: Transient 3-plasmid transfection for retrovirus production (calcium phosphate transfection). Per well, 18 µg of DNA was used, in 250 mM Cacl2, 150 µl H2O, according to standard protocols. Cells are incubated for 6 h at 37° C., medium is exchanged, further incubation carried out for 48 h at 37° C.

Coating of 24-well non-tissue culture plates with anti-huCD3 und anti-huCD28 antibodies: Prepare anti-CD3/anti-CD28-antibody solution in PBS (5 µg/ml anti-CD3, 1 µg/ml anti-CD28), 0.5 ml per well. Incubate each well with 0.5 ml antibody solution for 2 h at 37° C., replace with sterile 2% BSA-solution (in water), incubation: 30 min (37° C.). Remove BSA-solution and wash wells with 2 ml PBS.

Purification of PBMCs from 40 ml Blood (~2.5×10$^7$ PBMCs):

Prepare 12.5 ml Ficoll-Gradient medium in 2×50 ml Falcon-Tube, dilute blood with RPMI (+100 IU/ml Penicillin, Streptomycin) to 45 ml, mix and coat with 22.5 ml Blood-Medium-mixture, centrifuge (20 min, 20° C., 1800 rpm, RZB *648, G 17.9). Discard 15 ml upper phase. Transfer remainder of the upper phase with white-milky PBMC-containing intermediate phase to a new 50 ml Falcon-Tube, fill to 45 ml with RPMI (+100 IU/ml Penicillin, Streptomycin) and centrifuge. Re-suspend pellets in 45 ml RPMI (+100 IU/ml Penicillin, Streptomycin), centrifuge, combine pellets in 10-20 ml T cell medium, stain one sample with trypan blue, count cells and add cells at a concentration of 1-1.5×10$^6$ cells/ml (T-cell medium (+100 IU/ml IL-2) corresponds to 400U/ml clinic-IL2) to the anti-CD3, anti-CD28 coated wells. Centrifuge remainder of PBMCs, suspend in freezing medium and store in Cryo tubes at −80° C.

Day 3: Transduction of PBLs

Remove and filter (0.45 µm filter) viral supernatant from Hekt- or GalV-cells. Treat stimulated PBMCs with 1.5 ml viral supernatant.

Day 4: Transduction of PBLs

Filter remaining viral supernatant (4° C.) and second supernatant from Hekt- or GalV-cells (0.45 µm). Collect 1 ml to 1.5 ml supernatant from the PBLs. Treat stimulated PBMCs with 1 ml to 1.5 ml viral supernatant and centrifuge in the CD3-/CD28-coated wells (90 min, 32° C., 2000 rpm). Final concentration of 100 IU/ml IL2 (1 ul von 400U/µl) or 10 ng/µl IL7 und 10 ng/µl IL15, and additionally 4 µg/ml (8 µl) Protamine sulfate. Centrifuge at 90 min 2000 rpm 32° C.

Day 7 to Day 13: Culture PBLs, treat T cell medium with fresh IL2 or IL7/IL15.

Day 13: End T-cell stimulation.

Rinse PBL-cultures from the cell culture flasks, centrifugation, re-suspend pellet in T-cell medium (+10 IU/ml IL2).

As of Day 15: Functional assays

Example 3: Functional In Vitro Testing of Anti-BCMA CAR T Cells

I. Confirmation of BCMA CAR-Expression on Human T Cells Following Retroviral Transduction Evidence was obtained of folding and transport of the CAR receptor in context of human T cells; the functionality of retrovirus transduction protocol was assessed.

Human peripheral blood leukocytes were purified via a Ficoll gradient. Cells were cultured, stimulated and retrovirally transduced as described above. Following transduction, cells were further cultured in either IL-2 or IL-7/IL-15 containing medium prior to the analysis of BCMA-CAR expression.

Figure 7:
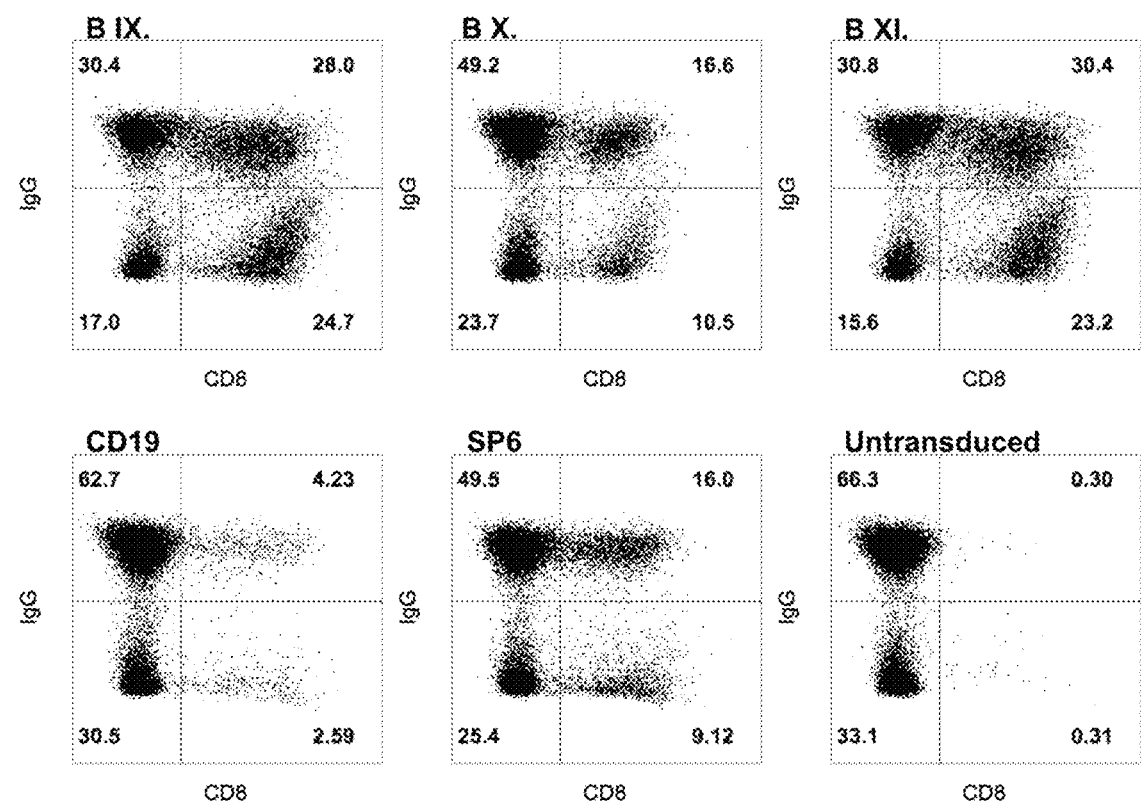
FIG. 7: Confirmation of BCMA CAR-expression on human T cells following retroviral transduction: CAR Expression, constructs IX-XII, CD19, SP6.

Transduction rate and viability were assessed by flow cytometry (FACS) analysis. To detect BCMA-CAR expression, cells were stained with anti-human Ig-antibody that recognizes selectively the human IgG1 or IgG4 section in the spacer region of the CAR construct. A co-staining for CD3/CD8/CD4 T cells was performed. For the results refer to FIG. 7.

II. Co-Cultures of CAR-Transduced Human T Cells with Different Target Cell Lines Show Specific T Cell Activation by Distinct BCMA$^+$ Multiple Myeloma (MM) and B-NHL Cell Lines The readout was release of IFN-gamma as effector cytokine from T cells.

Generate retrovirus-transduced human T cells, as detailed before; employ all BCMA CAR-receptor variants (IX-XVII), SP6-negative control CAR, CD19 CAR, UT=untransduced T cells. Use the following human cell lines as target cells in co-culture:

| Cell line | Origin | BCMA-positivity |
|---|---|---|
| NCI-H929 | multiple myeloma (MM) | yes |
| MM.1S | MM | yes |
| OPM-2 | MM | yes |
| RPMI 8226 | MM | yes |
| REH | B acute lymphoblastic leukemia (B-ALL) | no |
| REH-BCMA | REH stably transduced with BCMA | yes |
| DOHH-2 | immunoblastic B cell lymphoma progressed from follicular centroblastic/centrocytic lymphoma (FL) | yes, weakly |
| JVM-3 | B cell chronic lymphocytic leukemia (B-CLL) | yes, weakly |
| SU-DHL4 | diffuse large B cell lymphoma (DLBCL), germinal center type | yes, weakly |
| NALM-6 | B acute lymphoblastic leukemia (B-ALL) | no |
| RS4 | B-ALL | no |
| Jurkat | T cell acute lymphoblastic leukemia (T-ALL) | no |
| normal peripheral B cells | healthy donor | no |
| MEC-1 | B-CLL | yes, weakly |
| JEKO-1 | mantle cell lymphoma (MCL), B-NHL | yes, weakly |
| HUVEC | human umbilical vein endothelial cells, healthy donor | no |
| SW620 | colon carcinoma | no |
| HT116 | colon carcinoma | no |
| HEK293 | human embryonic kidney epithelial cells | no |
| PBMC | human peripheral blood mononuclear cells, healthy donor | no |

Figure 8:
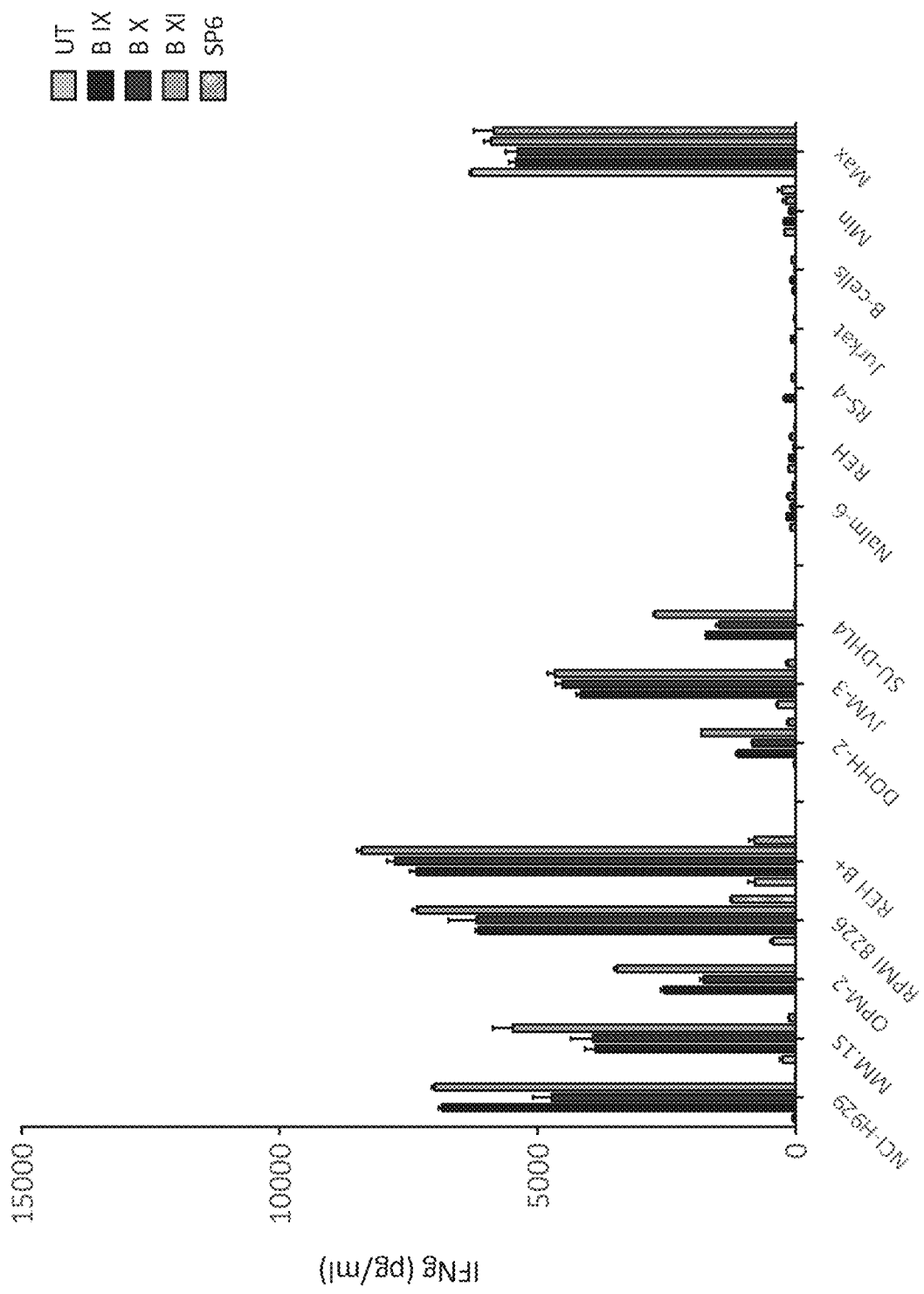
FIG. 8: Co-cultures of CAR-transduced human T cells with different target cell lines show specific T cell activation by distinct BCMA$^+$ multiple myeloma (MM) and B-NHL cell lines. Functional in vitro co-cultivation and IFN-gamma ELISA.

Co-culture retrovirally transduced T cells for 18-20 hrs in the presence of the listed cell lines or primary cells at a ratio 1:1. After that time, take cell-free culture supernatant; max. release is induced by PMA/ionomycin stimulation of effector T cells; minimum release is T cells only. Determine IFN-gamma release in the supernatant by ELISA. Refer to FIG. 8 for the results.

III. CD107a (LAMP1) Staining of Co-Cultured CAR-T Cells with Multiple Myeloma Cells: Detection of Activated Degranulating CD8$^+$ T Cells Upon Antigen-Specific (BCMA) Stimulation by Flow Cytometry Generate retrovirus-transduced human T cells, as detailed above; employ BCMA CAR-receptor variants (IX-XI), SP6-negative control CAR.

Co-culture retrovirally transduced T cells for 18 hrs in the presence of the listed cell lines at a ratio of 1:1.

Add for overnight culture anti CD107a (LAMP1) antibody into cell medium; antibody binds continuously on T cells when secretory lysosomes are fusing with the plasma membrane and release the enzymatic content of their vesicles. These vesicles contain cytolytic mediators such as granzymes and perforin. On the next day, T cells are co-stained with anti CD8 and/or CD3.

Figure 9:
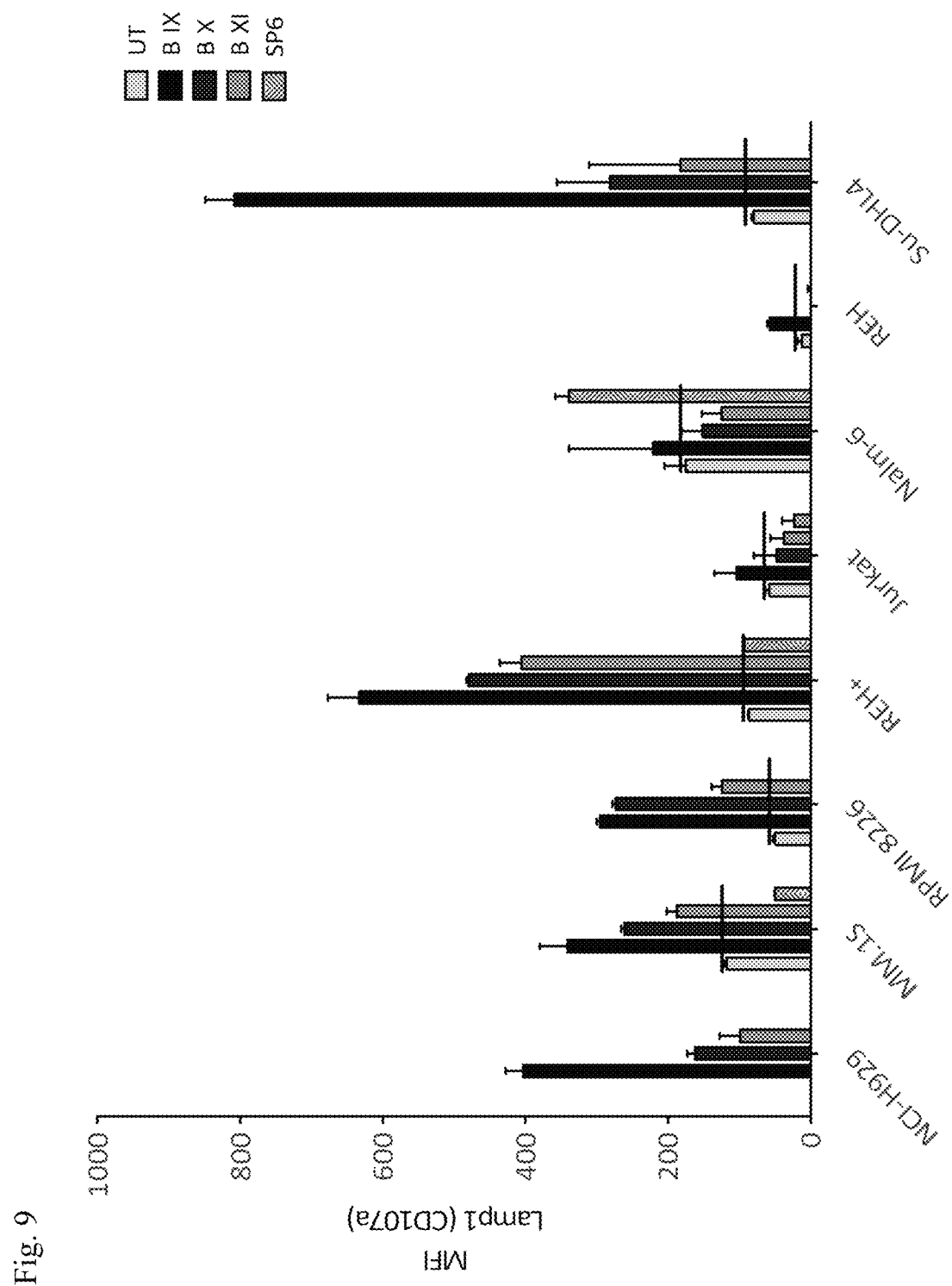
FIG. 9: CD107a (LAMP1) staining of co-cultured CAR-T cells with multiple myeloma cells: detection of activated degranulating CD8$^+$ T cells upon antigen-specific (BCMA) stimulation by flow cytometry. Functional in vitro co-cultivation and LAMP1 detection, as determined by FACS.

Analysis by flow cytometry: higher CD107a reactivity, expressed as mean fluorescence intensity (MFI), indicates stronger activation of T cells. The antigen-dependent activation of T cells can be confirmed. For results refer to FIG. 9.

IV. Cytotoxicity Assays Reveal Selective Killing of BCMA-Postive Cell Lines; Essentially No Killing was Seen in BCMA-Negative Cell Lines Use of $^{51}$Cr-release assay for quantitation of cytotoxic T lymphocyte activity. Measure target cell cytolysis.

Generate retrovirus-transduced human T cells, as detailed before; employ BCMA CAR-receptor variants (IX-XI), SP6-negative control CAR; CD19 CAR as control Label target cells with $^{51}$Cr. Co-culture then CAR-T cells and labeled target cells for 4 hrs. Titrate the effector to target ratio.

E:T
80:1
40:1
20:1
10:1
5:1
2.5:1

Figure 10:
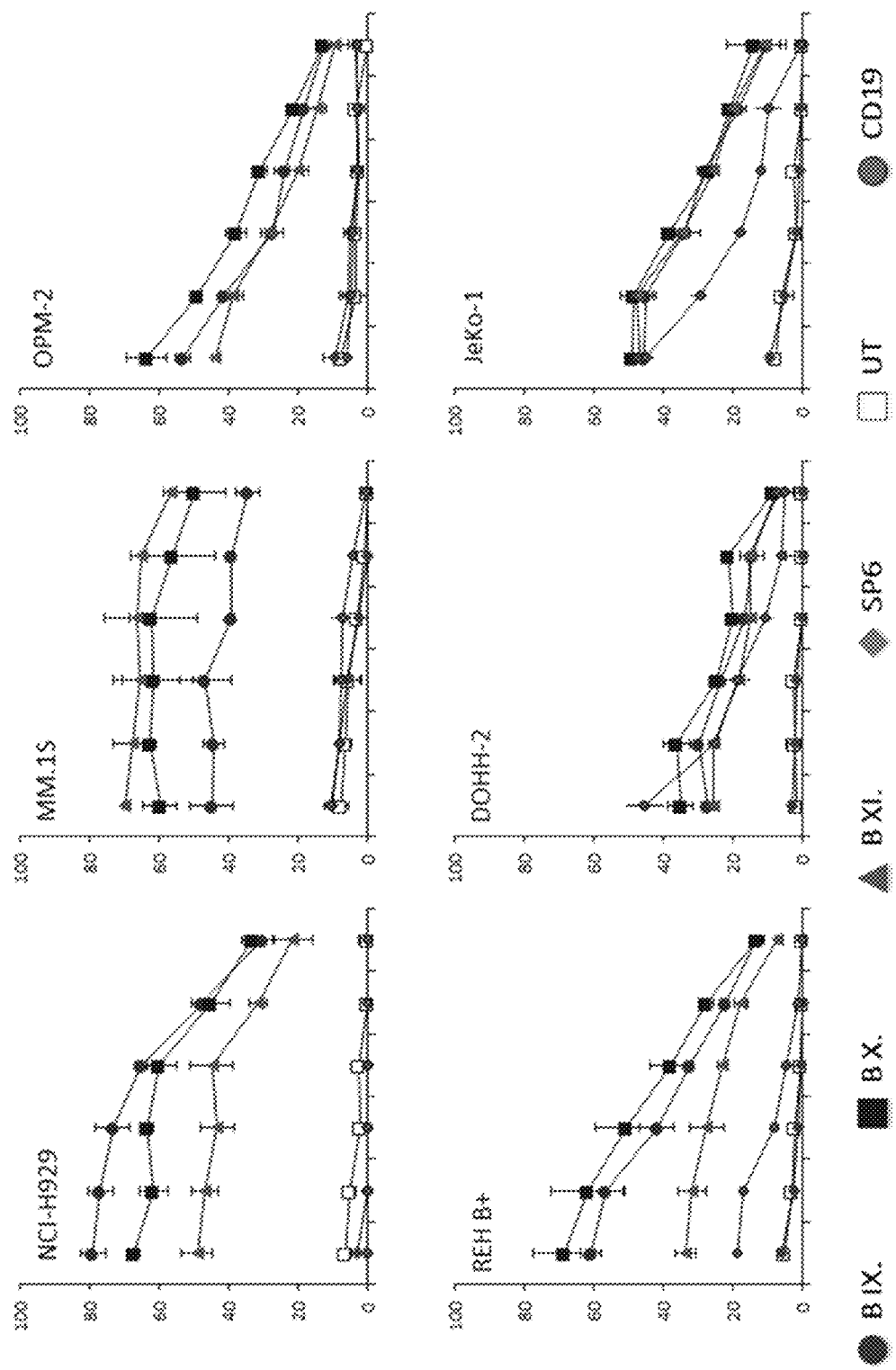
FIG. 10: Cytotoxicity assays reveal selective killing of BCMA-postive cell lines; essentially no killing was seen in BCMA-negative cell lines. Functional in vitro co-cultivation and 51Cr release assay.
Figure 10:
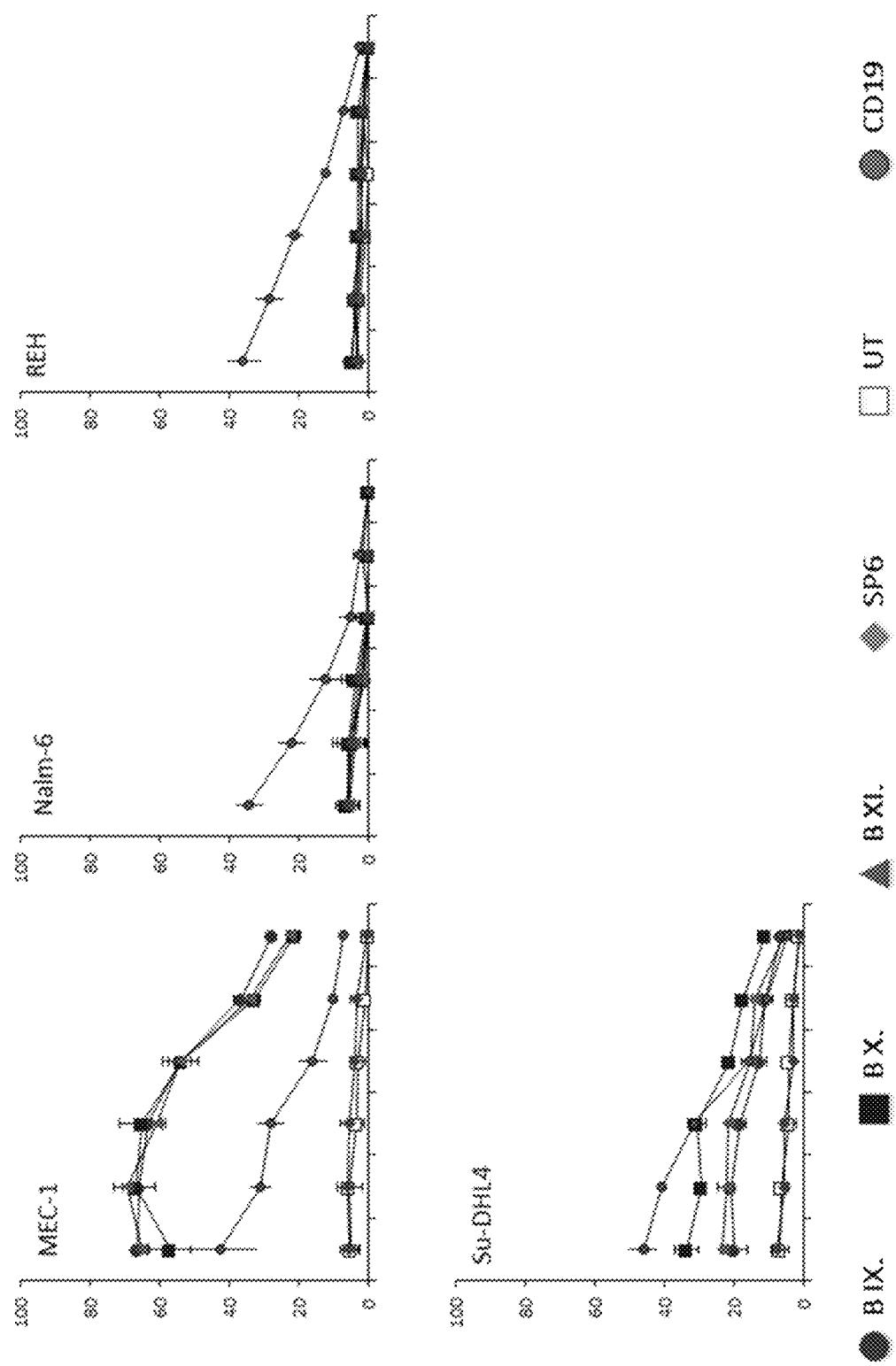

Harvest cell-free cell culture supernatant. Transfer supernatant to LUMA-scintillation plates, measure released $^{51}$Cr in a gamma-scintillation counter. Max. release: target cells lysed by Triton X-100 permeabilisation. Min. release: target cells alone. For the results, refer to FIG. 10.

Figure 11:
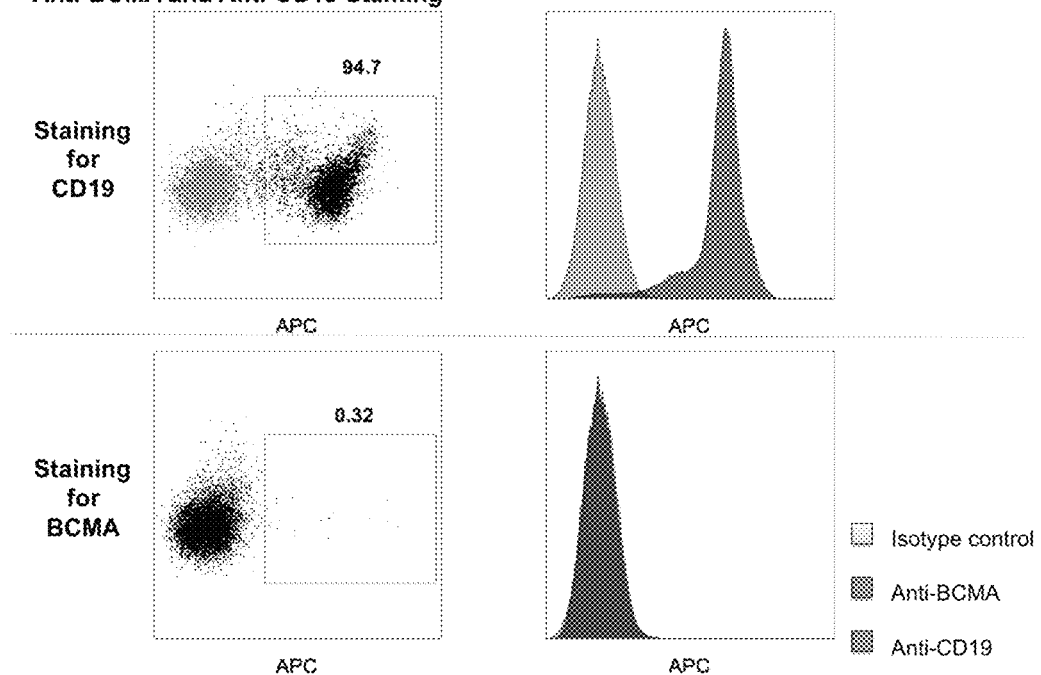
FIG. 11: BCMA and CD19 expression on the cell types assessed in the functional assays. Also shown are the results of MACS-based B-Cell isolation from PBMCs, together with anti-BCMA and anti-CD19 staining.
Figure 12:
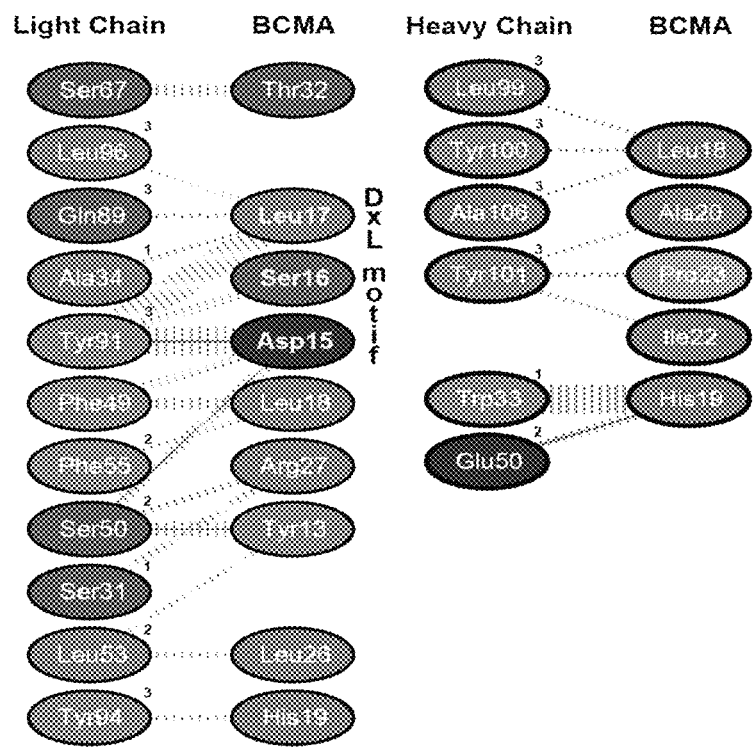
FIG. 12: Schematic representation of the binding interaction between the scFV of the CAR and the BCMA epitope.

Furthermore, FIG. 11 provides results showing the amount of BCMA and CD19 expressed on the surface of each of the cell types assessed for cytotoxicity. FIG. 12 provides a schematic representation of the interaction between the scFV binding region of the CAR and the BCMA epitope.

Example 4: In Vivo Experiments Using a Xenotransplantation NSG Mouse Model to Assess Adoptively Transferred CAR-T Cells Against B-NHL and Myeloma Cell Lines In Vivo Experiments Using Xenotransplantation into NSG Mice 1) To demonstrate that CAR T cells equipped with the diverse anti BCMA-variants have effector activity also under in situ conditions, multiple myeloma cells with different BCMA antigen densities are transplanted via an i.v. route into NSG-mice (NOD.Cg-Prkdc$^{scid}$ Il2rg$^{tm1\ Wjl}$/SzJ). The multiple myeloma cell lines that may be employed are: RPMI-8226, low BCMA; MM1S, intermediate BCMA density; NCI-H229, high BCMA density.

2) To confirm anti BCMA CAR T cell reactivity against B-NHL cell lines in situ, NSG mice are injected i.v. with luciferase-transduced cell lines, such as SU-DHL4 (DLBCL), JEKO-1 (mantle cell lymphoma), JVM3 (CLL), MEC1 (CLL), DOHH-2 (FL).

BCMA CAR-T Cells Mediate In Vivo Antitumor Activity in Mouse Models of Multiple Myeloma (MM) and B-Cell Non Hodgkin's Lymphoma (B-NHL):

To provide proof-of-concept that the strong in vitro activity of T cells modified with the BCMA CAR translates into efficient antitumor activity in vivo, we inoculated cohorts of NOD.Cg-Prkdc$^{scid}$ Il2rg$^{tm1\ Wjl}$/SzJ (NSG) mice i.v. with the human MM.1S cell line (FIG. 15) or the B-NHL cell line JeKo-1 (mantle cell lymphoma) (FIG. 16), transduced with the luciferase gene in tandem with GFP. NSG mice do not develop T, B, and NK cells and are therefore suitable for tolerance and growth of xenotransplantated human cells. Within the experimental time frame presented here, "graft-versus-host" (GvHD) reactions (xenoreactivity) was not observed (data not shown). Tumor growth was monitored by IVIS imaging and luciferin injection 7-8 days thereafter. Following tumor growth confirmation, CAR-T cells were i.v. injected one day later (=day 0). For functional in vivo experiments CAR construct IX (B IX) was used. Total numbers never exceeded $6-7\times10^6$/animal CAR-T cells, and the average transduction rate for T cells in this population was 40-60%. Per donor, SP6 and BCMA transduction rates were matched within a range of +/−10%. For the two experiments shown, an effective rate of $3\times10^6$ transduced CAR-T cells was used. Control mice received SP6 CAR-T cells.

Figure 15:
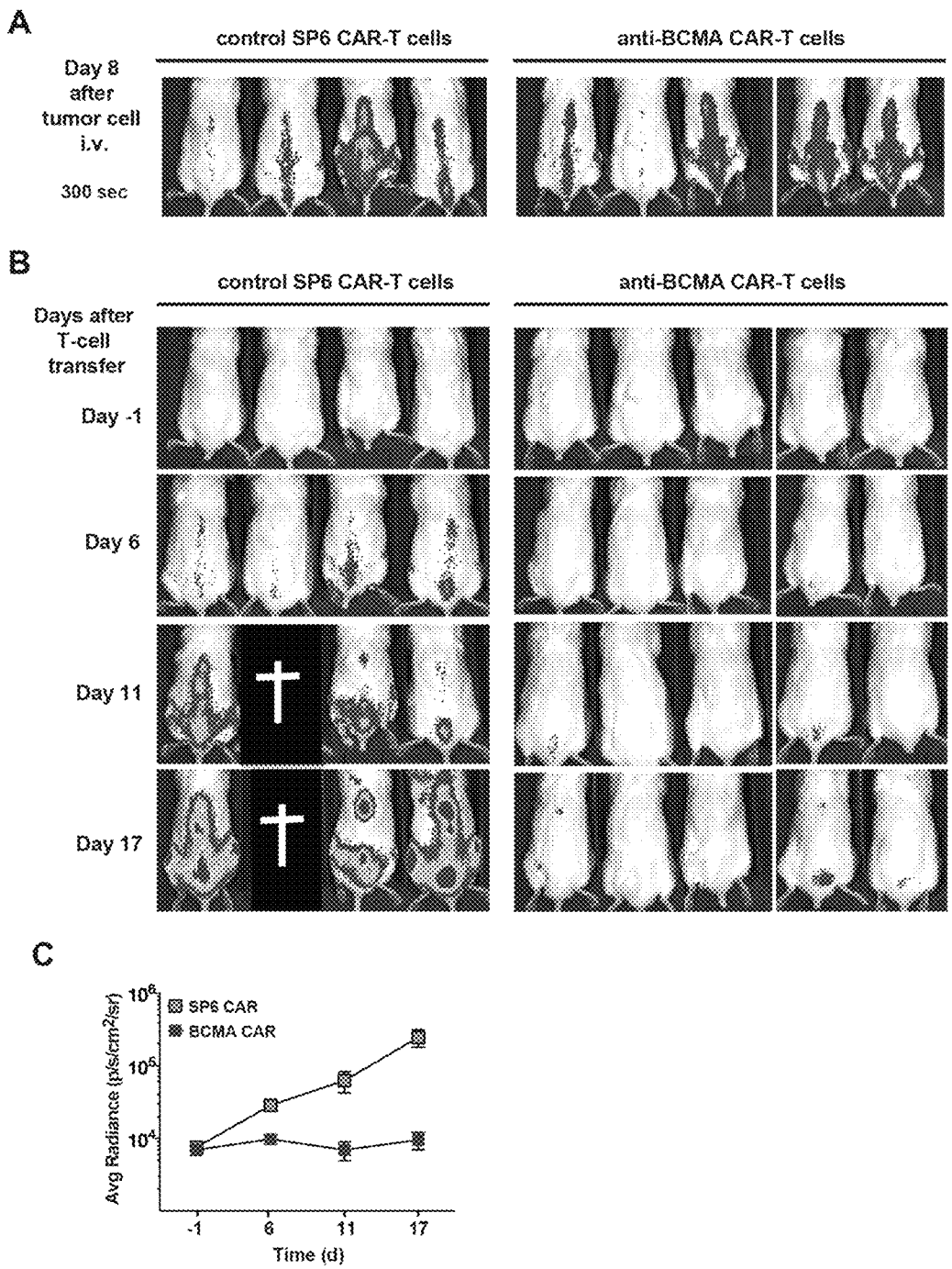
FIG. 15: BCMA redirected CAR-T cells are effective against MM tumors in a xenografted NSG mouse model. (A) Engraftment of MM tumors in a xenografted NSG mouse model. Mice were challenged by i.v. transplantation of MM.1S cells. At day 8 after tumor inoculation, tumor cell growth was visualized by IVIS imaging. To measure tumor burden, imaging was extended to 300 sec (day −1). (B) To follow treatment efficacy and to scale down bioluminescence intensity for better presentation, mice as in (A) were again imaged for 30 sec at day −1. Subsequent IVIS-exposures after CAR-T cell transfer, control SP6 CAR-T cells (n=4) and BCMA CAR-T cells (n=6), were done at 30 sec to allow better comparisons between day −1 and day 17 which has the highest intensity. White cross, animal was sacrificed because of advanced disease and animal protection laws. (C) Mean values of bioluminescence signal intensities obtained from regions of interests covering the entire body of each mouse are plotted for each group at each time point.

In the MM1.S experiment (FIG. 15), $3\times10^6$ transduced CAR-T cells (as above, total: $6-7\times10^6$) were transplanted and the observation interval was extended to 17 days. While essentially all SP6 CAR treated animals had progressive MM disease, characterized by strong luminescence signals over the spine, pelvis, and hind legs, or were sacrificed because of disease progression in accordance with (Berlin State) animal protection laws, this was clearly not the case for the BCMA CAR treatment group. We conclude that at this comparably low CAR-T cell number the BCMA CAR-T cells already have anti-myeloma activity (FIGS. 15A-C).

Due to the high affinity and avidity of the anti-BCMA CAR-T cell, even low BCMA-expressing mature B cell NHL can be recognized, allowing for T cell activation and tumor cell killing. Such mature B-NHL entities include certain stages of follicular lymphoma, diffuse large B-cell lymphoma, mantle cell lymphoma, and chronic lymphocytic leukemia (see FIGS. 11, 10, 9, 8). To prove the suitability of BCMA as a target structure in B-NHL entities, transduced CAR-T cells (total: $6-7\times10^6$) were transplanted in NSG mice which had been challenged with the mantle cell lymphoma cell line JeKo-1. While essentially all SP6 CAR treated animals had progressive lymphoma disease, characterized by strong luminescence signals over the liver, thoracical organs, bone marrow in hind limbs, and spleen, this was clearly not the case for the BCMA CAR treatment group. With this we provide the first pre-clinical in vivo proof that BCMA CAR-T cells have anti-tumor activity beyond multiple myeloma and extending to B-NHL lymphoma entities (FIGS. 16A-C).

Example 5: Determination of Surface Density of BCMA Molecules

The high affinity and avidity of the anti-BCMA CAR-T cells allow for the recognition of even low BCMA-expressing mature B cell NHL entities, resulting in T cell activation and tumor cell killing. Such mature B-NHL entities include certain stages of follicular lymphoma, diffuse large B-cell lymphoma, mantle cell lymphoma, and chronic lymphocytic leukemia.

To quantify the surface density of the BCMA molecules, we have applied the PE Phycoerythrin Fluorescence Detection Kit, also referred to as BD Quantibrite assay (BD Bioscience). The number of PE molecules per cell can be converted to antibodies per cell, which is a quantitative estimate of the number of antigens per cell. A flow cytometry detection method was applied.

Using this method, we find that the multiple myeloma cell line NCI-H929 has a relative surface BCMA antigen density of 12555, the multiple myeloma cell line OPM-2 has 3443 BCMA molecules, and the multiple myeloma cell line MM.1S has a relative value of 3181.

The BCMA antigen densities for the mentioned B-NHL cell lines, relative to NCI-H929, are: DOHH-2: 1/20, JeKo-1: 1/250, MEC-1: 1/34

What is claimed is:

1. A nucleic acid molecule encoding a chimeric antigen receptor (CAR) polypeptide, wherein the CAR polypeptide comprises:
   i. an extracellular antigen-binding domain, comprising an antibody or antibody fragment that binds a human B Cell Maturation Antigen (BCMA) polypeptide;
   ii. a transmembrane domain; and
   iii. an intracellular domain;
   wherein the extracellular antigen-binding domain comprises:
   (I) a variable heavy chain (VH) domain comprising:
      (a) a heavy chain complementarity determining region 1 (H-CDR1) comprising SEQ ID NO: 34 (RYWX$_1$S), wherein X$_1$ is I, F, L, V, Y, C, G, A, or M;
      (b) a heavy chain complementarity determining region 2 (H-CDR2) comprising amino acids 50-67 of SEQ ID NO: 53 (EINPZ$_2$SSTINYAPSLKX$_{11}$X$_{12}$), wherein Z$_2$ is S, N, T, G, or D; X$_{11}$ is D; and X$_{12}$ is K or R; and
      (c) a heavy chain complementarity determining region 3 (H-CDR3) comprising SEQ ID NO: 36 (SLYX$_4$DYGDAX$_5$DYW), wherein X$_4$ is Y, and X$_5$ is Y, L, F, I, V, A, C, or M; and
   (II) a variable light chain (VL) domain comprising:
      (a) a light chain complementarity determining region 1 (L-CDR1) comprising SEQ ID NO: 37 (KASQSVX$_1$X$_2$NVA), wherein X$_1$X$_2$ is ES or DS;
      (b) a light chain complementarity determining region 2 (L-CDR2) comprising SEQ ID NO: 29 (SASLRFS), and
      (c) a light chain complementarity determining region 3 (L-CDR3) comprising SEQ ID NO: 30 (QQYNNYPLTFG);
   wherein expression of the CAR polypeptide in an immune effector cell is effective to increase cytotoxicity of the immune effector cell to both (i) multiple myeloma cells, and (ii) mantle cell lymphoma cells.

2. A genetically modified immune cell comprising the nucleic acid molecule or vector according to claim 1.

3. The genetically modified immune cell according to claim 2, wherein the immune cell is selected from the group consisting of a T lymphocyte or an NK cell.

4. The genetically modified immune cell according to claim 3, wherein the T lymphocyte is a cytotoxic T lymphocyte.

5. The nucleic acid molecule according to claim 1, wherein the CAR polypeptide transduces an intracellular signal in an immune effector cell in response to binding human BCMA.

6. The nucleic acid molecule according to claim 5, wherein:
   A. the VH domain comprises:
      (i) H-CDR1 comprising SEQ ID NO: 34 (RYWX$_1$S), wherein X$_1$ is I, F, or M;
      (ii) H-CDR2 comprising amino acids 50-67 of SEQ ID NO: 53 (EINPZ$_2$SSTINYAPSLKX$_{11}$X$_{12}$), wherein Z$_2$ is S, N, or D; X$_{11}$ is D; and X$_{12}$ is K or R; and
      (iii) H-CDR3 comprising SEQ ID NO: 36 (SLYX$_4$DYGDAX$_5$DYW), wherein X$_4$ is Y, and X$_5$ is Y or M; and
   B. the VL domain comprises:
      (i) L-CDR1 comprising SEQ ID NO: 37 (KASQSVX$_1$X$_2$NVA), wherein X$_1$X$_2$ is ES or DS;
      (ii) L-CDR2 comprising SEQ ID NO: 29 (SASLRFS); and
      (iii) L-CDR3 comprising SEQ ID NO: 30 (QQYNNYPLTFG).

7. The nucleic acid molecule according to claim 6, wherein the CAR polypeptide comprises the following sequences:

```
                                    SEQ ID NO. 25
i.       H-CDR1: (RYWFS),

SEQ ID NO. 26
ii.      H-CDR2: (EINPSSSTINYAPSLKDK),

SEQ ID NO. 27
iii.     H-CDR3: (SLYYDYGDAYDYW),

SEQ ID NO. 28
iv.      L-CDR1: (KASQSVESNVA),
```

|  | SEQ ID NO. 29 |
|---|---|
| v. | L-CDR2: (SASLRFS), and |

|  | SEQ ID NO. 30 |
|---|---|
| vi. | L-CDR3: (QQYNNYPLTFG). |

8. The nucleic acid molecule according to claim 1, wherein the CAR polypeptide comprises a VH domain with at least 80% sequence identity to SEQ ID NO: 11; and a VL domain with at least 80% sequence identity to SEQ ID NO: 12.

9. The nucleic acid according to claim 8, wherein the VH domain comprises at least W36, E50, L99, Y100, Y101 and A106 of SEQ ID NO: 11, and the VL domain comprises at least S31, A34, S50, L53, Q89, Y91, Y94 and L96 of SEQ ID NO: 12.

10. The nucleic acid molecule according to claim 8, wherein the VH domain comprises at least the CDR sequences of SEQ ID NOs: 25 to 27, and the VL domain comprises at least the CDR sequences of SEQ ID NOs: 28 to 30.

11. The nucleic acid molecule according to claim 8, wherein the CAR polypeptide comprises the VH and VL domains according to SEQ ID NO: 11 and SEQ ID NO: 12, respectively.

12. The nucleic acid molecule according to claim 1, wherein when the CAR polypeptide is expressed in a genetically modified immune cell, said immune cell binds human BCMA on the surface of a B-cell non-Hodgkin's lymphoma (B-NHL) via said CAR and is activated, thereby inducing cytotoxic activity against said B-NHL.

13. The nucleic acid molecule according to claim 12, wherein the B-NHL is JeKo-1, DOHH-2, SU-DHL4, JVM-3 and/or MEC-1 cell lines.

14. The nucleic acid molecule according to claim 1, wherein the extracellular antigen-binding domain further comprises a linker polypeptide positioned between the VH and VL domains.

15. The nucleic acid molecule according to claim 14, wherein said linker is selected from a Whitlow (SEQ ID NO: 13; GSTSGSGKPGSGEGSTKG) or Gly-Ser (SEQ ID NO: 14; SSGGGGSGGGGSGGGGS) linker, or linkers with at least 80% sequence identity to SEQ ID NO: 13 or 14.

16. The nucleic acid molecule according to claim 1, wherein the CAR polypeptide further comprises a spacer polypeptide positioned between the extracellular antigen-binding domain and the transmembrane domain, wherein said spacer is selected from the group consisting of:

IgG1Δ -CD28 spacer (SEQ ID NO 15;
PAEPKSPDKTHTCPPCPAPPVAGPSVFLFPPKPKDTLMIARTPEVTCVVV

DVSHEDPEVKFNWYVDGVEVHNAKTKPREEQYNSTYRVVSVLTVLHQDWL

NGKEYKCKVSNKALPAPIEKTISKAKGQPREPQVYTLPPSRDELTKNQVS

LTCLVKGFYPSDIAVEWESNGQPENNYKTTPPVLDSDGSFFLYSKLTVDK

SRWQQGNVFSCSVMHEALHNHYTQKSLSLSPGKK),

IgG1Δ - 4-1BB spacer (SEQ ID NO 16;
PAEPKSPDKTHTCPPCPAPPVAGPSVFLFPPKPKDTLMIARTPEVTCVVV

DVSHEDPEVKFNWYVDGVEVHNAKTKPREEQYNSTYRVVSVLTVLHQDWL

NGKEYKCKVSNKALPAPIEKTISKAKGQPREPQVYTLPPSRDELTKNQVS

LTCLVKGFYPSDIAVEWESNGQPENNYKTTPPVLDSDGSFFLYSKLTVDK

SRWQQGNVFSCSVMHEALHNHYTQKSLSLSPGKK),

IgG4 (Hi-CH2—CH3) spacer (SEQ ID NO 17;
ESKYGPPCPPCPAPEFEGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCL

VKGFYPSDIAVEWESNGQPENNYKTTPPVLDSDGSFFLYSRLTVDKSRWQ

EGNVFSCSVMHEALHNHYTQKSLSLSLGK),

IgG4 (Hi-CH3) spacer (SEQ ID NO 18;
ESKYGPPCPPCPGQPREPQVYTLPPSQEEMTKNQVSLTCLVKGFYPSDIA

VEWESNGQPENNYKTTPPVLDSDGSFFLYSRLTVDKSRWQEGNVFSCSVM

HEALHNHYTQKSLSLSLGK),

IgG4 (Hi) spacer (SEQ ID NO 19;
ESKYGPPCPPCP), and
a spacer with at least 80% sequence identity to any one of SEQ ID NOs: 15 to 19.

17. The nucleic acid molecule according to claim 1, wherein the transmembrane domain is selected from the group consisting of a CD8α transmembrane domain, a CD28 transmembrane domain, and a transmembrane domain with at least 80% sequence identity to SEQ ID NO: 20 or 21.

18. The nucleic acid molecule according to claim 1, wherein the intracellular domain comprises a co-stimulatory domain selected from the group consisting of a 4-1BB co-stimulatory domain, a CD28 co-stimulatory domain, and a co-stimulatory domain with at least 80% sequence identity to SEQ ID NO: 22 or 23.

19. The nucleic acid molecule according to claim 1, wherein the CAR polypeptide further comprises a signaling domain, wherein said signaling domain comprises a CD3 zeta signaling domain, or a signaling domain with at least 80% sequence identity to SEQ ID NO: 24.

20. The nucleic acid molecule according to claim 1, wherein the intracellular domain comprises a CD28 co-stimulatory domain.

\* \* \* \* \*

UNITED STATES PATENT AND TRADEMARK OFFICE
CERTIFICATE OF CORRECTION

PATENT NO. : 12,351,640 B2
APPLICATION NO. : 18/667995
DATED : July 8, 2025
INVENTOR(S) : Rehm et al.

It is certified that error appears in the above-identified patent and that said Letters Patent is hereby corrected as shown below:

In the Specification

Column 1, Line 24, delete "1.52 (e). The" and insert -- 1.52(e). The --.

Column 2, Line 4, delete "5/100,000," and insert -- 5/100.000, --.

Column 2, Line 21, delete "10-12/100,000" and insert -- 10-12/100.000 --.

Column 3, Line 46, delete "Res; 19 (8); 2048" and insert -- Res; 19(8); 2048 --.

Column 5, Line 32, delete "Becton Dickenson). The" and insert -- Becton Dickinson). The --.

Column 17, Line 36-37 (approx.), delete "SVGDX-VX$_8$X$_g$TCK" and insert -- SVGDX$_7$VX$_8$X$_9$TCK --.

Column 21-22, Line 48 (approx.), delete "V, Y. C," and insert -- V, Y, C, --.

Column 23-24, Line 21 (approx.), delete "V, Y. C," and insert -- V, Y, C, --.

Column 25-26, Line 30 (approx.), delete "V, Y. C," and insert -- V, Y, C, --.

Column 41, Line 6, delete "failure, exceessive antibody" and insert -- failure, excessive antibody --.

Column 47, Line 6, delete "international ImMunoGene Tics information" and insert -- international ImMunoGeneTics information --.

Column 48, Line 28-29, delete "receptor, CD38, CD3Z, CD4," and insert -- receptor, CD3ε, CD3ζ, CD4, --.

Column 50, Line 35, delete "virus (MOMSV), Harvey" and insert -- virus (MoMSV), Harvey --.

Signed and Sealed this
Twenty-third Day of September, 2025

John A. Squires
*Director of the United States Patent and Trademark Office*

CERTIFICATE OF CORRECTION (continued)
U.S. Pat. No. 12,351,640 B2

Column 52, Line 48, delete "Val, IIe and" and insert -- Val, Ile and --.

Column 57, Line 17 (approx.), delete "The tem prophylactic" and insert -- The term prophylactic --.

Column 59, Line 15, delete "Idiopathic thrombocytopenia purpura" and insert -- Idiopathic thrombocytopenic purpura --.

Column 60, Line 37 (approx.), delete "Graves disase, Autoimmune" and insert -- Graves disease, Autoimmune --.

Column 62, Line 25, delete "BCMA-postive cell" and insert -- BCMA-positive cell --.

Column 64, Line 5, delete "antihuCD3 und anti" and insert -- antihuCD3 and anti --.

Column 64, Line 41, delete "IL7 und 10" and insert -- IL7 and 10 --.

Column 66, Line 10, delete "BCMA-Postive Cell" and insert -- BCMA-Positive Cell --.

In the Claims

Column 107, Claim 2, Line 64, delete "molecule or vector according to" and insert -- molecule according to --.

Column 109, Claim 16, Line 51 (approx.), delete "ID NO 15;" and insert -- ID NO: 15; --.

Column 110, Claim 16, Line 7 (approx.), delete "ID NO 16;" and insert -- ID NO: 16; --.

Column 110, Claim 16, Line 15 (approx.), delete "ID NO 17;" and insert -- ID NO: 17; --.

Column 110, Claim 16, Line 24 (approx.), delete "ID NO 18;" and insert -- ID NO: 18; --.

Column 110, Claim 16, Line 30 (approx.), delete "ID NO 19;" and insert -- ID NO: 19; --.

SEQUENCE LISTING

```
Sequence total quantity: 94
SEQ ID NO: 1            moltype = AA  length = 8
FEATURE                 Location/Qualifiers
REGION                  1..8
                        note = CDR
source                  1..8
                        mol_type = protein
                        organism = synthetic construct
SEQUENCE: 1
GFTFSRYW                                                               8

SEQ ID NO: 2            moltype = AA  length = 8
FEATURE                 Location/Qualifiers
REGION                  1..8
                        note = CDR
source                  1..8
                        mol_type = protein
                        organism = synthetic construct
SEQUENCE: 2
INPSSSTI                                                               8

SEQ ID NO: 3            moltype = AA  length = 13
FEATURE                 Location/Qualifiers
REGION                  1..13
                        note = CDR
source                  1..13
                        mol_type = protein
                        organism = synthetic construct
SEQUENCE: 3
ASLYYDYGDA YDY                                                        13
```

```
SEQ ID NO: 4              moltype = AA  length = 6
FEATURE                   Location/Qualifiers
REGION                    1..6
                          note = CDR
source                    1..6
                          mol_type = protein
                          organism = synthetic construct
SEQUENCE: 4
QSVESN                                                                    6

SEQ ID NO: 5              moltype =   length =
SEQUENCE: 5
000

SEQ ID NO: 6              moltype = AA  length = 9
FEATURE                   Location/Qualifiers
REGION                    1..9
                          note = CDR
source                    1..9
                          mol_type = protein
                          organism = synthetic construct
SEQUENCE: 6
QQYNNYPLT                                                                 9

SEQ ID NO: 7              moltype = AA  length = 8
FEATURE                   Location/Qualifiers
source                    1..8
                          mol_type = protein
                          organism = synthetic construct
VARIANT                   4..5
                          note = XX is ser-ser, asn-ser, thr-ser, gly-ser, lys-ser,
                           arg-ser, ser-asp, ser-asn, asp-glu
SEQUENCE: 7
INPXXSTI                                                                  8

SEQ ID NO: 8              moltype = AA  length = 13
FEATURE                   Location/Qualifiers
source                    1..13
                          mol_type = protein
                          organism = synthetic construct
VARIANT                   5
                          note = X is tyr, leu, ala, val, phe, ile or trp
VARIANT                   11
                          note = X is tyr, leu, phe, ile, val, ala or cys
SEQUENCE: 8
ASLYXDYGDA XDY                                                            13

SEQ ID NO: 9              moltype = AA  length = 6
FEATURE                   Location/Qualifiers
source                    1..6
                          mol_type = protein
                          organism = synthetic construct
VARIANT                   4..5
                          note = XX is glu-ser, ser-ser, thr-ser, gln-ser, his-ser,
                           asp-his
SEQUENCE: 9
QSVXXN                                                                    6

SEQ ID NO: 10             moltype = AA  length = 11
FEATURE                   Location/Qualifiers
REGION                    1..11
                          note = CDR
source                    1..11
                          mol_type = protein
                          organism = synthetic construct
SEQUENCE: 10
QQYNNYPLTF G                                                              11

SEQ ID NO: 11             moltype = AA  length = 120
FEATURE                   Location/Qualifiers
REGION                    1..120
                          note = VH
source                    1..120
                          mol_type = protein
                          organism = synthetic construct
SEQUENCE: 11
EVQLVESGGG LVQPGGSLRL SCAASGFTFS RYWFSWVRQA PGKGLVWVGE INPSSSTINY          60
APSLKDKFTI SRDNAKNTLY LQMNSLRAED TAVYYCASLY YDYGDAYDYW GQGTLVTVSS         120
```

```
SEQ ID NO: 12            moltype = AA   length = 107
FEATURE                  Location/Qualifiers
REGION                   1..107
                         note = VL
source                   1..107
                         mol_type = protein
                         organism = synthetic construct
SEQUENCE: 12
EIVMTQSPAT LSVSPGERAT LSCKASQSVE SNVAWYQQKP GQAPRALIYS ASLRFSGIPA    60
RFSGSGSGTE FTLTISSLQS EDFAVYYCQQ YNNYPLTFGA GTKLELK                  107

SEQ ID NO: 13            moltype = AA   length = 18
FEATURE                  Location/Qualifiers
REGION                   1..18
                         note = linker
source                   1..18
                         mol_type = protein
                         organism = synthetic construct
SEQUENCE: 13
GSTSGSGKPG SGEGSTKG                                                  18

SEQ ID NO: 14            moltype = AA   length = 17
FEATURE                  Location/Qualifiers
REGION                   1..17
                         note = linker
source                   1..17
                         mol_type = protein
                         organism = synthetic construct
SEQUENCE: 14
SSGGGGSGGG GSGGGGS                                                   17

SEQ ID NO: 15            moltype = AA   length = 234
FEATURE                  Location/Qualifiers
REGION                   1..234
                         note = spacer
source                   1..234
                         mol_type = protein
                         organism = synthetic construct
SEQUENCE: 15
PAEPKSPDKT HTCPPCPAPP VAGPSVFLFP PKPKDTLMIA RTPEVTCVVV DVSHEDPEVK    60
FNWYVDGVEV HNAKTKPREE QYNSTYRVVS VLTVLHQDWL NGKEYKCKVS NKALPAPIEK    120
TISKAKGQPR EPQVYTLPPS RDELTKNQVS LTCLVKGFYP SDIAVEWESN GQPENNYKTT    180
PPVLDSDGSF FLYSKLTVDK SRWQQGNVFS CSVMHEALHN HYTQKSLSLS PGKK          234

SEQ ID NO: 16            moltype = AA   length = 235
FEATURE                  Location/Qualifiers
REGION                   1..235
                         note = spacer
source                   1..235
                         mol_type = protein
                         organism = synthetic construct
SEQUENCE: 16
PAEPKSPDKT HTCPPCPAPP VAGPSVFLFP PKPKDTLMIA RTPEVTCVVV DVSHEDPEVK    60
FNWYVDGVEV HNAKTKPREE QYNSTYRVVS VLTVLHQDWL NGKEYKCKVS NKALPAPIEK    120
TISKAKGQPR EPQVYTLPPS RDELTKNQVS LTCLVKGFYP SDIAVEWESN GQPENNYKTT    180
PPVLDSDGSF FLYSKLTVDK SRWQQGNVFS CSVMHEALHN HYTQKSLSSL SPGKK         235

SEQ ID NO: 17            moltype = AA   length = 229
FEATURE                  Location/Qualifiers
REGION                   1..229
                         note = spacer
source                   1..229
                         mol_type = protein
                         organism = synthetic construct
SEQUENCE: 17
ESKYGPPCPP CPAPEFEGGP SVFLFPPKPK DTLMISRTPE VTCVVVDVSQ EDPEVQFNWY    60
VDGVEVHNAK TKPREEQFNS TYRVVSVLTV LHQDWLNGKE YKCKVSNKGL PSSIEKTISK    120
AKGQPREPQV YTLPPSQEEM TKNQVSLTCL VKGFYPSDIA VEWESNGQPE NNYKTTPPVL    180
DSDGSFFLYS RLTVDKSRWQ EGNVFSCSVM HEALHNHYTQ KSLSLSLGK                229

SEQ ID NO: 18            moltype = AA   length = 119
FEATURE                  Location/Qualifiers
REGION                   1..119
                         note = spacer
source                   1..119
                         mol_type = protein
                         organism = synthetic construct
SEQUENCE: 18
ESKYGPPCPP CPGQPREPQV YTLPPSQEEM TKNQVSLTCL VKGFYPSDIA VEWESNGQPE    60
```

-continued

```
NNYKTTPPVL DSDGSFFLYS RLTVDKSRWQ EGNVFSCSVM HEALHNHYTQ KSLSLSLGK      119

SEQ ID NO: 19           moltype = AA   length = 12
FEATURE                 Location/Qualifiers
REGION                  1..12
                        note = spacer
source                  1..12
                        mol_type = protein
                        organism = synthetic construct
SEQUENCE: 19
ESKYGPPCPP CP                                                          12

SEQ ID NO: 20           moltype = AA   length = 24
FEATURE                 Location/Qualifiers
REGION                  1..24
                        note = transmembrane
source                  1..24
                        mol_type = protein
                        organism = synthetic construct
SEQUENCE: 20
IYIWAPLAGT CGVLLLSLVI TLYC                                             24

SEQ ID NO: 21           moltype = AA   length = 27
FEATURE                 Location/Qualifiers
REGION                  1..27
                        note = transmembrane
source                  1..27
                        mol_type = protein
                        organism = synthetic construct
SEQUENCE: 21
FWVLVVVGGV LACYSLLVTV AFIIFWV                                          27

SEQ ID NO: 22           moltype = AA   length = 42
FEATURE                 Location/Qualifiers
REGION                  1..42
                        note = intracellular
source                  1..42
                        mol_type = protein
                        organism = synthetic construct
SEQUENCE: 22
KRGRKKLLYI FKQPFMRPVQ TTQEEDGCSC RFPEEEEGGC EL                         42

SEQ ID NO: 23           moltype = AA   length = 41
FEATURE                 Location/Qualifiers
REGION                  1..41
                        note = intracellular
source                  1..41
                        mol_type = protein
                        organism = synthetic construct
SEQUENCE: 23
RSKRSRLLHS DYMNMTPRRP GPTRKHYQPY APPRDFAAYR S                          41

SEQ ID NO: 24           moltype = AA   length = 113
FEATURE                 Location/Qualifiers
REGION                  1..113
                        note = intracellular
source                  1..113
                        mol_type = protein
                        organism = synthetic construct
SEQUENCE: 24
LRVKFSRSAD APAYQQGQNQ LYNELNLGRR EEYDVLDKRR GRDPEMGGKP RRKNPQEGLY      60
NELQKDKMAE AYSEIGMKGE RRRGKGHDGL YQGLSTATKD TYDALHMQAL PPR            113

SEQ ID NO: 25           moltype = AA   length = 5
FEATURE                 Location/Qualifiers
REGION                  1..5
                        note = CDR
source                  1..5
                        mol_type = protein
                        organism = synthetic construct
SEQUENCE: 25
RYWFS                                                                   5

SEQ ID NO: 26           moltype = AA   length = 18
FEATURE                 Location/Qualifiers
REGION                  1..18
                        note = CDR
source                  1..18
                        mol_type = protein
```

-continued

```
                           organism = synthetic construct
SEQUENCE: 26
EINPSSSTIN YAPSLKDK                                                 18

SEQ ID NO: 27              moltype = AA   length = 13
FEATURE                    Location/Qualifiers
REGION                     1..13
                           note = CDR
source                     1..13
                           mol_type = protein
                           organism = synthetic construct
SEQUENCE: 27
SLYYDYGDAY DYW                                                      13

SEQ ID NO: 28              moltype = AA   length = 11
FEATURE                    Location/Qualifiers
REGION                     1..11
                           note = CDR
source                     1..11
                           mol_type = protein
                           organism = synthetic construct
SEQUENCE: 28
KASQSVESNV A                                                        11

SEQ ID NO: 29              moltype = AA   length = 7
FEATURE                    Location/Qualifiers
REGION                     1..7
                           note = CDR
source                     1..7
                           mol_type = protein
                           organism = synthetic construct
SEQUENCE: 29
SASLRFS                                                             7

SEQ ID NO: 30              moltype = AA   length = 11
FEATURE                    Location/Qualifiers
REGION                     1..11
                           note = CDR
source                     1..11
                           mol_type = protein
                           organism = synthetic construct
SEQUENCE: 30
QQYNNYPLTF G                                                        11

SEQ ID NO: 31              moltype = AA   length = 53
FEATURE                    Location/Qualifiers
source                     1..53
                           mol_type = protein
                           organism = Homo sapiens
SEQUENCE: 31
MAGQCSQNEY FDSLLHACIP CQLRCSSNTP PLTCQRYCNA SVTNSVKGTN ALE           53

SEQ ID NO: 32              moltype = AA   length = 56
FEATURE                    Location/Qualifiers
source                     1..56
                           mol_type = protein
                           organism = Homo sapiens
SEQUENCE: 32
MLQMAGQCSQ NEYFDSLLHA CIPCQLRCSS NTPPLTCQRY CNASVTNSVK GTNALE        56

SEQ ID NO: 33              moltype = AA   length = 20
FEATURE                    Location/Qualifiers
source                     1..20
                           mol_type = protein
                           organism = Homo sapiens
SEQUENCE: 33
YFDSLLHACI PCQLRCSSNT                                               20

SEQ ID NO: 34              moltype = AA   length = 5
FEATURE                    Location/Qualifiers
source                     1..5
                           mol_type = protein
                           organism = synthetic construct
VARIANT                    4
                           note = X is ile, phe, leu, val, tyr, cys, gly, ala, ser or
                            Thr
SEQUENCE: 34
RYWXS                                                               5
```

```
SEQ ID NO: 35              moltype = AA  length = 18
FEATURE                    Location/Qualifiers
source                     1..18
                           mol_type = protein
                           organism = synthetic construct
VARIANT                    5..6
                           note = XX is ser-ser, asn-ser, thr-ser, gly-ser, lys-ser,
                            arg-ser, ser-asp, ser-asn, or asp-glu
SEQUENCE: 35
EINPXXSTIN YAPSLKDK                                                        18

SEQ ID NO: 36              moltype = AA  length = 13
FEATURE                    Location/Qualifiers
source                     1..13
                           mol_type = protein
                           organism = synthetic construct
VARIANT                    4
                           note = X is tyr, leu, ala, val phe, ile or trp
VARIANT                    10
                           note = X is tyr, leu, phe, ile, val, ala or cys
SEQUENCE: 36
SLYXDYGDAX DYW                                                             13

SEQ ID NO: 37              moltype = AA  length = 11
FEATURE                    Location/Qualifiers
source                     1..11
                           mol_type = protein
                           organism = synthetic construct
VARIANT                    7..8
                           note = XX is glu-ser, ser-ser, thr-ser, gln-ser, his-ser or
                            asp-his
SEQUENCE: 37
KASQSVXXNV A                                                               11

SEQ ID NO: 38              moltype = AA  length = 120
FEATURE                    Location/Qualifiers
REGION                     1..120
                           note = mouse Ab
source                     1..120
                           mol_type = protein
                           organism = synthetic construct
SEQUENCE: 38
QVQLQQSGGG LVQPGGSLKL SCAASGIDFS RYWMSWVRRA PGKGLEWIGE INPDSSTINY           60
APSLKDKFII SRDNAKNTLY LQMSKVRSED TALYYCASLY YDYGDAMDYW GQGTSVTVSS          120

SEQ ID NO: 39              moltype = AA  length = 120
FEATURE                    Location/Qualifiers
REGION                     1..120
                           note = Ab
source                     1..120
                           mol_type = protein
                           organism = synthetic construct
SEQUENCE: 39
EVQLVESGGG LVQPGGSLRL SCAASGFTFD DYWMSWVRQA PGKGLEWVGE INPDSSTINY           60
APSLKGRFTI SRDNAKNTLY LQMNSLRAED TAVYYCASLY YDYGDAMDYW GQGTLVTVSS          120

SEQ ID NO: 40              moltype = AA  length = 120
FEATURE                    Location/Qualifiers
REGION                     1..120
                           note = VH
source                     1..120
                           mol_type = protein
                           organism = synthetic construct
SEQUENCE: 40
EVQLVESGGG LVQPGGSLRL SCAASGFTFS RYWMSWVRQA PGKGLVWVGE INPDSSTINY           60
APSLKDKFTI SRDNAKNTLY LQMNSLRAED TAVYYCASLY YDYGDAMDYW GQGTLVTVSS          120

SEQ ID NO: 41              moltype = AA  length = 120
FEATURE                    Location/Qualifiers
source                     1..120
                           mol_type = protein
                           organism = synthetic construct
VARIANT                    34
                           note = X is Ile, phe, leu, val, tyr, cys, gly, ala, ser or
                            thr
VARIANT                    54..55
                           note = XX is ser-ser, asn-ser, thr-ser, gly-ser, lys-ser,
                            arg-ser, ser-asp, ser-asn, asp-glu
VARIANT                    101
```

```
                        note = X is tyr, leu, ala, val, phe, ile or trp
VARIANT                 107
                        note = X is tyr, leu, phe, ile, val, ala or cys
SEQUENCE: 41
EVQLVESGGG LVQPGGSLRL SCAASGFTFS RYWXSWVRQA PGKGLVWVGE INPXXSTINY   60
APSLKDKFTI SRDNAKNTLY LQMNSLRAED TAVYYCASLY XDYGDAXDYW GQGTLVTVSS  120

SEQ ID NO: 42           moltype = AA  length = 120
FEATURE                 Location/Qualifiers
source                  1..120
                        mol_type = protein
                        organism = synthetic construct
VARIANT                 33
                        note = X is trp, phe or tyr
VARIANT                 35
                        note = X is ser, thr, asn, gln, asp or glu
VARIANT                 47
                        note = X is trp, phe or tyr
VARIANT                 50
                        note = X is glu or gln
VARIANT                 99
                        note = X is leu, ile, val, gly or ala
VARIANT                 100
                        note = X is any amino acid, preferably tyr
VARIANT                 101
                        note = X is tyr, phe, leu, ile, val or met
VARIANT                 106
                        note = X is ala, gly or val
SEQUENCE: 42
EVQLVESGGG LVQPGGSLRL SCAASGFTFS RYXMXWVRQA PGKGLVXVGX INPDSSTINY   60
APSLKDKFTI SRDNAKNTLY LQMNSLRAED TAVYYCASXX XDYGDXMDYW GQGTLVTVSS  120

SEQ ID NO: 43           moltype = AA  length = 120
FEATURE                 Location/Qualifiers
REGION                  1..120
                        note = VH
source                  1..120
                        mol_type = protein
                        organism = synthetic construct
SEQUENCE: 43
EVQLVESGGG LVQPGGSLRL SCAASGFTFS RYWISWVRQA PGKGLVWVGE INPNSSTINY   60
APSLKDKFTI SRDNAKNTLY LQMNSLRAED TAVYYCASLY YDYGDAYDYW GQGTLVTVSS  120

SEQ ID NO: 44           moltype = AA  length = 120
FEATURE                 Location/Qualifiers
REGION                  1..120
                        note = VH
source                  1..120
                        mol_type = protein
                        organism = synthetic construct
SEQUENCE: 44
EVQLVESGGG LVQPGGSLRL SCAASGFTFS RYWFSWVRQA PGKGLVWVGE INPNSSTINY   60
APSLKDKFTI SRDNAKNTLY LQMNSLRAED TAVYYCASLY YDYGDAYDYW GQGTLVTVSS  120

SEQ ID NO: 45           moltype = AA  length = 120
FEATURE                 Location/Qualifiers
REGION                  1..120
                        note = VH
source                  1..120
                        mol_type = protein
                        organism = synthetic construct
SEQUENCE: 45
EVQLVESGGG LVQPGGSLRL SCAASGFTFS RYWISWVRQA PGKGLVWVGE INPSSSTINY   60
APSLKDKFTI SRDNAKNTLY LQMNSLRAED TAVYYCASLY YDYGDAYDYW GQGTLVTVSS  120

SEQ ID NO: 46           moltype = AA  length = 120
FEATURE                 Location/Qualifiers
REGION                  1..120
                        note = VH
source                  1..120
                        mol_type = protein
                        organism = synthetic construct
SEQUENCE: 46
EVQLVESGGG LVQPGGSLRL SCAASGFTFS RYWFSWVRQA PGKGLVWVGE INPSSSTINY   60
APSLKDKFTI SRDNAKNTLY LQMNSLRAED TAVYYCASLY YDYGDAYDYW GQGTLVTVSS  120

SEQ ID NO: 47           moltype = AA  length = 108
FEATURE                 Location/Qualifiers
REGION                  1..108
```

```
                        note = VL
source                  1..108
                        mol_type = protein
                        organism = synthetic construct
SEQUENCE: 47
DIVMTQSQRF MTTSVGDRVS VTCKASQSVD SNVAWYQQKP RQSPKALIFS ASLRFSGVPA    60
RFTGSGSGTD FTLTISNLQS EDLAEYFCQQ YNNYPLTFGA GTKLELKR                108

SEQ ID NO: 48           moltype = AA  length = 108
FEATURE                 Location/Qualifiers
REGION                  1..108
                        note = VL
source                  1..108
                        mol_type = protein
                        organism = synthetic construct
SEQUENCE: 48
DIVMTQSPAT LSVSVGDEVT LTCKASQSVD SNVAWYQQKP GQAPKLLIYS DDLRFSGVPA    60
RFSGSGSGTD FTLTISSLQS EDFAVYYCQQ YNNYPLTFGA GTKLELKR                108

SEQ ID NO: 49           moltype = AA  length = 108
FEATURE                 Location/Qualifiers
REGION                  1..108
                        note = VL
source                  1..108
                        mol_type = protein
                        organism = synthetic construct
SEQUENCE: 49
EIVMTQSPAT LSVSPGERAT LSCKASQSVD SNVAWYQQKP GQAPRALIYS ASLRFSGIPA    60
RFSGSGSGTE FTLTISSLQS EDFAVYYCQQ YNNYPLTFGA GTKLELKR                108

SEQ ID NO: 50           moltype = AA  length = 108
FEATURE                 Location/Qualifiers
source                  1..108
                        mol_type = protein
                        organism = synthetic construct
VARIANT                 30..31
                        note = XX is glu-ser, ser-ser, thr-ser, gln-ser, his-ser or
                        asp-his
SEQUENCE: 50
EIVMTQSPAT LSVSPGERAT LSCKASQSVX XNVAWYQQKP GQAPRALIYS ASLRFSGIPA    60
RFSGSGSGTE FTLTISSLQS EDFAVYYCQQ YNNYPLTFGA GTKLELKR                108

SEQ ID NO: 51           moltype = AA  length = 108
FEATURE                 Location/Qualifiers
source                  1..108
                        mol_type = protein
                        organism = synthetic construct
VARIANT                 31
                        note = X is ser, his, thr, asn, asp or gln
VARIANT                 32
                        note = X is asn, glu or gln
VARIANT                 34
                        note = X is ala, gly, val, ser, thr, leu or ile
VARIANT                 36
                        note = X is tyr, phe, leu, ile, val, ala or gly
VARIANT                 49
                        note = X is tyr, phe or leu
VARIANT                 50
                        note = X is ser or thr
VARIANT                 52
                        note = X is ser, thr, asp, asn, his, glu or gln
VARIANT                 53
                        note = X is leu, val, ile or met
VARIANT                 55
                        note = X is phe, leu, ile, val, tyr or met
VARIANT                 66
                        note = X is any amino acid
VARIANT                 67
                        note = X is any amino acid
VARIANT                 99
                        note = X is gln, val, leu, ile or met
VARIANT                 101
                        note = X is tyr, phe, leu, ile or gln
VARIANT                 104
                        note = X is tyr, phe, arg, gln or lys
VARIANT                 106
                        note = X is leu, ile, val or phe
SEQUENCE: 51
EIVMTQSPAT LSVSPGERAT LSCKASQSVD XXVXWXQQKP GQAPRALIXX AXXRXSGIPA    60
```

-continued

```
RFSGSXXGTE FTLTISSLQS EDFAVYYCXQ XNNXPXTFGA GTKLELKR              108

SEQ ID NO: 52           moltype = AA  length = 108
FEATURE                 Location/Qualifiers
REGION                  1..108
                        note = VL
source                  1..108
                        mol_type = protein
                        organism = synthetic construct
SEQUENCE: 52
EIVMTQSPAT LSVSPGERAT LSCKASQSVE SNVAWYQQKP GQAPRALIYS ASLRFSGIPA  60
RFSGSGSGTE FTLTISSLQS EDFAVYYCQQ YNNYPLTFGA GTKLELKR              108

SEQ ID NO: 53           moltype = AA  length = 120
FEATURE                 Location/Qualifiers
source                  1..120
                        mol_type = protein
                        organism = synthetic construct
VARIANT                 1
                        note = X is gln or glu
VARIANT                 5
                        note = X is gln or val
VARIANT                 6
                        note = X is gln or glu
VARIANT                 19
                        note = X is lys or arg
VARIANT                 27
                        note = X is ile or phe
VARIANT                 28
                        note = X is asp or thr
VARIANT                 30
                        note = X is ser or asp
VARIANT                 31
                        note = X is arg or asp
VARIANT                 34
                        note = X is ile, phe, leu, val, tyr, cys, gly, ala ser or
                         thr
VARIANT                 39
                        note = X is arg or gln
VARIANT                 48
                        note = X is ile or val
VARIANT                 54
                        note = X is ser, asn, thr, gly, lys, arg or asp
VARIANT                 66
                        note = X is asp or gly
VARIANT                 67
                        note = X is lys or arg
VARIANT                 69
                        note = X is ile or thr
VARIANT                 84
                        note = X is ser or asn
VARIANT                 85
                        note = X is lys or ser
VARIANT                 86
                        note = X is val or leu
VARIANT                 88
                        note = X is ser or ala
VARIANT                 93
                        note = X is leu or val
VARIANT                 107
                        note = X is tyr, leu, phe, ile, val, ala or cys
VARIANT                 115
                        note = X is ser or leu
SEQUENCE: 53
XVQLXXSGGG LVQPGGSLXL SCAASGXXFX XYWXSWVRXA PGKGLEWXGE INPXSSTINY  60
APSLKXXFXI SRDNAKNTLY LQMXXXRXED TAXYYCASLY YDYGDAXDYW GQGTXVTVSS  120

SEQ ID NO: 54           moltype = AA  length = 108
FEATURE                 Location/Qualifiers
source                  1..108
                        mol_type = protein
                        organism = synthetic construct
VARIANT                 8
                        note = X is gln or pro
VARIANT                 9
                        note = X is arg or ala
VARIANT                 10
                        note = X is phe or thr
VARIANT                 11
```

| | | |
|---|---|---|
| VARIANT | 12 | |
| | note = X is met or leu | |
| VARIANT | 13 | |
| | note = X is thr or ser | |
| VARIANT | 18 | |
| | note = X is thr or val | |
| VARIANT | 20 | |
| | note = X is arg or glu | |
| VARIANT | 21 | |
| | note = X is ser or thr | |
| VARIANT | 41 | |
| | note = X is val or leu | |
| VARIANT | 43 | |
| | note = X is arg or gly | |
| VARIANT | 46 | |
| | note = X is ser or ala | |
| VARIANT | 49 | |
| | note = X is ala or leu | |
| VARIANT | 51 | |
| | note = X is phe or tyr | |
| VARIANT | 52 | |
| | note = X is ala or asp | |
| VARIANT | 63 | |
| | note = X is ser or asp | |
| VARIANT | 77 | |
| | note = X is thr or ser | |
| VARIANT | 83 | |
| | note = X is asn or ser | |
| VARIANT | 85 | |
| | note = X is leu or phe | |
| VARIANT | 87 | |
| | note = X is glu or val | |
| | note = X is phe or tyr | |

SEQUENCE: 54
```
DIVMTQSXXX XXXSVGDXVX XTCKASQSVE SNVAWYQQKP XQXPKXLIXS XXLRFSGVPA    60
RFXGSGSGTD FTLTISXLQS EDXAXYXCQQ YNNYPLTFGA GTKLELKR              108
```

| | | |
|---|---|---|
| SEQ ID NO: 55 | moltype = AA  length = 21 | |
| FEATURE | Location/Qualifiers | |
| REGION | 1..21 | |
| | note = leader | |
| source | 1..21 | |
| | mol_type = protein | |
| | organism = synthetic construct | |

SEQUENCE: 55
```
MDFQVQIFSF LLISASVIMS R                                            21
```

| | | |
|---|---|---|
| SEQ ID NO: 56 | moltype = AA  length = 21 | |
| FEATURE | Location/Qualifiers | |
| REGION | 1..21 | |
| | note = leader | |
| source | 1..21 | |
| | mol_type = protein | |
| | organism = synthetic construct | |

SEQUENCE: 56
```
MLLLVTSLLL CELPHPAFLL I                                            21
```

| | | |
|---|---|---|
| SEQ ID NO: 57 | moltype = AA  length = 684 | |
| FEATURE | Location/Qualifiers | |
| REGION | 1..684 | |
| | note = construct | |
| source | 1..684 | |
| | mol_type = protein | |
| | organism = synthetic construct | |

SEQUENCE: 57
```
MDFQVQIFSF LLISASVIMS REVQLVESGG GLVQPGGSLR LSCAASGFTF SRYWFSWVRQ    60
APGKGLVWVG EINPSSSTIN YAPSLKDKFT ISRDNAKNTL YLQMNSLRAE DTAVYYCASL   120
YDYGDAYDY WGQGTLVTVS SGSTSGSGKP GSGEGSTKGE IVMTQSPATL SVSPGERATL    180
SCKASQSVES NVAWYQQKPG QAPRALIYSA SLRFSGIPAR FSGSGSGTEF TLTISSLQSE   240
DFAVYYCQQY NNYPLTFGAG TKLELKPAEP KSPDKTHTCP PCPAPPVAGP SVFLFPPKPK   300
DTLMIARTPE VTCVVVDVSH EDPEVKFNWY VDGVEVHNAK TKPREEQYNS TYRVVSVLTV   360
LHQDWLNGKE YKCKVSNKAL PAPIEKTISK AKGQPREPQV YTLPPSRDEL TKNQVSLTCL   420
VKGFYPSDIA VEWESNGQPE NNYKTTPPVL DSDGSFFLYS KLTVDKSRWQ QGNVFSCSVM   480
HEALHNHYTQ KSLSLSPGKK DPKFWVLVVV GGVLACYSLL VTVAFIIFWV RSKRSRLLHS   540
DYMNMTPRRP GPTRKHYQPY APPRDFAAYR SLRVKFSRSA DAPAYQQGQN QLYNELNLGR   600
REEYDVLDKR RGRDPEMGGK PRRKNPQEGL YNELQKDKMA EAYSEIGMKG ERRRGKGHDG   660
LYQGLSTATK DTYDALHMQA LPPR                                         684
```

| | | |
|---|---|---|
| SEQ ID NO: 58 | moltype = AA  length = 684 | |

```
FEATURE                 Location/Qualifiers
REGION                  1..684
                        note = construct
source                  1..684
                        mol_type = protein
                        organism = synthetic construct
SEQUENCE: 58
MDFQVQIFSF LLISASVIMS REIVMTQSPA TLSVSPGERA TLSCKASQSV ESNVAWYQQK   60
PGQAPRALIY SASLRFSGIP ARFSGSGSGT EFTLTISSLQ SEDFAVYYCQ QYNNYPLTFG  120
AGTKLELKGS TSGSGKPGSG EGSTKGEVQL VESGGGLVQP GGSLRLSCAA SGFTFSRYWF  180
SWVRQAPGKG LVWVGEINPS SSTINYAPSL KDKFTISRDN AKNTLYLQMN SLRAEDTAVY  240
YCASLYYDYG DAYDYWGQGT LVTVSSPAEP KSPDKTHTCP PCPAPPVAGP SVFLFPPKPK  300
DTLMIARTPE VTCVVVDVSH EDPEVKFNWY VDGVEVHNAK TKPREEQYNS TYRVVSVLTV  360
LHQDWLNGKE YKCKVSNKAL PAPIEKTISK AKGQPREPQV YTLPPSRDEL TKNQVSLTCL  420
VKGFYPSDIA VEWESNGQPE NNYKTTPPVL DSDGSFFLYS KLTVDKSRWQ QGNVFSCSVM  480
HEALHNHYTQ KSLSLSPGKK DPKFWVLVVV GGVLACYSLL VTVAFIIFWV RSKRSRLLHS  540
DYMNMTPRRP GPTRKHYQPY APPRDFAAYR SLRVKFSRSA DAPAYQQGQN QLYNELNLGR  600
REEYDVLDKR RGRDPEMGGK PRRKNPQEGL YNELQKDKMA EAYSEIGMKG ERRRGKGHDG  660
LYQGLSTATK DTYDALHMQA LPPR                                        684

SEQ ID NO: 59           moltype = AA  length = 684
FEATURE                 Location/Qualifiers
REGION                  1..684
                        note = construct
source                  1..684
                        mol_type = protein
                        organism = synthetic construct
SEQUENCE: 59
MDFQVQIFSF LLISASVIMS REVQLVESGG GLVQPGGSLR LSCAASGFTF SRYWFSWVRQ   60
APGKGLVWVG EINPSSSTIN YAPSLKDKFT ISRDNAKNTL YLQMNSLRAE DTAVYYCASL  120
YYDYGDAYDY WGQGTLVTVS SGSTSGSGKP GSGEGSTKGE IVMTQSPATL SVSPGERATL  180
SCKASQSVES NVAWYQQKPG QAPRALIYSA SLRFSGIPAR FSGSGSGTEF TLTISSLQSE  240
DFAVYYCQQY NNYPLTFGAG TKLELKPAEP KSPDKTHTCP PCPAPPVAGP SVFLFPPKPK  300
DTLMIARTPE VTCVVVDVSH EDPEVKFNWY VDGVEVHNAK TKPREEQYNS TYRVVSVLTV  360
LHQDWLNGKE YKCKVSNKAL PAPIEKTISK AKGQPREPQV YTLPPSRDEL TKNQVSLTCL  420
VKGFYPSDIA VEWESNGQPE NNYKTTPPVL DSDGSFFLYS KLTVDKSRWQ QGNVFSCSVM  480
HEALHNHYTQ KSLSLSPGKK DPKFWVLVVV GGVLACYSLL VTVAFIIFWV RSKRSRLLHS  540
DYMNMTPRRP GPTRKHYQPY APPRDFAAYR SLRVKFSRSA DAPAYQQGQN QLYNELNLGR  600
REEYDVLDKR RGRDPEMGGK PRRKNPQEGL YNELQKDKMA EAYSEIGMKG ERRRGKGHDG  660
LYQGLSTATK DTYDALHMQA LPPR                                        684

SEQ ID NO: 60           moltype = AA  length = 676
FEATURE                 Location/Qualifiers
REGION                  1..676
                        note = construct
source                  1..676
                        mol_type = protein
                        organism = synthetic construct
SEQUENCE: 60
MDFQVQIFSF LLISASVIMS REVQLVESGG GLVQPGGSLR LSCAASGFTF SRYWFSWVRQ   60
APGKGLVWVG EINPSSSTIN YAPSLKDKFT ISRDNAKNTL YLQMNSLRAE DTAVYYCASL  120
YYDYGDAYDY WGQGTLVTVS SGSTSGSGKP GSGEGSTKGE IVMTQSPATL SVSPGERATL  180
SCKASQSVES NVAWYQQKPG QAPRALIYSA SLRFSGIPAR FSGSGSGTEF TLTISSLQSE  240
DFAVYYCQQY NNYPLTFGAG TKLELKESKY GPPCPPCPAP EFEGGPSVFL FPPKPKDTLM  300
ISRTPEVTCV VVDVSQEDPE VQFNWYVDGV EVHNAKTKPR EEQFNSTYRV VSVLTVLHQD  360
WLNGKEYKCK VSNKGLPSSI EKTISKAKGQ PREPQVYTLP PSQEEMTKNQ VSLTCLVKGF  420
YPSDIAVEWE SNGQPENNYK TTPPVLDSDG SFFLYSRLTV DKSRWQEGNV FSCSVMHEAL  480
HNHYTQKSLS LSLGKFWVLV VVGGVLACYS LLVTVAFIIF WVRSKRSRLL HSDYMNMTPR  540
RPGPTRKHYQ PYAPPRDFAA YRSLRVKFSR SADAPAYQQG QNQLYNELNL GRREEYDVLD  600
KRRGRDPEMG GKPRRKNPQE GLYNELQKDK MAEAYSEIGM KGERRRGKGH DGLYQGLSTA  660
TKDTYDALHM QALPPR                                                 676

SEQ ID NO: 61           moltype = AA  length = 566
FEATURE                 Location/Qualifiers
REGION                  1..566
                        note = construct
source                  1..566
                        mol_type = protein
                        organism = synthetic construct
SEQUENCE: 61
MDFQVQIFSF LLISASVIMS REVQLVESGG GLVQPGGSLR LSCAASGFTF SRYWFSWVRQ   60
APGKGLVWVG EINPSSSTIN YAPSLKDKFT ISRDNAKNTL YLQMNSLRAE DTAVYYCASL  120
YYDYGDAYDY WGQGTLVTVS SGSTSGSGKP GSGEGSTKGE IVMTQSPATL SVSPGERATL  180
SCKASQSVES NVAWYQQKPG QAPRALIYSA SLRFSGIPAR FSGSGSGTEF TLTISSLQSE  240
DFAVYYCQQY NNYPLTFGAG TKLELKESKY GPPCPPCPGQ PREPQVYTLP PSQEEMTKNQ  300
VSLTCLVKGF YPSDIAVEWE SNGQPENNYK TTPPVLDSDG SFFLYSRLTV DKSRWQEGNV  360
FSCSVMHEAL HNHYTQKSLS LSLGKFWVLV VVGGVLACYS LLVTVAFIIF WVRSKRSRLL  420
HSDYMNMTPR RPGPTRKHYQ PYAPPRDFAA YRSLRVKFSR SADAPAYQQG QNQLYNELNL  480
GRREEYDVLD KRRGRDPEMG GKPRRKNPQE GLYNELQKDK MAEAYSEIGM KGERRRGKGH  540
```

-continued

```
DGLYQGLSTA TKDTYDALHM QALPPR                                        566

SEQ ID NO: 62           moltype = AA  length = 459
FEATURE                 Location/Qualifiers
REGION                  1..459
                        note = construct
source                  1..459
                        mol_type = protein
                        organism = synthetic construct
SEQUENCE: 62
MDFQVQIFSF LLISASVIMS REVQLVESGG GLVQPGGSLR LSCAASGFTF SRYWFSWVRQ    60
APGKGLVWVG EINPSSSTIN YAPSLKDKFT ISRDNAKNTL YLQMNSLRAE DTAVYYCASL    120
YYDYGDAYDY WGQGTLVTVS SGSTSGSGKP GSGEGSTKGE IVMTQSPATL SVSPGERATL    180
SCKASQSVES NVAWYQQKPG QAPRALIYSA SLRFSGIPAR FSGSGSGTEF TLTISSLQSE    240
DFAVYYCQQY NNYPLTFGAG TKLELKESKY GPPCPPCPFW VLVVVGGVLA CYSLLVTVAF    300
IIFWVRSKRS RLLHSDYMNM TPRRPGPTRK HYQPYAPPRD FAAYRSLRVK FSRSADAPAY    360
QQGQNQLYNE LNLGRREEYD VLDKRRGRDP EMGGKPRRKN PQEGLYNELQ KDKMAEAYSE    420
IGMKGERRRG KGHDGLYQGL STATKDTYDA LHMQALPPR                          459

SEQ ID NO: 63           moltype = AA  length = 680
FEATURE                 Location/Qualifiers
REGION                  1..680
                        note = construct
source                  1..680
                        mol_type = protein
                        organism = synthetic construct
SEQUENCE: 63
MDFQVQIFSF LLISASVIMS REVQLVESGG GLVQPGGSLR LSCAASGFTF SRYWFSWVRQ    60
APGKGLVWVG EINPSSSTIN YAPSLKDKFT ISRDNAKNTL YLQMNSLRAE DTAVYYCASL    120
YYDYGDAYDY WGQGTLVTVS SGSTSGSGKP GSGEGSTKGE IVMTQSPATL SVSPGERATL    180
SCKASQSVES NVAWYQQKPG QAPRALIYSA SLRFSGIPAR FSGSGSGTEF TLTISSLQSE    240
DFAVYYCQQY NNYPLTFGAG TKLELKPAEP KSPDKTHTCP PCPAPPVAGP SVFLFPPKPK    300
DTLMIARTPE VTCVVVDVSH EDPEVKFNWY VDGVEVHNAK TKPREEQYNS TYRVVSVLTV    360
LHQDWLNGKE YKCKVSNKAL PAPIEKTISK AKGQPREPQV YTLPPSRDEL TKNQVSLTCL    420
VKGFYPSDIA VEWESNGQPE NNYKTTPPVL DSDGSFFLYS KLTVDKSRWQ QGNVFSCSVM    480
HEALHNHYTQ KSLSSLSPGK KIYIWAPLAG TCGVLLLSLV ITLYCKRGRK KLLYIFKQPF    540
MRPVQTTQEE DGCSCRFPEE EEGGCELLRV KFSRSADAPA YQQGQNQLYN ELNLGRREEY    600
DVLDKRRGRD PEMGGKPRRK NPQEGLYNEL QKDKMAEAYS EIGMKGERRR GKGHDGLYQG    660
LSTATKDTYD ALHMQALPPR                                               680

SEQ ID NO: 64           moltype = AA  length = 680
FEATURE                 Location/Qualifiers
REGION                  1..680
                        note = construct
source                  1..680
                        mol_type = protein
                        organism = synthetic construct
SEQUENCE: 64
MDFQVQIFSF LLISASVIMS REIVMTQSPA TLSVSPGERA TLSCKASQSV ESNVAWYQQK    60
PGQAPRALIY SASLRFSGIP ARFSGSGSGT EFTLTISSLQ SEDFAVYYCQ QYNNYPLTFG    120
AGTKLELKGS TSGSGKPGSG EGSTKGEVQL VESGGGLVQP GGSLRLSCAA SGFTFSRYWF    180
SWVRQAPGKG LVWVGEINPS SSTINYAPSL KDKFTISRDN AKNTLYLQMN SLRAEDTAVY    240
YCASLYYDYG DAYDYWGQGT LVTVSSPAEP KSPDKTHTCP PCPAPPVAGP SVFLFPPKPK    300
DTLMIARTPE VTCVVVDVSH EDPEVKFNWY VDGVEVHNAK TKPREEQYNS TYRVVSVLTV    360
LHQDWLNGKE YKCKVSNKAL PAPIEKTISK AKGQPREPQV YTLPPSRDEL TKNQVSLTCL    420
VKGFYPSDIA VEWESNGQPE NNYKTTPPVL DSDGSFFLYS KLTVDKSRWQ QGNVFSCSVM    480
HEALHNHYTQ KSLSSLSPGK KIYIWAPLAG TCGVLLLSLV ITLYCKRGRK KLLYIFKQPF    540
MRPVQTTQEE DGCSCRFPEE EEGGCELLRV KFSRSADAPA YQQGQNQLYN ELNLGRREEY    600
DVLDKRRGRD PEMGGKPRRK NPQEGLYNEL QKDKMAEAYS EIGMKGERRR GKGHDGLYQG    660
LSTATKDTYD ALHMQALPPR                                               680

SEQ ID NO: 65           moltype = AA  length = 680
FEATURE                 Location/Qualifiers
REGION                  1..680
                        note = construct
source                  1..680
                        mol_type = protein
                        organism = synthetic construct
SEQUENCE: 65
MDFQVQIFSF LLISASVIMS REVQLVESGG GLVQPGGSLR LSCAASGFTF SRYWFSWVRQ    60
APGKGLVWVG EINPSSSTIN YAPSLKDKFT ISRDNAKNTL YLQMNSLRAE DTAVYYCASL    120
YYDYGDAYDY WGQGTLVTVS SGSTSGSGKP GSGEGSTKGE IVMTQSPATL SVSPGERATL    180
SCKASQSVES NVAWYQQKPG QAPRALIYSA SLRFSGIPAR FSGSGSGTEF TLTISSLQSE    240
DFAVYYCQQY NNYPLTFGAG TKLELKPAEP KSPDKTHTCP PCPAPPVAGP SVFLFPPKPK    300
DTLMIARTPE VTCVVVDVSH EDPEVKFNWY VDGVEVHNAK TKPREEQYNS TYRVVSVLTV    360
LHQDWLNGKE YKCKVSNKAL PAPIEKTISK AKGQPREPQV YTLPPSRDEL TKNQVSLTCL    420
VKGFYPSDIA VEWESNGQPE NNYKTTPPVL DSDGSFFLYS KLTVDKSRWQ QGNVFSCSVM    480
HEALHNHYTQ KSLSSLSPGK KIYIWAPLAG TCGVLLLSLV ITLYCKRGRK KLLYIFKQPF    540
MRPVQTTQEE DGCSCRFPEE EEGGCELLRV KFSRSADAPA YQQGQNQLYN ELNLGRREEY    600
```

```
DVLDKRRGRD PEMGGKPRRK NPQEGLYNEL QKDKMAEAYS EIGMKGERRR GKGHDGLYQG    660
LSTATKDTYD ALHMQALPPR                                                680

SEQ ID NO: 66          moltype = DNA  length = 360
FEATURE                Location/Qualifiers
misc_feature           1..360
                       note = VH
source                 1..360
                       mol_type = other DNA
                       organism = synthetic construct
SEQUENCE: 66
gaggtgcagc tggtggaatc tggcggagga ctggtgcagc ctggcggctc tctgagactg    60
tcttgtgccg ccagcggctt caccttcagc cggtactggt ttagctgggt gcgccaggcc   120
cctggcaagg gactcgtgtg ggtgggagag atcaacccca gcagcagcac catcaactac   180
gcccccagcc tgaaggacaa gttcaccatc agcagagaca cgccaagaa caccctgtac    240
ctgcagatga acagcctgcg ggccgaggac accgccgtgt actattgtgc cagcctgtac   300
tacgactacg cgacgcccta cgattactgg ggccagggca cactggtgac tgttagctcc   360

SEQ ID NO: 67          moltype = DNA  length = 321
FEATURE                Location/Qualifiers
misc_feature           1..321
                       note = VL
source                 1..321
                       mol_type = other DNA
                       organism = synthetic construct
SEQUENCE: 67
gagatcgtga tgacacagag ccctgccacc ctgagcgtgt ccccaggcga aagagctacc    60
ctgagctgca aggccagcca gagcgtggaa agcaacgtgg cctggtatca gcagaagccc   120
ggacaggctc ctcgggccct gatctacagc gccagctga gattcagcgg catccccgcc    180
aggtttagcg gctctggcag cggcaccgag ttcaccctga caatcagcag cctgcagagc   240
gaggactttg ccgtgtatta ctgccagcag tacaacaact accccctgac cttcggagcc   300
ggcaccaagc tggagctgaa g                                             321

SEQ ID NO: 68          moltype = DNA  length = 360
FEATURE                Location/Qualifiers
misc_feature           1..360
                       note = VH
source                 1..360
                       mol_type = other DNA
                       organism = synthetic construct
SEQUENCE: 68
gaagtgcagc tggtcgaatc tggaggaggc ctggttcagc ctggtggcag ccttaggctc    60
tcttgtgcag cctctggctt taccttctca cggtattggt tcagctgggt gagacaggct   120
ccagggaaag gtctggtgtg ggtagggag ataaacccca gcagcagcac gatcaactat    180
gctccgtcac tgaaagacaa gttcaccatt tcccgcgata tgccaagaa cactctctac    240
ttgcagatga attcccttcg agccgaggat acagcgtgt actactgcgc cagtctgtac    300
tacgactatg gggacgcata cgactattgg ggacaaggca cactggtgac tgttagctcc   360

SEQ ID NO: 69          moltype = DNA  length = 321
FEATURE                Location/Qualifiers
misc_feature           1..321
                       note = VL
source                 1..321
                       mol_type = other DNA
                       organism = synthetic construct
SEQUENCE: 69
gagatcgtga tgacccagtc tcctgctacc ctgagcgttt ctcccggtga aagggccaca    60
ctcagctgca agcctctca aagcgtggag agcaatgtcg cctggtatca gcagaaacct   120
ggccaagctc cgagagcact gatctattcc gcgtcattgc gctttccgg cataccagca    180
cggtttagtg gctcagggag tgggactgag ttcactctga cgattagctc ccttcagtca   240
gaggatttcg ccgtgtacta ctgtcagcag tacaacaact atccccctcac attcggagct  300
ggaaccaagc tggaactgaa g                                             321

SEQ ID NO: 70          moltype = DNA  length = 63
FEATURE                Location/Qualifiers
misc_feature           1..63
                       note = leader
source                 1..63
                       mol_type = other DNA
                       organism = synthetic construct
SEQUENCE: 70
atggatttcc aggtgcagat cttcagcttc ctgctgatct ccgccagcgt gatcatgagc    60
cgc                                                                 63

SEQ ID NO: 71          moltype = DNA  length = 63
FEATURE                Location/Qualifiers
misc_feature           1..63
                       note = leader
source                 1..63
```

```
                        mol_type = other DNA
                        organism = synthetic construct
SEQUENCE: 71
atgcttctcc tggtgacaag ccttctgctc tgtgagttac cacacccagc attcctcctg    60
atc                                                                  63

SEQ ID NO: 72           moltype = DNA   length = 54
FEATURE                 Location/Qualifiers
misc_feature            1..54
                        note = linker
source                  1..54
                        mol_type = other DNA
                        organism = synthetic construct
SEQUENCE: 72
ggcagcacca gcggctccgg caagcctggc tctggcgagg gcagcacaaa ggga          54

SEQ ID NO: 73           moltype = DNA   length = 51
FEATURE                 Location/Qualifiers
misc_feature            1..51
                        note = linker
source                  1..51
                        mol_type = other DNA
                        organism = synthetic construct
SEQUENCE: 73
tctagcggcg gaggcggatc tggcggggga ggatctgggg gaggcggctc t             51

SEQ ID NO: 74           moltype = DNA   length = 702
FEATURE                 Location/Qualifiers
misc_feature            1..702
                        note = spacer
source                  1..702
                        mol_type = other DNA
                        organism = synthetic construct
SEQUENCE: 74
cctgccgagc ctaagagccc cgacaagacc cacacctgtc cccttgtcc tgccctcca      60
gtggctggcc ctagcgtgtt cctgttcccc caaagccca aggataccct gatgatcgcc    120
cggacccccg aagtcacatg cgtggtggtg gacgtgagcc acgaagaccc tgaggtcaag   180
ttcaactggt acgtggacgg cgtggaggtg cataatgcca agacaaagcc gcgggaggag   240
cagtacaaca gcacgtaccg tgtggtcagc gtcctcaccg tcctgcacca ggactggctg   300
aatggcaagg agtacaagtg caaggtctcc aacaaagccc tcccagcccc catcgagaaa   360
accatctcca aagccaaagg gcagccccga gaaccacagg tgtacaccct gcccccatcc   420
cgggatgagc tgaccaagaa ccaggtcagc ctgacctgcc tggtcaaagg cttctatccc   480
agcgacatcg ccgtggagtg ggagagcaat gggcagccgg agaacaacta caagaccacg   540
cctcccgtgc tggactccga cggctccttc ttcctctaca gcaagctcac cgtggacaag   600
agcaggtggc agcaggggaa cgtcttctca tgctccgtga tgcatgaggc tctgcacaac   660
cactacacgc agaagagcct ctccctgtct ccgggtaaaa aa                      702

SEQ ID NO: 75           moltype = DNA   length = 705
FEATURE                 Location/Qualifiers
misc_feature            1..705
                        note = spacer
source                  1..705
                        mol_type = other DNA
                        organism = synthetic construct
SEQUENCE: 75
cctgccgagc ctaagagccc cgacaagacc cacacctgtc cccttgtcc tgccctcca      60
gtggctggcc ctagcgtgtt cctgttcccc caaagccca aggataccct gatgatcgcc    120
cggacccccg aagtcacatg cgtggtggtg gacgtgagcc acgaagaccc tgaggtcaag   180
ttcaactggt acgtggacgg cgtggaggtg cataatgcca agacaaagcc gcgggaggag   240
cagtacaaca gcacgtaccg tgtggtcagc gtcctcaccg tcctgcacca ggactggctg   300
aatggcaagg agtacaagtg caaggtctcc aacaaagccc tcccagcccc catcgagaaa   360
accatctcca aagccaaagg gcagccccga gaaccacagg tgtacaccct gcccccatcc   420
cgggatgagc tgaccaagaa ccaggtgtcc ctgacctgcc tcgtgaaggg cttctacccc   480
tccgatatcg ccgtggaatg ggagagcaat ggccagccgg agaacaacta caagaccacg   540
cccccctgtgc tggacagcga cggctcattc ttcctgtaca gcaagctgac agtggacaag   600
agccggtggc agcagggcaa cgtgttcagc tgcagcgtga tgcacgaggc tctgcacaac   660
cactcacccc agaagtccct gagcagcctg agcccaggca gaag                    705

SEQ ID NO: 76           moltype = DNA   length = 687
FEATURE                 Location/Qualifiers
misc_feature            1..687
                        note = spacer
source                  1..687
                        mol_type = other DNA
                        organism = synthetic construct
SEQUENCE: 76
gagagcaagt acggccctcc ctgcccccct tgccctgccc ccgagttcga gggcggaccc    60
agcgtgttcc tgttcccccc caagcccaag gacaccctga tgatcagccg gacccccgag   120
gtgacctgcg tggtggtgga cgtgagccag gaagatcccg aggtccagtt caattggtac   180
```

```
gtggacggcg tggaagtgca caacgccaag accaagccca gagaggaaca gttcaacagc    240
acctaccggg tggtgtctgt gctgaccgtg ctgcaccagg actggctgaa cggcaaagaa    300
tacaagtgca aggtgtccaa caagggcctg cccagcagca tcgaaaagac catcagcaag    360
gccaaggggcc agcctcgcga gccccaggtg tacaccctgc ctccctccca ggaagagatg    420
accaagaacc aggtgtccct gacctgcctg gtgaaggact ctacccccag cgacatcgcc    480
gtggagtggg agagcaacgg ccagcctgag aacaactaca agaccacccc tcccgtgctg    540
gacagcgacg gcagcttctt cctctacagc cggctgaccg tggacaagag ccggtggcag    600
gaaggcaacg tctttagctg cagcgtgatg cacgaggccc tgcacaacca ctacacccag    660
aagagcctga gcctgtccct gggcaag                                        687

SEQ ID NO: 77           moltype = DNA   length = 357
FEATURE                 Location/Qualifiers
misc_feature            1..357
                        note = spacer
source                  1..357
                        mol_type = other DNA
                        organism = synthetic construct
SEQUENCE: 77
gagagcaagt acggccctcc ctgccccccct tgcctggcc agcctcgcga gccccaggtg    60
tacaccctgc ctccctccca ggaagagatg accaagaacc aggtgtccct gacctgcctg   120
gtgaaggact ctacccccag cgacatcgcc gtggagtggg agagcaacgg ccagcctgag   180
aacaactaca agaccacccc tcccgtgctg gacagcgacg gcagcttctt cctctacagc   240
cggctgaccg tggacaagag ccggtggcag gaaggcaacg tctttagctg cagcgtgatg   300
cacgaggccc tgcacaacca ctacacccag aagagcctga gcctgtccct gggcaag      357

SEQ ID NO: 78           moltype = DNA   length = 36
FEATURE                 Location/Qualifiers
misc_feature            1..36
                        note = spacer
source                  1..36
                        mol_type = other DNA
                        organism = synthetic construct
SEQUENCE: 78
gagagcaagt acgccctcc ctgccccccct tgccct                              36

SEQ ID NO: 79           moltype = DNA   length = 72
FEATURE                 Location/Qualifiers
misc_feature            1..72
                        note = transmembrane
source                  1..72
                        mol_type = other DNA
                        organism = synthetic construct
SEQUENCE: 79
atctacatct gggcccctct ggccggcacc tgtggcgtgc tgctgctgtc tctcgtgatc    60
acactgtact gc                                                        72

SEQ ID NO: 80           moltype = DNA   length = 81
FEATURE                 Location/Qualifiers
misc_feature            1..81
                        note = transmembrane
source                  1..81
                        mol_type = other DNA
                        organism = synthetic construct
SEQUENCE: 80
ttttgggtgc tggtggtggt tggtggagtc ctggcttgct atagcttgct agtaacagtg    60
gcctttatta ttttctgggt g                                              81

SEQ ID NO: 81           moltype = DNA   length = 126
FEATURE                 Location/Qualifiers
misc_feature            1..126
                        note = intracellular
source                  1..126
                        mol_type = other DNA
                        organism = synthetic construct
SEQUENCE: 81
aagcggggca gaaagaagct gctgtacatc ttcaagcagc ccttcatgcg gcccgtgcag    60
accacccagg aagaggacgg ctgctcctgc agattccccg aggaagaaga aggcggctgc   120
gagctg                                                              126

SEQ ID NO: 82           moltype = DNA   length = 123
FEATURE                 Location/Qualifiers
misc_feature            1..123
                        note = intracellular
source                  1..123
                        mol_type = other DNA
                        organism = synthetic construct
SEQUENCE: 82
aggagtaaga ggagcaggct cctgcacagt gactacatga acatgactcc ccgccgcccc    60
gggcccaccg gcaagcatta ccagccctat gccccaccac gcgacttcgc agcctatcgc   120
```

```
tcc                                                                      123

SEQ ID NO: 83           moltype = DNA   length = 123
FEATURE                 Location/Qualifiers
misc_feature            1..123
                        note = intracellular
source                  1..123
                        mol_type = other DNA
                        organism = synthetic construct
SEQUENCE: 83
aggagtaaga ggagcaggct cctgcacagt gactacatga acatgactcc ccgtcgaccc          60
gggcccaccc gcaagcatta ccagccctat gccccaccac gcgacttcgc agcctatcgc         120
tcc                                                                      123

SEQ ID NO: 84           moltype = DNA   length = 342
FEATURE                 Location/Qualifiers
misc_feature            1..342
                        note = intracellular
source                  1..342
                        mol_type = other DNA
                        organism = synthetic construct
SEQUENCE: 84
ctgagagtga agttcagcag gagcgcagac gcccccgcgt accagcaggg ccagaaccag          60
ctctataacg agctcaatct aggacgaaga gaggagtacg atgttttgga caagagacgt         120
ggccgggacc ctgagatggg gggaaagccg agaaggaaga acccctcagga aggcctgtac        180
aatgaactgc agaaagataa gatggcggag gcctacagtg agattgggat gaaaggcgag         240
cgccggaggg gcaaggggca cgatggcctt taccaggtc tcagtacagc caccaaggac          300
acctacgacg cccttcacat gcaggccctg cccctcgct ga                            342

SEQ ID NO: 85           moltype = DNA   length = 339
FEATURE                 Location/Qualifiers
misc_feature            1..339
                        note = intracellular
source                  1..339
                        mol_type = other DNA
                        organism = synthetic construct
SEQUENCE: 85
ctgcgcgtga agttttctag aagcgccgac gcccctgcct accagcaggg ccagaaccag          60
ctgtacaacg agctgaacct gggcagacgg gaagagtacg acgtgctggg taagcgcgaga       120
ggccgggacc ctgagatggg cggcaagcct agaagaaaga accccccagga aggcctgtat       180
aacgaactgc agaaagacaa gatggccgag gcctacagcg agatcggaat gaagggcgag        240
cggagaagag gcaagggcca cgatggactg taccagggcc tgagcaccgc caccaaggac        300
acctatgacg ccctgcacat gcaggctctg ccccccaga                               339

SEQ ID NO: 86           moltype = DNA   length = 2055
FEATURE                 Location/Qualifiers
misc_feature            1..2055
                        note = construct
source                  1..2055
                        mol_type = other DNA
                        organism = synthetic construct
SEQUENCE: 86
atggatttcc aggtgcagat cttcagcttc ctgctgatct ccgccagcgt gatcatgagc          60
cgcgaggtgc agctggtgga atctggcgga ggactggtgc agcctggcgg ctctctgaga         120
ctgtcttgtg ccgccagcgg cttcaccttc agccggtact ggtttagctg ggtgcgccag         180
gcccctggca agggactcgg gtgggtggga gagatcaacc ccagcagcag caccatcaac         240
tacgccccca gcctgaagga caagttcacc atcagcagag acaacgccaa gaacaccctg         300
tacctgcaga tgaacagcct gcgggccgag gacaccgccg tgtactattg tgccagcctg         360
tactacgact acggcgacgc ctacgattac tgggggccagg gcacactggt gactgttagc        420
tccggcagca ccaagggctc cggcaagcct ggctctggcg agggcagcac aaagggagag         480
atcgtgatga cacagagccc tgccaccctg agcgtgtccc caggcgaaag agctaccctg         540
agctgcaagg ccagccagag cgtggaaagc aacgtggcct ggtatcagca gaagcccgga         600
caggctcctc gggccctgat ctacagcgcc agcctgagat tcagcggcat cccgccagg          660
tttagcggct ctggcagcgg caccgagttc acctgacaa tcagcagcct gcagagcgag          720
gactttgccg tgtattactg ccagcagtac aacaactacc ccctgacctt cggagccggc         780
accaagctgg agctgaagcc tgccgagcct aagagcccg acaagaccca cacctgtccc         840
ccttgtcctg cccctccagt ggctggccct agcgtgttcc tgttcccccc aaagcccaag         900
gatacccctga tgatcgcccg gacccccgaa gtcacatgcg tggtggtgga cgtgagccac        960
gaagaccctg aggtcaagtt caactggtac gtggacggcg tggaggtgca taatgccaag       1020
acaaagccgc gggaggagca gtacaacagc acgtaccgtg tggtcagcgt cctcaccgtc       1080
ctgcaccagg actggctgaa tggcaaggag tacaagtgca aggtctccaa caaagccctc        1140
ccagccccca tcgagaaaac catctccaaa gccaagggc agccccgaga accacaggtg        1200
tacaccctgc cccatcccg ggatgagctg accaagaacc aggtcagcct gacctgcctg        1260
gtcaaaggct tctatcccag cgacatcgcc gtggagtggg agagcaatgg gcagccggag        1320
aacaactaca agaccacgcc tcccgtgctg gactccgacg gctccttctt cctctacagc        1380
aagctcaccg tggacaagag caggtggcag caggggaacg tcttctcatg ctccgtgatg        1440
catgaggctc tgcacaacca ctacacgcag aagagcctct ccctgtctcc gggtaaaaaa       1500
gatcccaaat tttgggtgct ggtggtggtt ggtggagtcc tggcttgcta tagcttgcta        1560
gtaacagtgg ccttttattat tttctgggtg aggagtaaga ggagcaggct cctgcacagt       1620
```

```
gactacatga acatgactcc ccgccgcccc gggcccaccc gcaagcatta ccagccctat   1680
gccccaccac gcgacttcgc agcctatcgc tccctgagag tgaagttcag caggagcgca   1740
gacgccccg  cgtaccagca gggccagaac cagctctata acgagctcaa tctaggacga   1800
agagaggagt acgatgtttt ggacaagaga cgtggccggg accctgagat gggggggaaag  1860
ccgagaagga agaaccctca ggaaggcctg tacaatgaac tgcagaaaga taagatggcg   1920
gaggcctaca gtgagattgg gatgaaaggc gagcgccgga ggggcaaggg gcacgatggc   1980
ctttaccagg gtctcagtac agccaccaag gacacctacg acgccttca  catgcaggcc   2040
ctgccccctc gctga                                                   2055

SEQ ID NO: 87           moltype = DNA  length = 2055
FEATURE                 Location/Qualifiers
misc_feature            1..2055
                        note = construct
source                  1..2055
                        mol_type = other DNA
                        organism = synthetic construct
SEQUENCE: 87
atggatttcc aggtgcagat cttcagcttc ctgctgatct ccgccagcgt gatcatgagc    60
cgcgagatcg tgatgacaca gagccctgcc accctgagcg tgtccccagg cgaaagagct   120
accctgagct gcaaggccag ccagagcgtg aaaagcaacg tggcctggta tcagcagaag   180
cccggacagg ctcctcgggc cctgatctac agcgccagcc tgagattcag cggcatcccc   240
gccaggttta gcggctctgg cagcggcacc gagttcaacc tgacaatcag cagcctgcag   300
agcgaggact ttgccgtgta ttactgccaa cagtacaaca actacccct  gaccttcgga   360
gccggcacca gctggagct  gaagggcagc cagcggct   ccgcaagcc tggctctggc   420
gagggcagca caaagggaga ggtgcagctg gtggaatctg cggaggact  ggtgcagcct   480
ggcggctctc tgagactgtc ttgtgccgcc agcggcttca ccttcagcg  gtactggttt   540
agctgggtgc gccaggcccc tggcaaggga ctcgtgtggg tgggagagat caaccccagc   600
agcagcacca tcaactacgc ccccagcctg aaggacaagt tcaccatcag cagagacaac   660
gccaagaaca ccctgtacct gcagatgaac agcctgcggg ccgaggacac cgccgtgtac   720
tattgtgcca gcctgtacta cgactacgcc gacgcctacg attactgggg ccagggcaca   780
ctggtgactg ttagctcccc tgccgagcct aagagcccg  acaagaccca cacctgtccc   840
ccttgtcctg cccctccagt ggctggccct agctgttcc  tgttcccccc aaagcccaag   900
gatacctga  tgatcgcccg gaccccgaa  gtcacatgcg tggtggtgga cgtgagccac   960
gaagaccctg aggtcaagtt caactggtac gtggacggcg tggaggtgca taatgccaag  1020
acaaagccgc gggaggagca gtacaacagc acgtaccgtg tggtcagcgt cctcaccgtc  1080
ctgcaccagg actggctgaa tggcaaggag tacaagtgca aggtctccaa caaagccctc  1140
ccagcccca  tcgagaaaac catctccaaa gccaaaggc  agcccgaga  accacaggtg  1200
tacaccctgc cccccatccg ggatgagctg accaagaacc aggtcagcct gacctgcctg  1260
gtcaaaggct tctatcccag cgacatcgcc gtggagtgga gagcaatgg  gcagccgaca  1320
aacaactaca agaccacgcc tcccgtgctg gactccgacg gctccttctt cctctacagc  1380
aagctcaccg tggacaagag caggtggcag caggggaacg tcttctcatg ctccgtgatg  1440
catgaggctc tgcacaacca ctacacgcag aagagcctct ccctgtctcc gggtaaaaaa  1500
gatcccaaat tttgggtgct ggtggtggtt ggtggagtcc tggcttgcta tagcttgcta  1560
gtaacagtgg cctttattat tttctgggtg aggagtaaga ggagcaggct cctgcacagt  1620
gactacatga acatgactcc ccgccgcccc gggcccaccc gcaagcatta ccagccctat  1680
gccccaccac gcgacttcgc agcctatcgc tccctgagag tgaagttcag caggagcgca  1740
gacgccccg  cgtaccagca gggccagaac cagctctata acgagctcaa tctaggacga  1800
agagaggagt acgatgtttt ggacaagaga cgtggccggg accctgagat gggggggaaag 1860
ccgagaagga agaaccctca ggaaggcctg tacaatgaac tgcagaaaga taagatggcg  1920
gaggcctaca gtgagattgg gatgaaaggc gagcgccgga ggggcaaggg gcacgatggc  1980
ctttaccagg gtctcagtac agccaccaag gacacctacg acgccttca  catgcaggcc  2040
ctgccccctc gctga                                                  2055

SEQ ID NO: 88           moltype = DNA  length = 2055
FEATURE                 Location/Qualifiers
misc_feature            1..2055
                        note = construct
source                  1..2055
                        mol_type = other DNA
                        organism = synthetic construct
SEQUENCE: 88
atggatttcc aggtgcagat cttcagcttc ctgctgatct ccgccagcgt gatcatgagc    60
cgcgaagtgc agctggtcga atctggagga ggcctggttc agcctggtgg cagccttagg   120
ctctcttgtg cagcctctgg cttttacctt cacggtatt  cagctcagctg ggtgagacag  180
gctccaggga aggtctggt  gtgggtaggg gagataaacc ccagcagcag cacgatcaac   240
tatgctccgt cactgaaaga caagttcacc atttccgcg  ataatgccaa gaacactctc   300
tacttgcaga tgaattccct tcgagccgag gatacagcgg tgtactactg cgccagtctg   360
tactacgact atggggacgc atacgactat tggggacaag gcacactggt gactgttagc   420
tccggcagca ccagcggctc cggcaagcct ggctctggac agggcagcac aaagggagag   480
atcgtgatga cccagtctcc tgctaccctg agcgtttctc ccggtgaaag ggccacactc   540
agctgcaaag cctctcaaag cgtggagagc aatgtcgcct ggtatcagca gaaacctggc   600
caagctccga gcactgat   ctattccgcg tcattgcgct tttccggcat  accagcacgg   660
tttagtggct cagggagtgg gactgagttc actctgacga ttagctccct tcagtcgag   720
gatttcgcag tgtactactg tcagcagtac aacaactccc ctcacatt   cggagctgga   780
accaagctgg aactgaagcc tgccgagcct aagagcccg  acaagaccca cacctgtccc   840
ccttgtcctg cccctccagt ggctggccct agctgttcc  tgttcccccc aaagcccaag   900
gatacctga  tgatcgcccg gaccccgaa  gtcacatgcg tggtggtgga cgtgagccac   960
gaagaccctg aggtcaagtt caactggtac gtggacggcg tggaggtgca taatgccaag  1020
acaaagccgc gggaggagca gtacaacagc acgtaccgtg tggtcagcgt cctcaccgtc  1080
```

-continued

```
ctgcaccagg actggctgaa tggcaaggag tacaagtgca aggtctccaa caaagccctc  1140
ccagcccca tcgagaaaac catctccaaa gccaaagggc agccccgaga accacaggtg  1200
tacaccctgc cccatcccg ggatgagctg accaagaacc aggtcagcct gacctgcctg  1260
gtcaaaggct tctatcccag cgacatcgcc gtggagtggg agagcaatgg gcagccggag  1320
aacaactaca agaccacgcc tcccgtgctg gactccgaca gctccttctt cctctacagc  1380
aagctcaccg tggacaagag caggtggcag caggggaacg tcttctcatg ctccgtgatg  1440
catgaggctc tgcacaacca ctacacgcag aagagcctct ccctgtctcc gggtaaaaaa  1500
gatcccaaat tttgggtgct ggtggtggtt ggtggagtcc tggcttgcta tagcttgcta  1560
gtaacagtgg cctttattat tttctgggtg aggagtaaga ggagcaggct cctgcacagt  1620
gactacatga acatgactcc ccgccgcccc gggcccaccc gcaagcatta ccagccctat  1680
gccccaccac gcgacttcgc agcctatcgc tccctgagag tgaagttcag caggagcgca  1740
gacgcccccg cgtaccagca gggccagaac cagctctata cgagctcaa tctaggacga  1800
agagaggagt acgatgtttt ggacaagaga cgtggccggg accctgagat ggggggaaag  1860
ccgagaagga agaaccctca ggaaggcctg tacaatgaac tgcagaaaga taagatgcgg  1920
gaggcctaca gtgagattgg gatgaaaggc gagcgccgga ggggcaaggg gcacgatggc  1980
ctttaccagg gtctcagtac agccaccaag gacacctacg acgcccttca catgcaggcc  2040
ctgccccctc gctga                                                   2055

SEQ ID NO: 89              moltype = DNA  length = 2031
FEATURE                    Location/Qualifiers
misc_feature               1..2031
                           note = construct
source                     1..2031
                           mol_type = other DNA
                           organism = synthetic construct
SEQUENCE: 89
atggatttcc aggtgcagat cttcagcttc ctgctgatct ccgccagcgt gatcatgagc   60
cgcgaggtgc agctggtgga atctggcgga ggactggtgc agcctggcgg ctctctgaga  120
ctgtcttgtg ccgccagcgg cttcaccttc agccggtact ggtttagctg ggtgcgccag  180
gcccctggca agggactcgt gtgggtggga gagatcaac ccagcagcag caccatcaac  240
tacgccccca gcctgaagga caagttcacc atcagcagag acaacgccaa gaacaccctg  300
tacctgcaga tgaacagcct gcgggccgag gacaccgccg tgtactattg tgccagcctg  360
tactacgact acgcgacgc ctacgattac tggggccagg gcacactggt gactgttagc  420
tccggcagca ccagcggctc cggcaagcct ggctctggcg agggcagcac aaagggagag  480
atcgtgatga cacagagccc tgccaccctg agcgtgtccc caggcgaaag agctaccctg  540
agctgcaagg ccagccagag cgtggaaagc aacgtggcct ggtatcagca gaagcccgga  600
caggctcctc gggccctgat ctacagcgcc agctgagat tcagcggcat ccccgccagg  660
tttttccgga ctggcagcgg caccgagttc accctgacaa tcagcagcct gcagagcgag  720
gactttgccg tgtattactg ccagcagtac aacaactacc ctgtgacctt ccggagccgc  780
accaagctgg agctgaagga gagcaagtac ggcctcccct gccccccttg ccctgccccc  840
gagttcgagg gcggacccag cgtgttcctg ttccccccca gcccaaggga caccctgatg  900
atcagccgga ccccgaggt gacctgcgtg gtggtgacg tgagccagga agatcccgag  960
gtccagttca attggtacgt ggacggcgtg gaagtgcaca acgccaagac caagcccaga 1020
gaggaacagt tcaacagcac ctaccgggtg gtgtctgtgc tgaccgtgct gcaccaggac 1080
tggctgaacg gcaaagaata caagtgcaag gtgtccaaca agggcctgcc cagcagcatc 1140
gaaaagacca tcagcaaggc caagggccag cctcgcgagc ccaggtgta caccctgcct 1200
ccctcccagg aagagatgac caagaaccag gtgtccctga cctgcctggt gaagggcttc 1260
taccccagcg acatcgccgt ggagtgggag agcaacggcc agcctgagaa caactacaag 1320
accacccctc ccgtgctgga cagcgacggc agcttcttcc tctacagccg gctgaccgtg 1380
gacaagagcc ggtggcagga aggcaacgtc tttagctgca gcgtgatgca cgaggccctg 1440
cacaaccact acacccagaa gagcctgagc tgtgtccctgg gcaagttttg ggtgctggtg 1500
gtggttggtg gagtcctggc ttgctatagc ttgctagtaa cagtggcctt tattattttc 1560
tgggtgagga gtaagaggag caggctcctg cacagtgact acatgaacat gactcccgt 1620
cgacccgggc ccaccgcaa gcattaccag ccctatgccc caccgcga cttcgcagcc 1680
tatcgctccc tgagagtgaa gttcagcagg agcgcagacg ccccgcgta ccagcaggc 1740
cagaaccagc tctataacga gctcaatcta ggacgaagag aggagtacga tgttttggac 1800
aagagacgtg gccgggaccc tgagatgggg ggaaagccga aaggaagaa ccctcaggaa 1860
ggcctgtaca tgaactgcag aaagataag atggcggagg cctacagtga gattgggatg 1920
aaaggcgagc gccggagggg caaggggcac gatggccttt accagggtct cagtacagcc 1980
accaaggaca cctacgacgc ccttcacatg caggccctgc cccctcgctg a          2031

SEQ ID NO: 90              moltype = DNA  length = 1701
FEATURE                    Location/Qualifiers
misc_feature               1..1701
                           note = construct
source                     1..1701
                           mol_type = other DNA
                           organism = synthetic construct
SEQUENCE: 90
atggatttcc aggtgcagat cttcagcttc ctgctgatct ccgccagcgt gatcatgagc   60
cgcgaggtgc agctggtgga atctggcgga ggactggtgc agcctggcgg ctctctgaga  120
ctgtcttgtg ccgccagcgg cttcaccttc agccggtact ggtttagctg ggtgcgccag  180
gcccctggca agggactcgt gtgggtggga gagatcaacc ccagcagcag caccatcaac  240
tacgccccca gcctgaagga caagttcacc atcagcagag acaacgccaa gaacaccctg  300
tacctgcaga tgaacagcct gcgggccgag gacaccgccg tgtactattg tgccagcctg  360
tactacgact acgcgacgc ctacgattac tggggccagg gcacactggt gactgttagc  420
tccggcagca ccagcggctc cggcaagcct ggctctggcg agggcagcac aaagggagag  480
atcgtgatga cacagagccc tgccaccctg agcgtgtccc caggcgaaag agctaccctg  540
agctgcaagg ccagccagag cgtggaaagc aacgtggcct ggtatcagca gaagcccgga  600
```

-continued

```
caggctcctc gggccctgat ctacagcgcc agcctgagat tcagcggcat ccccgccagg    660
ttttccggat ctggcagcgg caccgagttc accctgacaa tcagcagcct gcagagcgag    720
gactttgccg tgtattactg ccagcagtac aacaactacc ccctgacctt cggagccggc    780
accaagctgg agctgaagga gagcaagtac ggccctccct gccccccttg ccctggccag    840
cctcgcgacg cccaggtgta caccctgcct cctcccagg aagagatgac caagaaccag    900
gtgtccctga cctgcctggt gaagggcttc taccccagcg acatcgccgt ggagtgggag    960
agcaacggcc agcctgagaa caactacaag accacccctc ccgtgctgga cagcgacggc   1020
agcttcttcc tctacagccg gctgaccgtg gacaagagcc ggtggcagga aggcaacgtc   1080
tttagctgca gcgtgatgca cgaggccctg cacaaccact acacccagaa gagcctgagc   1140
ctgtccctgg gcaagttttg ggtgctggtg gtggttggtg gagtcctggc ttgctatagc   1200
ttgctagtaa cagtggcctt tattattttc tgggtgagga gtaagaggag caggctcctg   1260
cacagtgact acatgaacat gactcccgt cgacccgggc ccaccgcaa gcattaccag    1320
ccctatgccc caccacgcga cttcgcagcc tatcgctccc tgagagtgaa gttcagcagg   1380
agcgcagacg ccccgcgta ccagcagggc cagaaccgac tctataacga gctcaatcta   1440
ggacgaagag aggagtacga tgttttggac aagagacgtg gccgggaccc tgagatgggg   1500
ggaaagccga aggaagaac ccctcaggaa ggcctgtaca tgaactgca gaaagataag    1560
atggcggagg cctacagtga gattgggatg aaaggcgagc gccggagggg caaggggcac   1620
gatggccttt accagggtct cagtacagcc accaaggaca cctacgacgc ccttcacatg   1680
caggccctgc ccctcgctg a                                             1701

SEQ ID NO: 91          moltype = DNA  length = 1380
FEATURE                Location/Qualifiers
misc_feature           1..1380
                       note = construct
source                 1..1380
                       mol_type = other DNA
                       organism = synthetic construct
SEQUENCE: 91
atggatttcc aggtgcagat cttcagcttc ctgctgatct ccgccagcgt gatcatgagc     60
cgcgaggtgc agctggtgga atctggcgga ggactggtgc agcctggcgg ctctctgaga    120
ctgtcttgtg ccgccagcgg cttcaccttc agccggtact ggtttagctg ggtgcgccag    180
gcccctggca agggactcgt gtgggtggga gagatcaacc ccagcagcag caccatcaac    240
tacgccccca gcctgaagga caagttcacc atcagcagag acaacgccaa gaacaccctg    300
tacctgcaga tgaacagcct gcgggccgag gacaccgccg tgtactattg tgccagcctg    360
tactacgact acggcgacgc ctacgattac tggggccagg gcacactggt gactgttagc    420
tccggcagca ccagcggctc cggcaagcct ggctctggcg agggcagcac aaagggagag    480
atcgtgatga cacagagccc tgccaccctg agcgtgtccc aggcgaaag agctaccctg    540
agctgcaagg ccagccagag cgtggaaagc aacgtggcct ggtatcagca gaagcccgga    600
caggctcctc gggccctgat ctacagcgcc agcctgagat tcagcggcat ccccgccagg    660
ttttccggat ctggcagcgg caccgagttc accctgacaa tcagcagcct gcagagcgag    720
gactttgccg tgtattactg ccagcagtac aacaactacc ccctgacctt cggagccggc    780
accaagctgg agctgaagga gagcaagtac ggccctccct gccccccttg ccctttttgg    840
gtgctgctgg tggttggtgg agtcctggct tgctatagct tgctagtaac agtggcctt     900
attatttct gggtgaggag taagaggagc aggcctcctgc acagtgacta catgaacatg    960
actccccgtc gacccgggcc caccgcaag cattaccagc cctatgcccc accacgcgac    1020
ttcgcagcct atcgctccct gagagtgaag ttcagcagga gcgcagacgc cccgcgtac    1080
cagcagggcc agaaccagct ctataacgag ctcaatctag gacgaagaga ggagtacgat   1140
gttttggaca agagacgtgg ccgggaccct gagatggggg gaaagccgag aaggaagaac   1200
cctcaggaag gcctgtacaa tgaactgcag aaagataagt ggcggaggc ctacagtgag    1260
attgggatga aaggcgagcg ccggaggggc aaggggcacg atggcctta ccagggtctc    1320
agtacagcca ccaaggacac ctacgacgcc cttcacatgc aggccctgcc cctcgctga    1380

SEQ ID NO: 92          moltype = DNA  length = 2040
FEATURE                Location/Qualifiers
misc_feature           1..2040
                       note = construct
source                 1..2040
                       mol_type = other DNA
                       organism = synthetic construct
SEQUENCE: 92
atggatttcc aggtgcagat cttcagcttc ctgctgatct ccgccagcgt gatcatgagc     60
cgcgaggtgc agctggtgga atctggcgga ggactggtgc agcctggcgg ctctctgaga    120
ctgtcttgtg ccgccagcgg cttcaccttc agccggtact ggtttagctg ggtgcgccag    180
gcccctggca agggactcgt gtgggtggga gagatcaacc ccagcagcag caccatcaac    240
tacgccccca gcctgaagga caagttcacc atcagcagag acaacgccaa gaacaccctg    300
tacctgcaga tgaacagcct gcgggccgag gacaccgccg tgtactattg tgccagcctg    360
tactacgact acggcgacgc ctacgattac tggggccagg gcacactggt gactgttagc    420
tccggcagca ccagcggctc cggcaagcct ggctctggcg agggcagcac aaagggagag    480
atcgtgatga cacagagccc tgccaccctg agcgtgtccc aggcgaaag agctaccctg    540
agctgcaagg ccagccagag cgtggaaagc aacgtggcct ggtatcagca gaagcccgga    600
caggctcctc gggccctgat ctacagcgcc agcctgagat tcagcggcat ccccgccagg    660
tttagcggct ctggcagcgg caccgagttc accctgacaa tcagcagcct gcagagcgag    720
gactttgccg tgtattactg ccagcagtac aacaactacc ccctgacctt cggagccggc    780
accaagctgg agctgaagcc tgccgagcct aagagcccca acaagacccc acctccaaga    840
ccttgtcctg ccctccagt ggctggccct agcgtgttcc tgttcccccc aaagcccaag    900
gataccctga tgatcgcccg gaccccgaa gtcacatgcg tggtggtgga cgtgagccac    960
gaagaccctg aggtcaagtt caactggtac gtggacggcg tggaggtgca taatgccaag   1020
acaaagccgg gggaggagca gtacaacagc acgtaccgtg tggtcagcgt cctcaccgtc   1080
ctgcaccagg actggctgaa tggcaaggag tacaagtgca aggtctccaa caaagccctc   1140
```

```
ccagccccca tcgagaaaac catctccaaa gccaagggc agccccgaga accacaggtg   1200
tacaccctgc ccccatcccg ggatgagctg accaagaacc aggtgtccct gacctgcctc   1260
gtgaagggct tctacccctc cgatatcgcc gtggaatggg agagcaatgg ccagcccgag   1320
aacaactaca agaccacccc ccctgtgctg acagcgacg gctcattctt cctgtacagc   1380
aagctgacag tggacaagag ccggtggcag cagggcaacg tgttcagctg cagcgtgatg   1440
cacgaggctc tgcacaacca ctacacccag aagtccctga gcagcctgag cccaggcaag   1500
aagatctaca tctgggcccc tctggccggc acctgtggcg tgctgctgct gtctctcgtg   1560
atcacactgt actgcaagcg gggcagaaag aagctgctgt acatcttcaa gcagcccttc   1620
atgcggcccg tgcagaccac caggaagag gacggctgct cctgcagatt ccccgaggaa   1680
gaagaaggcg gctgcgagct gctgcgcgtg aagttttcta gaagcgccga cgccctgcc   1740
taccagcagg gccagaacca gctgtacaac gagctgaacc tgggcagacg ggaagagtac   1800
gacgtgctgg ataagcggag aggccggac cctgagatgg gcggcaagcc tagaagaaag   1860
aaccccagg aaggcctgta taacgaactg cagaaagaca gatggccga ggcctacagc   1920
gagatcggaa tgaagggcga gcggagaaga ggcaagggcc acgatggact gtaccagggc   1980
ctgagcaccg ccaccaagga cacctatgac gccctgcaca tgcaggctct gccccccaga   2040

SEQ ID NO: 93           moltype = DNA    length = 2040
FEATURE                 Location/Qualifiers
misc_feature            1..2040
                        note = construct
source                  1..2040
                        mol_type = other DNA
                        organism = synthetic construct
SEQUENCE: 93
atggatttcc aggtgcagat cttcagcttc ctgctgatct ccgccagcgt gatcatgagc   60
cgcgagatcg tgatgacaca gagccctgcc accctgagcg tgtccccagg cgaaagagct   120
accctgagct gcaaggccag ccagagcgtg aaagcaacg tggcctggta tcagcagaag   180
cccgacagg ctcctcgggc cctgatctac agcgccagcc tgagattcag cggcatcccc   240
gccaggttta gcggctctgg cagcggcacc gagttcaccc tgacaatcag cagcctgcag   300
agcgaggact ttgccgtgta ttactgccag cagtacaaca actaccccct gaccttcgga   360
gccggcacca agctggagct gaagggcagc accagcggct ccggcaagcc tggctctggc   420
gagggcagca caaagggaga ggtgcagctg gtggaatctg gcgaggact ggtgcagcct   480
ggcggctctc tgagactgtc ttgtgccgcc agcggcttca ccttcagccg gtactggttt   540
agctgggtgc gccaggcccc tggcaaggga ctcgtgtggg tgggagagat caacccagtg   600
agcagcacca tcaactacgc cccagcctg aaggacaagt tcaccatcag cagagacaac   660
gccaagaaca ccctgtacct gcagatgaac agcctgcggg ccgaggacac cgccgtgtac   720
tattgtgcca gcctgtacta cgactacggc gacgcctacg attactgggg ccagggcaca   780
ctggtgactg ttagctcccc tgccgagcct aagagcccg acaagaccca cacctgtccc   840
ccttgtcctg ccctccagt ggctggccct agcgtgttcc tgttccccc aaagcccaag   900
gatacccctg tgatcgcccg gacccccgaa gtcacatgc tggtggtgga cgtgagccac   960
gaagaccctg aggtcaagtt caactggtac gtggacggcg tggaggtgca taatgccaag   1020
acaaagccgg ggaggagca gtacaacagc acgtaccgtg tggtcagcgt cctcaccgtc   1080
ctgcaccagg actggctgaa tggcaaggag tacaagtgca aggtctccaa caaagccctc   1140
ccagccccca tcgagaaaac catctccaaa gccaagggc agccccgaga accacaggtg   1200
tacaccctgc ccccatcccg ggatgagctg accaagaacc aggtgtccct gacctgcctc   1260
gtgaagggct tctacccctc cgatatcgcc gtggaatggg agagcaatgg ccagcccgag   1320
aacaactaca agaccacccc ccctgtgctg gacagcgacg gctcattctt cctgtacagc   1380
aagctgacag tggacaagag ccggtggcag cagggcaacg tgttcagctg cagcgtgatg   1440
cacgaggctc tgcacaacca ctacacccag aagtccctga gcagcctgag cccaggcaag   1500
aagatctaca tctgggcccc tctggccggc acctgtggcg tgctgctgct gtctctcgtg   1560
atcacactgt actgcaagcg gggcagaaag aagctgctgt acatcttcaa gcagcccttc   1620
atgcggcccg tgcagaccac caggaagag gacggctgct cctgcagatt ccccgaggaa   1680
gaagaaggcg gctgcgagct gctgcgcgtg aagttttcta gaagcgccga cgccctgcc   1740
taccagcagg gccagaacca gctgtacaac gagctgaacc tgggcagacg ggaagagtac   1800
gacgtgctgg ataagcggag aggccggac cctgagatgg gcggcaagcc tagaagaaag   1860
aaccccagg aaggcctgta taacgaactg cagaaagaca gatggccga ggcctacagc   1920
gagatcggaa tgaagggcga gcggagaaga ggcaagggcc acgatggact gtaccagggc   1980
ctgagcaccg ccaccaagga cacctatgac gccctgcaca tgcaggctct gccccccaga   2040

SEQ ID NO: 94           moltype = DNA    length = 2040
FEATURE                 Location/Qualifiers
misc_feature            1..2040
                        note = construct
source                  1..2040
                        mol_type = other DNA
                        organism = synthetic construct
SEQUENCE: 94
atggatttcc aggtgcagat cttcagcttc ctgctgatct ccgccagcgt gatcatgagc   60
cgcgaagtgc agctggtcga atctggagga ggcctggttc agcctggtgg cagccttagg   120
ctctcttgtg cagcctctgg ctttaccttc tcacggtatt ggttcagctg ggtgagacag   180
gctccaggga aagtctggt gtgggtaggg gagatcaaacc cagcagcag cacgatcaac   240
tatgctccgt cactgaaaga caagttcacc atttcccgcg ataatgccaa gaacactctc   300
tacttgcaga tgaattccct tcgagccgag gatacagcg tgtactactg cgccagtctg   360
tactacgact atggggaagc atacgactat tggggacaag gcacactggt gactgttagc   420
tccggcagca ccagcggctc cggcaagcct ggctctggcg agggcagcac aaagggagag   480
atcgtgatga cccagtctcc tgctaccctg agcgtttctc ccggtgaaag ggccacactc   540
agctgcaaag cctctcaaag cgtggagagc aatgtcgcct ggtatcagca gaaacctggc   600
caagctccga gcactgat ctattccgcg tcattgcgct tttccggcat accagcacgg   660
tttagtggct caggggagtgg gactgagttc actctgacga ttagctccct tcagtcagag   720
```

```
gatttcgccg tgtactactg tcagcagtac aacaactatc ccctcacatt cggagctgga  780
accaagctgg aactgaagcc tgccgagcct aagagcccccg acaagaccca cacctgtccc  840
ccttgtcctg cccctccagt ggctggccct agcgtgttcc tgttcccccc aaagcccaag  900
gatacccctga tgatcgcccg gacccccgaa gtcacatgcg tggtggtgga cgtgagccac  960
gaagaccctg aggtcaagtt caactggtac gtggacggcg tggaggtgca taatgccaag 1020
acaaagccgc gggaggagca gtacaacagc acgtaccgtg tggtcagcgt cctcaccgtc 1080
ctgcaccagg actggctgaa tggcaaggag tacaagtgca aggtctccaa caaagccctc 1140
ccagccccca tcgagaaaac catctccaaa gccaagggc agcccccgaga accacaggtg 1200
tacaccctgc ccccatcccg ggatgagctg accaagaacc aggtgtccct gacctgcctc 1260
gtgaagggct tctacccctc cgatatcgcc gtggaatggg agagcaatgg ccagcccgag 1320
aacaactaca agaccacccc cctgtgctg gacagcgacg gctcattctt cctgtacagc 1380
aagctgacag tggacaagag ccggtggcag cagggcaacg tgttcagctg cagcgtgatg 1440
cacgaggctc tgcacaacca ctacacccag aagtccctga gcagcctgag cccaggcaag 1500
aagatctaca tctgggcccc tctggccggc acctgtggcg tgctgctgct gtctctcgtg 1560
atcacactgt actgcaagcg gggcagaaag aagctgctgt acatcttcaa gcagccccttc 1620
atgcggcccg tgcagaccac ccaggaagag gacggctgct cctgcagatt ccccgaggaa 1680
gaagaaggcg gctgcgagct gctgcgcgtg aagttttcta gaagcgccga cgcccctgcc 1740
taccagcagg gccagaacca gctgtacaac gagctgaacc tgggcagacg ggaagagtac 1800
gacgtgctgg ataagcggag aggccgggac cctgagatgg gcggcaagcc tagaagaaag 1860
aacccccagg aaggcctgta taacgaactg cagaaagaca agatgccgga ggcctacagc 1920
gagatcggaa tgaagggcga gcggagaaga ggcaagggcc acgatggact gtaccagggc 1980
ctgagcaccg ccaccaagga cacctatgac gccctgcaca tgcaggctct gccccccaga 2040
```